(12) United States Patent
Chan et al.

(10) Patent No.: US 7,326,785 B2
(45) Date of Patent: Feb. 5, 2008

(54) PYRROLIDINE DERIVATIVES AS FACTOR XA INHIBITORS

(75) Inventors: Chuen Chan, Stevenage (GB); Julie Nicole Hamblin, Stevenage (GB); Henry Anderson Kelly, Stevenage (GB); Nigel Paul King, Harlow (GB); Andrew McMurtrie Mason, Stevenage (GB); Vipulkumar Kantibhai Patel, Stevenage (GB); Stefan Senger, Stevenage (GB); Gita Punjabhai Shah, Stevenage (GB); Nigel Stephen Watson, Stevenage (GB); Helen Elisabeth Weston, Stevenage (GB); Caroline Whitworth, Stevenage (GB); Robert John Young, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 11/548,404

(22) Filed: Oct. 11, 2006

(65) Prior Publication Data
US 2007/0142375 A1    Jun. 21, 2007

Related U.S. Application Data

(62) Division of application No. 10/479,545, filed as application No. PCT/GB02/02721 on Jun. 6, 2002, now Pat. No. 7,186,717.

(30) Foreign Application Priority Data
Jun. 8, 2001   (GB) ................................ 0114005.2

(51) Int. Cl.
    C07D 413/14    (2006.01)
(52) U.S. Cl. ...................... 544/141; 544/146
(58) Field of Classification Search ............... None
    See application file for complete search history.

(56) References Cited

U.S. PATENT DOCUMENTS

| 5,489,583 | A | 2/1996 | Mack et al. | |
|---|---|---|---|---|
| 6,034,215 | A | 3/2000 | Semple et al. | |
| 6,187,797 | B1 | 2/2001 | Pruit et al. | |
| 6,281,277 | B1 | 8/2001 | Ishii et al. | |
| 7,084,139 | B2* | 8/2006 | Chan et al. | 514/235.5 |
| 7,186,717 | B2* | 3/2007 | Chan et al. | 514/235.5 |
| 7,226,929 | B2* | 6/2007 | Chan et al. | 514/300 |
| 2006/0124049 | A1* | 6/2006 | Dell Orco et al. | 117/2 |
| 2006/0160886 | A1* | 7/2006 | Chan et al. | 514/422 |
| 2007/0142374 | A1* | 6/2007 | Chan et al. | 514/235.2 |
| 2007/0155745 | A1* | 7/2007 | Chan et al. | 514/235.2 |

FOREIGN PATENT DOCUMENTS

| DE | 41 21 947 | 1/1993 |
|---|---|---|
| EP | 365992 | 5/1990 |
| EP | 0 483 667 | 5/1992 |
| EP | 1 031 563 | 8/2000 |
| WO | 93/01208 | 1/1993 |
| WO | 98/16523 | 4/1998 |
| WO | 98/25611 | 6/1998 |
| WO | 98/47876 | 10/1998 |
| WO | 99/37304 | 7/1999 |
| WO | 99/62904 | 12/1999 |
| WO | 00/40578 | 7/2000 |
| WO | 00/47563 | 8/2000 |
| WO | 00/55188 | 9/2000 |
| WO | 00/69465 | 11/2000 |
| WO | 01/07436 | 2/2001 |
| WO | 01/39759 | 6/2001 |
| WO | 02/060894 | 8/2002 |

OTHER PUBLICATIONS

J. Enzyme Inhibition, 1995, 9(1), pp. 73-86.

* cited by examiner

Primary Examiner—Rebecca Anderson
Assistant Examiner—Michael P. Barker
(74) Attorney, Agent, or Firm—Jennifer L. Fox

(57) ABSTRACT

The invention relates to compounds of formula (I)

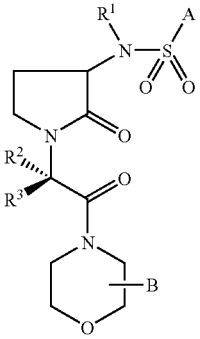

(I)

processes for their preparation, pharmaceutical compositions containing them and to their use in medicine, particularly use in the amelioration of a clinical condition for which a Factor Xa inhibitor is indicated.

3 Claims, No Drawings

PYRROLIDINE DERIVATIVES AS FACTOR XA INHIBITORS

This application is a divisional of U.S. Ser. No. 10/479,545 filed on Dec. 3, 2003, now U.S. Pat. No. 7,186,717 which was filed pursuant to 35 U.S.C. § 371 as a United States National Phase Application of International Application No. PCT/GB02/02721 filed Jun. 6, 2002, which claims priority from GB 0114005.2 filed Jun. 8, 2001.

FIELD OF THE INVENTION

The present invention relates to a novel class of chemical compounds, to processes for their preparation, to pharmaceutical compositions containing them and to their use in medicine, particularly use in the amelioration of a clinical condition for which a Factor Xa inhibitor is indicated.

BACKGROUND OF THE INVENTION

Factor Xa is a member of the trypsin-like serine protease class of enzymes. It is a key enzyme in the coagulation cascade. A one-to-one binding of Factors Xa and Va with calcium ions and phospholipid converts prothrombin into thrombin. Thrombin plays a central role in the mechanism of blood coagulation by converting the soluble plasma protein, fibrinogen, into insoluble fibrin. The insoluble fibrin matrix is required for the stabilisation of the primary hemostatic plug. Many significant disease states are related to abnormal hemostasis. With respect to the coronary arterial vasculature, abnormal thrombus formation due to the rupture of an established atherosclerotic plaque is the major cause of acute myocardial infarction and unstable angina. Both treatment of an occlusive coronary thrombus by thrombolytic therapy and percutaneous transluminal coronary angioplasty (PTCA) are often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterised by the rapid consumption of coagulation factors and systemic coagulation which results in the formation of life-threatening thrombi occurring throughout the vasculature leading to widespread organ failure.

Beyond its direct role in the formation of fibrin rich blood clots, thrombin has been reported to have profound bioregulatory effects on a number of cellular components within the vasculature and blood, (Shuman, M. A., Ann. NY Acad. Sci., 405: 349 (1986)).

A Factor Xa inhibitor may be useful in the treatment of acute vascular diseases such as coronary thrombosis (for example myocardial infarction and unstable angina), thromboembolism, acute vessel closure associated with thrombolytic therapy and percutaneous transluminal coronary angioplasty, transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke. They may also have utility as anti-coagulant agents both in-vivo and ex-vivo, and in oedema and inflammation. Thrombin has been reported to contribute to lung fibroblast proliferation, thus, Factor Xa inhibitors could be useful for the treatment of some pulmonary fibrotic diseases. Factor Xa inhibitors could also be useful in the treatment of tumour metastasis, preventing the fibrin deposition and metastasis caused by the inappropriate activation of Factor Xa by cysteine proteinases produced by certain tumour cells. Thrombin can induce neurite retraction and thus Factor Xa inhibitors may have potential in neurogenerative diseases such as Parkinson's and Alzheimer's disease. They have also been reported for use in conjunction with thrombolytic agents, thus permitting the use of a lower dose of thrombolytic agent.

The present invention provides novel Factor Xa inhibitors. Compounds of the present invention have oral bioavailability and PK profiles suitable for acute and chronic therapies.

SUMMARY OF THE INVENTION

The present invention provides compounds of formula (I):

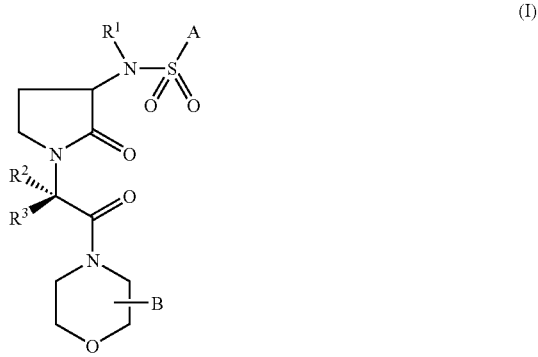

(I)

wherein:

$R^1$ represents hydrogen, —$C_{1-6}$alkyl, —$C_{3-6}$alkenyl, —$C_{2-3}$alkylN$R^b R^c$, —$C_{2-3}$alkylNHCO$R^b$, phenyl or a 5- or 6-membered aromatic heterocyclic group, the phenyl or 5- or 6-membered aromatic heterocyclic group being optionally substituted by halogen, or $R^1$ represents a group X—W, wherein X represents —$C_{1-3}$alkylene- and W represents —CN, —$CO_2$H, —CON$R^b R^c$, —COC$_{1-6}$alkyl, —$CO_2 C_{1-6}$alkyl, phenyl or 5- or 6-membered aromatic or non-aromatic heterocyclic group containing at least one heteroatom selected from O, N or S, the phenyl or aromatic heterocyclic group being optionally substituted by one or more substitutents selected from: —$C_{1-3}$alkyl, —$C_{1-3}$alkoxy, —$C_{1-3}$alkylOH, halogen, —CN, —$CF_3$, —$NH_2$, —$CO_2$H and —OH;

$R^2$ and $R^3$ independently represent hydrogen, —$C_{1-3}$alkyl or —$CF_3$ with the proviso that one of $R^2$ and $R^3$ is —$C_{1-3}$alkyl or —$CF_3$ and the other is hydrogen;

$R^b$ and $R^c$ independently represent hydrogen or —$C_{1-3}$alkyl;

A represents a group selected from:

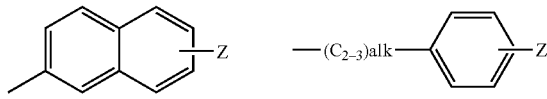

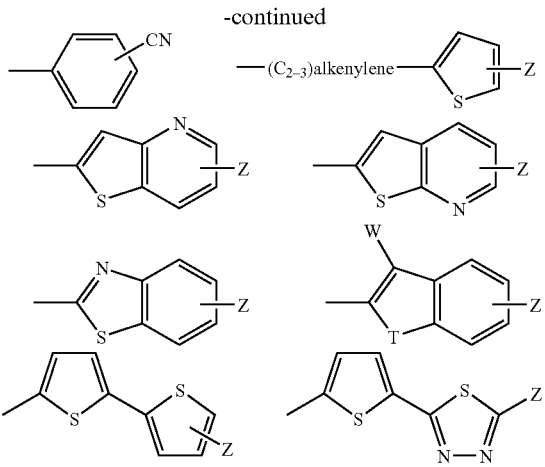

Z represents one or two optional substituents independently selected from halogen and OH, W represents an optional substituent —$C_{1-3}$alkyl, alk represents $C_{2-3}$alkylene or $C_{2-3}$alkenylene, T represents a heteroatom selected from O, S or N;

B represents one or more optional substituents on ring carbon atoms selected from: (i) one or more substituents selected from —$CF_3$, —F, —$CO_2H$, —$C_{1-6}$alkyl, —$C_{1-6}$alkylOH, —($C_{1-3}$alkyl)$NR^bR^c$, —($C_{0-3}$alkyl)$CONR^bR^c$ and —($C_{0-3}$alkyl)$CO_2C_{1-3}$alkyl, —$CONHC_{2-3}$alkylOH, —$CH_2NHC_{2-3}$alkylOH, —$CH_2OC_{1-3}$alkyl and —$CH_2SO_2C_{1-3}$alkyl;

(ii) a group —Y—$R^e$,

Y represents —$C_{1-3}$alkylene-, —CO—, —$C_{1-3}$alkylNH—, —$C_{1-3}$alkylNHCO—, —$C_{1-3}$alkylNHSO_2—, —$CH_2NHSO_2CH_2$— or a direct link, $R^e$ represents phenyl, a 5- or 6-membered cycloalkyl or a 5- or 6-membered heterocycle containing at least one heteroatom selected from O, N or S, each of which is optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH; or (iii) a second ring $R^f$ which is fused to the heterocyclic ring, wherein $R^f$ represents phenyl, a 5- or 6-membered cycloalkyl group or a 5- or 6-membered aromatic heterocyclic group containing at least one heteroatom selected from O, N or S, and the fused bicyclic group is optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;

and pharmaceutically acceptable derivatives thereof.

Further aspects of the invention are:

A pharmaceutical composition comprising a compound of the invention together with a pharmaceutical carrier and/or excipient.

A compound of the invention for use in therapy.

Use of a compound of the invention for the manufacture of a medicament for the treatment of a patient suffering from a condition susceptible to amelioration by a Factor Xa inhibitor.

A method of treating a patient suffering from a condition susceptible to amelioration by a Factor Xa inhibitor comprising administering a therapeutically effective amount of a compound of the invention.

DETAILED DESCRIPTION OF THE INVENTION

The present invention also provides compounds of formula (Ia):

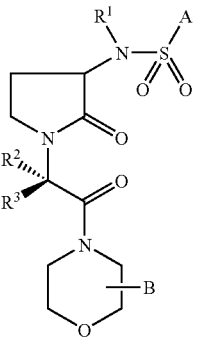

wherein:

$R^1$ represents hydrogen, —$C_{1-6}$alkyl, —$C_{2-6}$alkenyl or a group X—W, wherein X represents —$C_{1-3}$alkylene- and W represents —CN, —$CO_2H$, —$CONR^bR^c$, —$COC_{1-6}$alkyl, —$CO_2C_{1-6}$alkyl, phenyl or 5- or 6-membered aromatic heterocyclic group containing at least one heteroatom selected from O, N or S, the phenyl or aromatic heterocyclic group being optionally substituted by one or more substitutents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;

$R^2$ and $R^3$ independently represent hydrogen, —$C_{1-3}$alkyl or —$CF_3$ with the proviso that when one of $R^2$ and $R^3$ is —$C_{1-3}$alkyl or —$CF_3$, the other is hydrogen;

$R^b$ and $R^c$ independently represent hydrogen or —$C_{1-3}$alkyl;

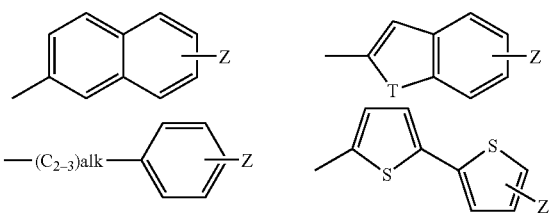

A represents a group selected from:

Z represents an optional substituent halogen, alk represents alkylene or alkenylene, T represents a heteroatom selected from S or N;

B represents one or more optional substituents on ring carbon atoms selected from: (i) one or more substituents selected from —$CF_3$, —F, =O, —$CO_2H$, —$C_{1-6}$alkyl, —$C_{1-6}$alkylOH, —($C_{1-3}$alkyl)$NR^bR^c$, —($C^{0-3}$alkyl) $CONR^bR^c$ and —($C_{0-3}$alkyl)$CO_2C_{1-3}$alkyl;

(ii) a group —Y—$R^e$,

Y represents —$C_{1-3}$alkylene-, —CO—, —$C_{1-3}$alkylNH—, —$C_{1-3}$alkylNHCO—, —$C_{1-3}$alkylNHSO_2—, —$CH_2NHSO_2CH_2$— or a direct link, $R^e$ represents phenyl, a 5- or 6-membered cycloalkyl or a 5- or 6-membered heterocycle containing at least one heteroatom selected from O, N or S, each of which is optionally substituted by one or more substituents selected from: —C$_{1-3}$alkyl, —C$_{1-3}$alkoxy, —C$_{1-3}$alkylOH, halogen, —CN, —CF$_3$, —NH$_2$, —CO$_2$H and —OH; or (iii) a second ring R$^f$ which is fused to the heterocyclic ring, wherein R$^f$ represents phenyl, a 5- or 6-membered cycloalkyl group or a 5- or 6-membered aromatic heterocyclic group containing at least one heteroatom selected from O, N or S, and the fused bicyclic group is optionally substituted by one or more substituents selected from: —C$_{1-3}$alkyl, —C$_{1-3}$alkoxy, —C$_{1-3}$alkylOH, halogen, —CN, —CF$_3$, —NH$_2$, —CO$_2$H and —OH;

and pharmaceutically acceptable salts of solvates thereof.

The compounds of formula (I) and (Ia) contain chiral (asymmetric) centres. The individual stereoisomers (enantiomers and diastereoisomers) and mixtures of these are within the scope of the present invention.

When R$^1$ represents a group X—W:

Preferably, X represents —C$_{1-3}$alkylene-, more preferably -methylene-.

Preferably, W represents —CN, —CO$_2$H, —CONR$^b$R$^c$, —COC$_{1-6}$alkyl, —CO$_2$C$_{1-6}$alkyl or a 5- or 6-membered aromatic heterocyclic group containing at least one heteroatom selected from O, N or S. Preferably, R$^1$ represents hydrogen, —C$_{1-6}$alkyl, —C$_{2-6}$alkenyl or a group X—W wherein X represents —C$_{1-3}$alkylene- and W represents —CN, —CO$_2$H, —CONR$^b$R$^c$, —COC$_{1-6}$alkyl, —CO$_2$C$_{1-6}$alkyl or a 5- or 6-membered aromatic heterocyclic group containing at least one heteroatom selected from O, N or S. More preferably, R$^1$ represents a group selected from hydrogen, —CH$_2$CN, —CH$_2$CONH$_2$, —CH$_2$COC$_{1-6}$alkyl and —CH$_2$CO$_2$C$_{1-6}$alkyl.

In another prefered aspect, R$^1$ represents hydrogen, —C$_{1-6}$alkyl, —C$_{3-6}$alkenyl, —C$_{2-3}$alkylNR$^b$R$^c$, —C$_{2-3}$alkylNHCOR$^b$, phenyl or a 5- or 6-membered aromatic heterocycle, or R$^1$ represents a group X—W wherein X represents —C$_{1-3}$alkylene- and W represents —CN, —CO$_2$H, —CONR$^b$R$^c$, —COC$_{1-6}$alkyl, —CO$_2$C$_{1-6}$alkyl, or a 5- or 6-membered aromatic or non-aromatic heterocyclic group containing at least one heteroatom selected from O, N or S. More preferably, R$^1$ represents hydrogen, —C$_{1-6}$alkyl, —C$_{3-6}$alkenyl, —C$_{2-3}$alkylNR$^b$R$^c$, —C$_{2-3}$alkylNHCOR$^b$, or R$^1$ represents a group X—W wherein X represents —C$_{1-3}$alkylene- and W represents —CN, —CO$_2$H, —CONR$^b$R$^c$, —COC$_{1-6}$alkyl, —CO$_2$C$_{1-6}$alkyl, or a 5- or 6-membered aromatic or non-aromatic heterocyclic group containing at least one heteroatom selected from O, N or S. Even more preferably, R$^1$ represents a group selected from: hydrogen, —C$_{1-6}$alkyl, —CH$_2$CH=CH$_2$, —CH$_2$CH$_2$N(CH$_3$)$_2$, —CH$_2$CH$_2$NHCOCH$_3$, —CH$_2$CN, —CH$_2$CO$_2$H, —CH$_2$CO$_2$CH$_3$, —CH$_2$CO$_2$t-Butyl, —CH$_2$CONH$_2$, —CH$_2$COCH$_2$CH$_3$, —CH$_2$COt-Butyl, —CH$_2$CO$_2$CH$_2$CH$_3$,

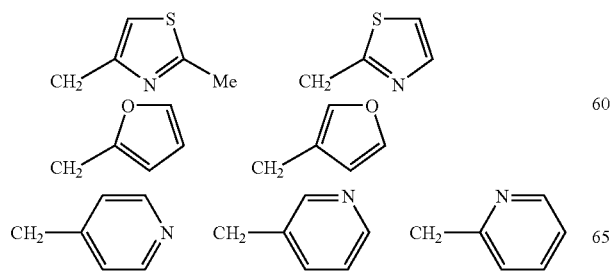

-continued

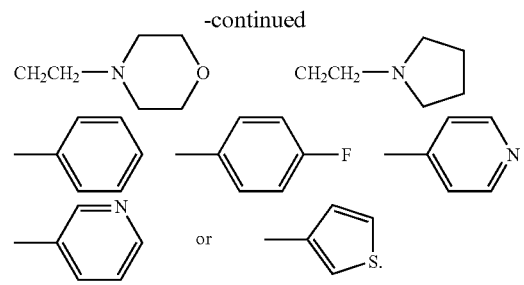

Preferably, R$^2$ represents —C$_{1-3}$alkyl or hydrogen, more preferably methyl or hydrogen.

Preferably, R$^3$ represents —C$_{1-3}$alkyl or hydrogen, more preferably methyl or hydrogen.

Preferably B represents hydrogen or a substituent selected from —C$_{1-6}$alkyl, —(C$_{1-3}$alkyl)NR$^b$R$^c$, —(C$_{0-3}$alkyl)CONR$^b$R$^c$, —CONHC$_{2-3}$alkylOH, —CH$_2$NHC$_{2-3}$alkylOH, —CH$_2$OC$_{1-3}$alkyl and —CH$_2$SO$_2$C$_{1-3}$alkyl or a group —Y—R$^e$ where Y represents —CO— or —CH$_2$— and R$^e$ represents a 5- or 6-membered heterocycle containing at least one heteroatom selected from O, N, S. Preferably, the substitution is in the 2-position relative to the oxygen atom in the morpholine ring. More preferably, B represents hydrogen or a substituent selected from —C$_{1-6}$alkyl, —CONHCH$_3$, —CONHCH$_2$CH(OH)CH$_3$, —CH$_2$NH(CH$_3$)$_2$, —CH$_2$OCH$_3$, —CH$_2$SO$_2$CH$_3$, —CH$_2$NHCH$_2$CH(OH)CH$_3$,

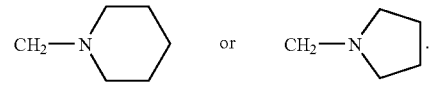

Even more preferably, B represents hydrogen or methyl. Most preferably B represents hydrogen.

Preferably Z represents halogen. More preferably, Z represents chlorine.

Preferably, A represents a substituent selected from:

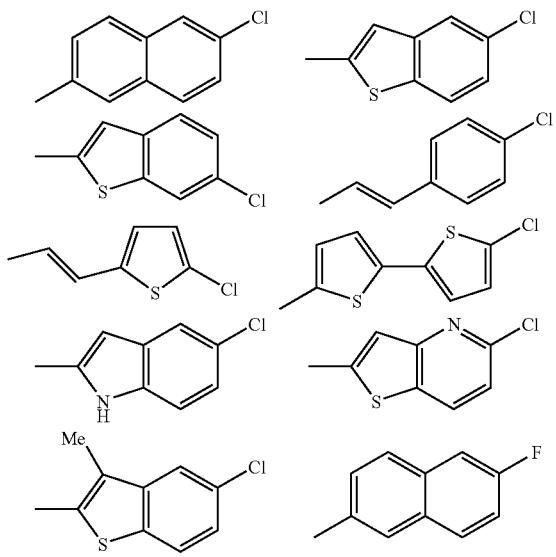

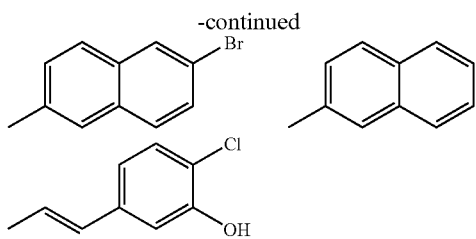

More preferably, A represents a substituent selected from:

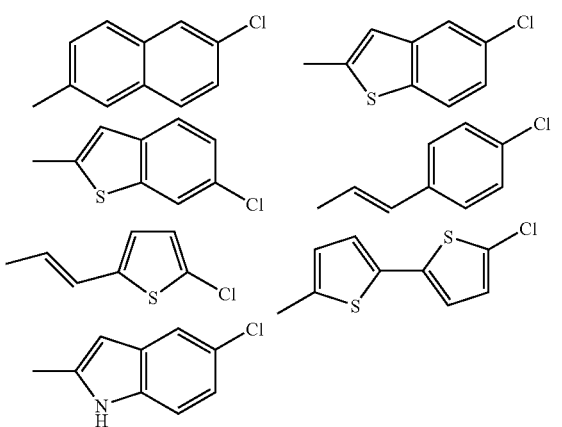

Even more preferably, A represent a substituent selected from:

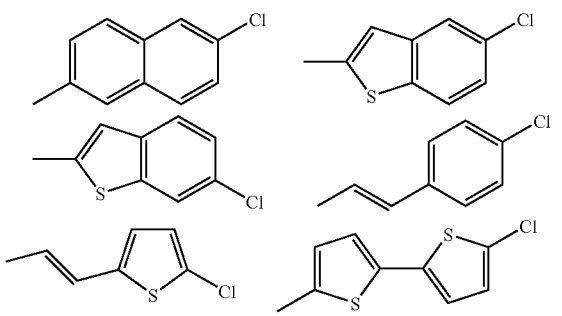

Most preferably, A represents (chlorothienyl)ethene.

In another preferred aspect of the invention, A represents chloronaphthylene, chlorobenzothiophene, chlorobithiophene or chlorophenylethene. More preferably, A represents a group selected from: 6-chloronaphthyl, 5'-chloro-2,2'-biothiophene, (4-chlorophenyl)ethene, 6-chloro-1-benzothiophene.

It is to be understood that the present invention covers all combinations of preferred groups described hereinabove.

Hence, in a preferred aspect the present invention provides compounds of formula (Ia) wherein:

$R^1$ represents hydrogen, —$C_{1-6}$alkyl, —$C_{3-6}$alkenyl, —$C_{2-3}$alkylNR$^b$R$^c$, —$C_{2-3}$alkylNHCOR$^b$, phenyl or a 5- or 6-membered aromatic heterocycle, or a group X—W wherein X represents —$C_{1-3}$alkylene- and W represents —CN, —$CO_2$H, —CONR$^b$R$^c$, —COC$_{1-6}$alkyl, —CO$_2$C$_{1-6}$alkyl, or a 5- or 6-membered aromatic or non-aromatic heterocyclic group containing at least one heteroatom selected from O, N or S;

$R^2$ and $R^3$ independently represent hydrogen or —$C_{1-3}$alkyl with the proviso that one of $R^2$ and $R^3$ is —$C_{1-3}$alkyl and the other is hydrogen;

$R^b$ and $R^c$ independently represent hydrogen or —$C_{1-3}$alkyl;

B represents hydrogen or a substituent selected from —$C_{1-6}$alkyl, —($C_{1-3}$alkyl)NR$^b$R$^c$, —($C_{0-3}$alkyl)CONR$^b$R$^c$, —CONHC$_{2-3}$alkylOH, —CH$_2$NHC$_{2-3}$alkylOH, —CH$_2$OC$_{1-3}$alkyl and —CH$_2$SO$_2$C$_{1-3}$alkyl or a group —Y—R$^e$ where Y represents —CO— or —CH$_2$— and R$^e$ represents a 5- or 6-membered heterocycle containing at least one heteroatom selected from O, N, S.

A represents:

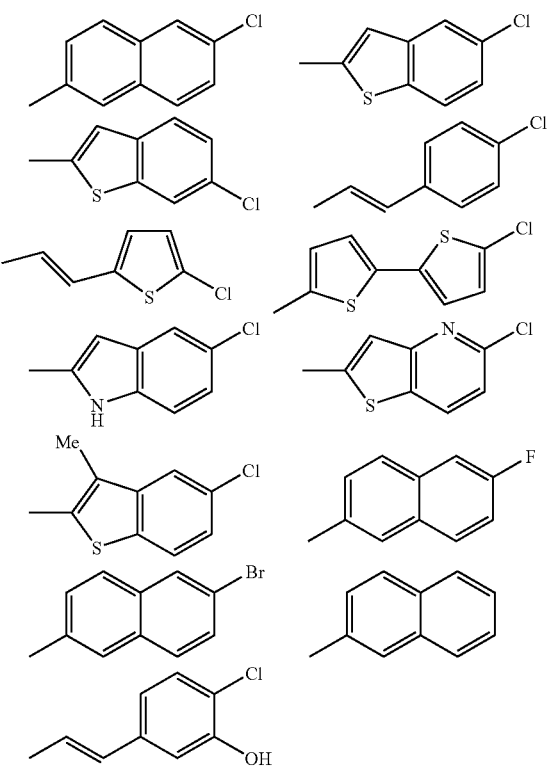

and pharmaceutically acceptable derivatives thereof.

In a more preferred aspect the present invention provides compounds of formula (Ia) wherein:

$R^1$ represents hydrogen, —$C_{1-6}$alkyl, —$C_{3-6}$alkenyl, —$C_{2-3}$alkylNR$^b$R$^c$, —$C_{2-3}$alkylNHCOR$^b$, or a group X—W wherein X represents —$C_{1-3}$alkylene- and W represents —CN, —$CO_2$H, —CONR$^b$R$^c$, —COC$_{1-6}$alkyl, —CO$_2$C$_{1-6}$alkyl, or a 5- or 6-membered aromatic or non-aromatic heterocyclic group containing at least one heteroatom selected from O, N or S;

$R^2$ and $R^3$ independently represent hydrogen or —$C_{1-3}$alkyl with the proviso that one of $R^2$ and $R^3$ is —$C_{1-3}$alkyl and the other is hydrogen;

B represents hydrogen or a substituent selected from —$C_{1-6}$alkyl, —CONHCH$_3$, —CONHCH$_2$CH(OH)CH$_3$, —CH$_2$NH(CH$_3$)$_2$, —CH$_2$OCH$_3$, —CH$_2$SO$_2$CH$_3$, —CH$_2$NHCH$_2$CH(OH)CH$_3$,

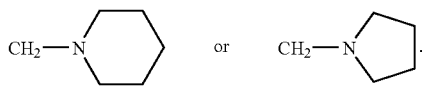

A represents a group selected from:

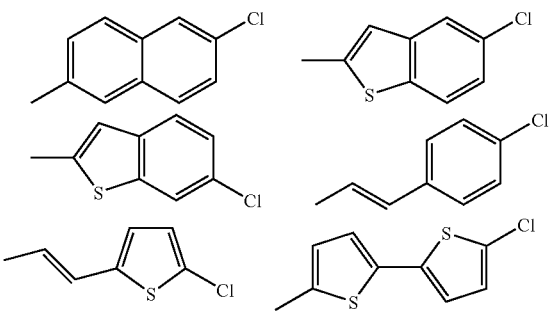

and pharmaceutically acceptable derivatives thereof.

As used herein, the terms "alkyl" and "alkoxy" mean both straight and branched chain saturated hydrocarbon groups. Examples of alkyl groups include methyl (—CH$_3$), ethyl (—C$_2$H$_5$), propyl (—C$_3$H$_7$) and butyl (—C$_4$H$_9$). Examples of alkoxy groups include methoxy (—OCH$_3$) and ethoxy (—OC$_2$H$_5$).

As used herein, the term "alkylene" means both straight and branched chain saturated hydrocarbon linker groups. Examples of alkylene groups include methylene (—CH$_2$—) and ethylene (—CH$_2$CH$_2$—).

As used herein, the term "alkenyl" means both straight and branched chain unsaturated hydrocarbon groups, wherein the unsaturation is present only as double bonds. Examples of alkenyl groups include ethenyl (—CH═CH$_2$) and propenyl (—CH═CHCH$_3$ or —CH$_2$CH═CH$_2$).

As used herein, the term "alkenylene" means both straight and branched chain unsaturated hydrocarbon linker groups, wherein the unsaturation is present only as double bonds. Examples of alkenylene groups includes ethenylene (—CH═CH—) and propenylene (—CH$_2$—CH═CH— or —CH═CH—CH$_2$—).

As used herein, the term "alkynyl" means both straight and branched chain unsaturated hydrocarbon groups, wherein the unsaturation is present only as triple bonds. Examples of alkynyl groups include propynyl (e.g. —CH$_2$—C≡CH).

As used herein, the term "halogen" means fluorine, chlorine, bromine and iodine.

As used herein, the term "cycloalkyl group" means an aliphatic ring (saturated carbocyclic ring). Examples of cycloalkyl groups include cyclopentyl and cyclohexyl.

As used herein, the term "heterocyclic group" means a ring containing one or more heteroatoms selected from: nitrogen, sulphur and oxygen atoms. The heterocycle may be aromatic or non-aromatic, i.e., may be saturated, partially or fully unsaturated.

Examples of 5-membered groups include thienyl, pyrrolyl, pyrrolidinyl, pyrazolyl, imidazolyl, triazolyl, tetrazolyl, thiazolyl, thiadiazolyl, oxazolyl, oxadiazolyl, isoxazolyl and furanyl, 6-membered groups include pyridyl, pyrazyl and pyrimidyl, morpholinyl, thiomorpholinyl, 7-membered groups include azepinyl.

As used herein, the term "pharmaceutically acceptable" means a compound which is suitable for pharmaceutical use.

As used herein, the term "pharmaceutically acceptable derivative", means any pharmaceutically acceptable salt, solvate, or prodrug e.g. ester or carbamate, or salt or solvate of such a prodrug, of a compound of formula (I) or (Ia), which upon administration to the recipient is capable of providing (directly or indirectly) a compound of formula (I) or (Ia), or an active metabolite or residue thereof. Preferred pharmaceutically acceptable derivatives are salts and solvates.

Suitable salts according to the invention include those formed with both organic and inorganic acids and bases. Pharmaceutically acceptable acid addition salts include those formed from mineral acids such as: hydrochloric, hydrobromic, sulphuric, phosphoric, acid; and organic acids such as: citric, tartaric, lactic, pyruvic, acetic, trifluoroacetic, succinic, oxalic, formic, fumaric, maleic, oxaloacetic, methanesulphonic, ethanesulphonic, p-toluenesulphonic, benzenesulphonic and isethionic acids. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine. Particularly preferred pharmaceutically acceptable salts include those formed from hydrochloric, trifluoroacetic and formic acids.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of formula (I) or (Ia) are within the scope of the invention.

Salts and solvates of compounds of formula (I) or (Ia) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formula (I) or (Ia) and their pharmaceutically acceptable salts and solvates.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. Esters may be active in their own right and/or be hydrolysable under in vivo conditions in the human body. Suitable pharmaceutically acceptable in vivo hydrolysable ester groups include those which break down readily in the human body to leave the parent acid or its salt.

Preferred compounds of the invention include:

6-Chloro-N-{(3S)-1-[(1S)-1-methyl-2-morpholin-4-yl-2-oxoethyl]-2-oxopyrrolidin-3-yl}naphthalene-2-sulfonamide, 6-Chloro-N-{(3S)-1-[(1S)-2-(2,6-dimethylmorpholin-4-yl)-1-methyl-2-oxoethyl]-2-oxopyrrolidin-3-yl}naphthalene-2-sulfonamide, 6-Chloro-N-{(3S)-1-[(1S)-1-methyl-2-(3-methylmorpholin-4-yl)-2-oxoethyl]-2-oxopyrrolidin-3-yl}naphthalene-2-sulfonamide, 6-Chloro-N-((3S)-1-{(1S)-1-methyl-2-oxo-2-[3-(pyrrolidin-1-ylcarbonyl)morpholin-4-yl]ethyl}-2-oxopyrrolidin-3-yl)naphthalene-2-sulfonamide, 6-Chloro-N-[(3S)-1-((1S)-1-methyl-2-{2-[(methylsulfonyl)methyl]morpholin-4-yl}-2-oxoethyl)-2-oxopyrrolidin-3-yl]naphthalene-2-sulfonamide, 6-Chloro-N-((3S)-1-{(1S)-2-[2-(methoxymethlyl)morpholin-4-yl]-1-methyl-2-oxoethyl}-2-oxopyrrolidin-3-yl)naphthalene-2-sulfonamide, 4-[(2S)-2-((3S)-3-{[(6-Chloro-2-naphthyl)sulfonyl]amino}-2-oxopyrrolidin-1-yl)propanoyl]-N-methylmorpholine-2-carboxamide, 6-Chloro-N-((3S)-1-{(1S)-1-methyl-2-oxo-2-[2-(pyrrolidin-1-ylcarbonyl)morpholin-4-yl]ethyl}-2-oxopyrrolidin-3-yl)naphthalene-2-sulfonamide, 4-[(2S)-2-((3S)-3-{[(6-Chloro-2-naphthyl)sulfonyl]amino}-2-oxopyrrolidin-1-yl)propanoyl]-N,N-dimethylmorpholine-2-carboxamide, 4-[(2S)-2-((3S)-3-{[(6-Chloro-2-naphthyl)sulfonyl]amino}-2-oxopyrrolidin-1-yl)propanoyl]-N-(2-hydroxypropyl)morpholine-2-carboxamide, 4-[(2S)-2-((3S)-3-{[(6-Chloro-2-naphthyl)sulfonyl]amino}-2-oxopyrrolidin-1-yl)propanoyl]-N,N-diisopropylmorpholine-2-carboxamide, 6-Chloro-N-((3S)-1-{(1S)-1-methyl-2-oxo-2-[2-(piperidin-1-ylcarbonyl)morpholin-4-yl]ethyl}-2-oxopyrrolidin-3-yl)naphthalene-2-sulfonamide, 6-Chloro-N-[(3S)-1-((1S)-1-methyl-2-{2-[(methylamino)methyl]morpholin-4-yl}-2-oxoethyl)-2-oxopyrrolidin-3-yl]naphthalene-2-sulfonamide formate, 6-Chloro-N-((3S)-1-{(1S)-1-methyl-2-oxo-2-[2-(pyrrolidin-1-ylmethyl)morpholin-4-yl]ethyl}-2-oxopyrrolidin-3-yl)naphthalene-2-sulfonamide formate, 6-Chloro-N-{(3S)-1-[(1S)-2-(2-{[(2-hydroxypropyl)amino]methyl}morpholin-4-yl)-1-methyl-2-oxoethyl]-2-oxopyrrolidin-3-yl}naphthalene-2-sulfonamide formate, 6-Chloro-N-[(3S)-1-((1S)-2-{2-[(dimethylamino)methyl]morpholin-4-yl}-1-methyl-2-oxoethyl)-2-oxopyrrolidin-3-yl]naphthalene-2-sulfonamide formate, 6-Chloro-N-[(3S)-1-((1S)-2-{2-[(diisopropylamino)methyl]morpholin-4-yl}-1-methyl-2-oxoethyl)-2-oxopyrrolidin-3-yl]naphthalene-2-sulfonamide formate, 6-Chloro-N-((3S)-1-{(1S)-1-methyl-2-oxo-2-[2-(piperidin-1-ylmethyl)morpholin-4-yl]ethyl}-2-oxopyrrolidin-3-yl)naphthalene-2-sulfonamide formate, 6-Chloro-N-((3S)-1-{(1S)-2-[(2R,6S)-2,6-dimethylmorpholin-4-yl]-1-methyl-2-oxoethyl}-2-oxopyrrolidin-3-yl)naphthalene-2-sulfonamide, 6-Chloro-N-{(3R)-1-[(1S)-1-methyl-2-morpholin-4-yl-2-oxoethyl]-2-oxopyrrolidin-3-yl}naphthalene-2-sulfonamide, 5'-Chloro-N-{(3S)-1-[(1S)-1-methyl-2-morpholin-4-yl-2-oxoethyl]-2-oxopyrrolidin-3-yl}-2,2'-bithiophene-5-sulfonamide, (E)-2-(4-Chlorophenyl)-N-{(3S)-1-[(1S)-1-methyl-2-morpholin-4-yl-2-oxoethyl]-2-oxopyrrolidin-3-yl}ethenesulfonamide, N2-{[(E)-2-(4-Chlorophenyl)ethenyl]sulfonyl}-N2-{(3S)-1-[(1S)-1-methyl-2-morpholin-4-yl-2-oxoethyl]-2-oxopyrrolidin-3-yl}glycinamide, N2-[(5'-Chloro-2,2'-bithien-5-yl)sulfonyl]-N2-{(3S)-1-[(1S)-1-methyl-2-morpholin-4-yl-2-oxoethyl]-2-oxopyrrolidin-3-yl}glycinamide, 5'-Chloro-N-(cyanomethyl)-N-{(3S)-1-[(1S)-1-methyl-2-morpholin-4-yl-2-oxoethyl]-2-oxopyrrolidin-3-yl}-2,2'-bithiophene-5-sulfonamide, Methyl N-[(5'-chloro-2,2'-bithien-5-yl)sulfonyl]-N-{(3S)-1-[(1S)-1-methyl-2-morpholin-4-yl-2-oxoethyl]-2-oxopyrrolidin-3-yl}glycinate, 5'-Chloro-N-{(3S)-1-[(1S)-1-methyl-2-morpholin-4-yl-2-oxoethyl]-2-oxopyrrolidin-3-yl}-N-(2-oxobutyl)-2,2'-bithiophene-5-sulfonamide, N-[(5'-Chloro-2,2'-bithien-5-yl)sulfonyl]-N-{(3S)-1-[(1S)-1-methyl-2-morpholin-4-yl-2-oxoethyl]-2-oxopyrrolidin-3-yl}glycine, (E)-2-(4-Chlorophenyl)-N-(cyanomethyl)-N-{(3S)-1-[(1S)-1-methyl-2-morpholin-4-yl-2-oxoethyl]-2-oxopyrrolidin-3-yl}ethenesulfonamide, (E)-2-(4-Chlorophenyl)-N-{(3S)-1-[(1S)-1-methyl-2-morpholin-4-yl-2-oxoethyl]-2-oxopyrrolidin-3-yl}-N-(2-oxobutyl)ethenesulfonamide, Methyl N-{[(E)-2-(4-chlorophenyl)ethenyl]sulfonyl}-N-{(3S)-1-[(1S)-1-methyl-2-morpholin-4-yl-2-oxoethyl]-2-oxopyrrolidin-3-yl}glycinate, N-{[(E)-2-(4-Chlorophenyl)ethenyl]sulfonyl}-N-{(3S)-1-[(1S)-1-methyl-2-morpholin-4-yl-2-oxoethyl]-2-oxopyrrolidin-3-yl}glycine, 6-Chloro-N-(3-furylmethyl)-N-{(3S)-1-[(1S)-1-methyl-2-morpholin-4-yl-2-oxoethyl]-2-oxopyrrolidin-3-yl}naphthalene-2-sulfonamide, 6-Chloro-N-{(3S)-1-[(1S)-1-methyl-2-morpholin-4-yl-2-oxoethyl]-2-oxopyrrolidin-3-yl}-N-(pyridin-3-ylmethyl)naphthalene-2-sulfonamide formate, 6-Chloro-N-ethyl-N-{(3S)-1-[(1S)-1-methyl-2-morpholin-4-yl-2-oxoethyl]-2-oxopyrrolidin-3-yl}naphthalene-2-sulfonamide, 6-Chloro-N-{(3S)-1-[(1S)-1-methyl-2-morpholin-4-yl-2-oxoethyl]-2-oxopyrrolidin-3-yl}-N-(2-oxobutyl)naphthalene-2-sulfonamide, N-2-[(6-Chloro-2-naphthyl)sulfonyl]-N-2-{(3S)-1-[(1S)-1-methyl-2-morpholin-4-yl-2-oxoethyl]-2-oxopyrrolidin-3-yl}glycinamide, 6-Chloro-N-(2-furylmethyl)-N-{(3S)-1-[(1S)-1-methyl-2-morpholin-4-yl-2-oxoethyl]-2-oxopyrrolidin-3-yl}naphthalene-2-sulfonamide, 6-Chloro-N-{(3S)-1-[(1S)-1-methyl-2-morpholin-4-yl-2-oxoethyl]-2-oxopyrrolidin-3-yl}-N-(1,3-thiazol-2-ylmethyl)naphthalene-2-sulfonamide, N2-[(6-Chloro-2-naphthyl)sulfonyl]-N2-((3S)-1-{(1S)-2-[(2R,6S)-2,6-dimethylmorpholin-4-yl]-1-methyl-2-oxoethyl}-2-oxopyrrolidin-3-yl)glycinamide, 6-Chloro-N-{(3S)-1-[(1S)-1-methyl-2-morpholin-4-yl-2-oxoethyl]-2-oxopyrrolidin-3-yl}-N-[(2-methyl-1,3-thiazol-4-yl)methyl]naphthalene-2-sulfonamide, 6-Chloro-N-{(3S)-1-[(1S)-1-methyl-2-morpholin-4-yl-2-oxoethyl]-2-oxopyrrolidin-3-yl}-N-(pyridin-2-ylmethyl)naphthalene-2-sulfonamide formate, 6-Chloro-N-{(3S)-1-[(1S)-1-methyl-2-morpholin-4-yl-2-oxoethyl]-2-oxopyrrolidin-3-yl}-N-(pyridin-4-ylmethyl)naphthalene-2-sulfonamide formate, 6-Chloro-N-{(3S)-1-[(1R)-1-methyl-2-morpholin-4-yl-2-oxoethyl]-2-oxopyrrolidin-3-yl}naphthalene-2-sulfonamide, 6-Chloro-N-methyl-N-{(3S)-1-[(1R)-1-methyl-2-morpholin-4-yl-2-oxoethyl]-2-oxopyrrolidin-3-yl}naphthalene-2-sulfonamide, 6-Chloro-N-(cyanomethyl)-N-{(3S)-1-[(1S)-1-methyl-2-morpholin-4-yl-2-oxoethyl]-2-oxopyrrolidin-3-yl}naphthalene-2-sulfonamide, 6-Chloro-N-methyl-N-{(3S)-1-[(1S)-1-methyl-2-morpholin-4-yl-2-oxoethyl]-2-oxopyrrolidin-3-yl}naphthalene-2-sulfonamide,
6-Chloro-N-(3,3-dimethyl-2-oxobutyl)-N-{(3S)-1-[(1S)-1-methyl-2-morpholin-4-yl-2-oxoethyl]-2-oxopyrrolidin-3-yl}naphthalene-2-sulfonamide,
N2-[(6-Chloro-2-naphthyl)sulfonyl]-N1-methyl-N2-{(3S)-1-[(1S)-1-methyl-2-morpholin-4-yl-2-oxoethyl]-2-oxopyrrolidin-3-yl}glycinamide,
N-Allyl-6-chloro-N-{(3S)-1-[(1S)-1-methyl-2-morpholin-4-yl-2-oxoethyl]-2-oxopyrrolidin-3-yl}naphthalene-2-sulfonamide,
Methyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate,
Ethyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate,
tert-Butyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate,
N-[(6-Chloro-2-naphthyl)sulfonyl]-N-{(3S)-1-[(1S)-1-methyl-2-morpholin-4-yl-2-oxoethyl]-2-oxopyrrolidin-3-yl}glycine,
6-Chloro-N-{(3R)-1-[(1R)-1-methyl-2-morpholin-4-yl-2-oxoethyl]-2-oxopyrrolidin-3-yl}naphthalene-2-sulfonamide,
5-Chloro-N-{(3S)-1-[(1S)-1-methyl-2-morpholin-4-yl-2-oxoethyl]-2-oxopyrrolidin-3-yl}-1-benzofuran-2-sulfonamide,
(E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide,
5-Chloro-N-{(3S)-1-[(1S)-1-methyl-2-morpholin-4-yl-2-oxoethyl]-2-oxopyrrolidin-3-yl}-1-benzothiophene-2-sulfonamide,
6-Chloro-N-{(3S)-1-[(1S)-1-methyl-2-morpholin-4-yl-2-oxoethyl]-2-oxopyrrolidin-3-yl}-1-benzothiophene-2-sulfonamide,
5-Chloro-3-methyl-N-{(3S)-1-[(1S)-1-methyl-2-morpholin-4-yl-2-oxoethyl]-2-oxopyrrolidin-3-yl}-1-benzothiophene-2-sulfonamide,
3-Cyano-N-{(3S)-1-[(1S)-1-methyl-2-morpholin-4-yl-2-oxoethyl]-2-oxopyrrolidin-3-yl}benzenesulfonamide,
4-Cyano-N-{(3S)-1-[(1S)-1-methyl-2-morpholin-4-yl-2-oxoethyl]-2-oxopyrrolidin-3-yl}benzenesulfonamide,
5-(5-Chloro-1,3,4-thiadiazol-2-yl)-N-{(3S)-1-[(1S)-1-methyl-2-morpholin-4-yl-2-oxoethyl]-2-oxopyrrolidin-3-yl}thiophene-2-sulfonamide,
5-Chloro-N-{(3S)-1-[(1S)-1-methyl-2-morpholin-4-yl-2-oxoethyl]-2-oxopyrrolidin-3-yl}thieno[2,3-b]pyridine-2-sulfonamide,
5-Chloro-N-{(3S)-1-[(1S)-1-methyl-2-morpholin-4-yl-2-oxoethyl]-2-oxopyrrolidin-3-yl}thieno[3,2-b]pyridine-2-sulfonamide,
6-Chloro-N-{(3S)-1-[(1S)-1-methyl-2-morpholin-4-yl-2-oxoethyl]-2-oxopyrrolidin-3-yl}-N-(2-oxobutyl)-1-benzothiophene-2-sulfonamide,
N2-[(6-Chloro-1-benzothien-2-yl)sulfonyl]-N2-{(3S)-1-[(1S)-1-methyl-2-morpholin-4-yl-2-oxoethyl]-2-oxopyrrolidin-3-yl}glycinamide,
5-Chloro-N-{(3S)-1-[(1S)-1-methyl-2-morpholin-4-yl-2-oxoethyl]-2-oxopyrrolidin-3-yl}-N-(2-oxobutyl)-1-benzothiophene-2-sulfonamide,
N2-[(5-Chloro-1-benzothien-2-yl)sulfonyl]-N2-{(3S)-1-[(1S)-1-methyl-2-morpholin-4-yl-2-oxoethyl]-2-oxopyrrolidin-3-yl}glycinamide,
6-Chloro-N-{(3S)-1-[(1S)-1-methyl-2-morpholin-4-yl-2-oxoethyl]-2-oxopyrrolidin-3-yl}-N-phenylnaphthalene-2-sulfonamide,
6-Chloro-N-(4-fluorophenyl)-N-{(3S)-1-[(1S)-1-methyl-2-morpholin-4-yl-2-oxoethyl]-2-oxopyrrolidin-3-yl}naphthalene-2-sulfonamide,
6-Chloro-N-{(3S)-1-[(1S)-1-methyl-2-morpholin-4-yl-2-oxoethyl]-2-oxopyrrolidin-3-yl}-N-pyridin-4-ylnaphthalene-2-sulfonamide,
6-Chloro-N-{(3S)-1-[(1S)-1-methyl-2-morpholin-4-yl-2-oxoethyl]-2-oxopyrrolidin-3-yl}-N-pyridin-3-ylnaphthalene-2-sulfonamide,
6-Chloro-N-{(3S)-1-[(1S)-1-methyl-2-morpholin-4-yl-2-oxoethyl]-2-oxopyrrolidin-3-yl}-N-thien-3-ylnaphthalene-2-sulfonamide,
N2-[(6-Chloro-2-naphthyl)sulfonyl]-N2-((3S)-1-{(1S)-2-[(2R,6S)-2,6-dimethylmorpholin-4-yl]-1-methyl-2-oxoethyl}-2-oxopyrrolidin-3-yl)glycinamide,
(E)-2-(3-Chloro-4-hydroxyphenyl)-N-{(3S)-1-[(1S)-1-methyl-2-morpholin-4-yl-2-oxoethyl]-2-oxopyrrolidin-3-yl}ethenesulfonamide,
(E)-2-(4-Chloro-3-hydroxyphenyl)-N-{(3S)-1-[(1S)-1-methyl-2-morpholin-4-yl-2-oxoethyl]-2-oxopyrrolidin-3-yl}ethenesulfonamide,
6-Chloro-N-{(3S)-1-[(1S)-1-methyl-2-morpholin-4-yl-2-oxoethyl]-2-oxopyrrolidin-3-yl}-N-(2-morpholin-4-ylethyl)naphthalene-2-sulfonamide formate,
6-Chloro-N-{(3S)-1-[(1S)-1-methyl-2-morpholin-4-yl-2-oxoethyl]-2-oxopyrrolidin-3-yl}-N-(2-pyrrolidin-1-ylethyl)naphthalene-2-sulfonamide formate,
6-Chloro-N-[2-(dimethylamino)ethyl]-N-{(3S)-1-[(1S)-1-methyl-2-morpholin-4-yl-2-oxoethyl]-2-oxopyrrolidin-3-yl}naphthalene-2-sulfonamide formate,
N-[2-([(6-Chloro-2-naphthyl)sulfonyl]{(3S)-1-[(1S)-1-methyl-2-morpholin-4-yl-2-oxoethyl]-2-oxopyrrolidin-3-yl}amino)ethyl]acetamide,
5-Chloro-N-{(3S)-1-[(1S)-1-methyl-2-morpholin-4-yl-2-oxoethyl]-2-oxopyrrolidin-3-yl}-1H-indole-2-sulfonamide,
6-Chloro-N-{(3S)-1-[(1S)-1-methyl-2-morpholin-4-yl-2-oxoethyl]-2-oxopyrrolidin-3-yl}-1,3-benzothiazole-2-sulfonamide,
6-Chloro-N-{(3S)-1-[(1S)-1-methyl-2-(2-methylmorpholin-4-yl)-2-oxoethyl]-2-oxopyrrolidin-3-yl}naphthalene-2-sulfonamide,
(E)-2-(5-Chlorothien-2-yl)-N-methyl-N-{(3S)-1-[(1S)-1-methyl-2-morpholin-4-yl-2-oxoethyl]-2-oxopyrrolidin-3-yl}ethenesulfonamide, and
(E)-2-(5-Chlorothien-2-yl)-N-methyl-N-{(3S)-1-[(1S)-1-methyl-2-morpholin-4-yl-2-oxoethyl]-2-oxopyrrolidin-3-yl}ethenesulfonamide.
More preferred compounds of the invention include:
6-Chloro-N-{(3S)-1-[(1S)-1-methyl-2-morpholin-4-yl-2-oxoethyl]-2-oxopyrrolidin-3-yl}naphthalene-2-sulfonamide,
6-Chloro-N-{(3S)-1-[(1S)-2-(2,6-dimethylmorpholin-4-yl)-1-methyl-2-oxoethyl]-2-oxopyrrolidin-3-yl}naphthalene-2-sulfonamide,
6-Chloro-N-{(3S)-1-[(1S)-1-methyl-2-(3-methylmorpholin-4-yl)-2-oxoethyl]-2-oxopyrrolidin-3-yl}naphthalene-2-sulfonamide,
6-Chloro-N-[(3S)-1-((1S)-1-methyl-2-{2-[(methylsulfonyl)methyl]morpholin-4-yl}-2-oxoethyl)-2-oxopyrrolidin-3-yl]naphthalene-2-sulfonamide,
6-Chloro-N-((3S)-1-{(1S)-2-[2-(methoxymethyl)morpholin-4-yl]-1-methyl-2-oxoethyl}-2-oxopyrrolidin-3-yl)naphthalene-2-sulfonamide, 4-[(2S)-2-((3S)-3-{[(6-Chloro-2-naphthyl)sulfonyl]amino}-2-oxopyrrolidin-1-yl)propanoyl]-N-methylmorpholine-2-carboxamide, 4-[(2S)-2-((3S)-3-{[(6-Chloro-2-naphthyl)sulfonyl]amino}-2-oxopyrrolidin-1-yl)propanoyl]-N-(2-hydroxypropyl)morpholine-2-carboxamide, 6-Chloro-N-((3S)-1-{(1S)-1-methyl-2-oxo-2-[2-(pyrrolidin-1-ylmethyl)morpholin-4-yl]ethyl}-2-oxopyrrolidin-3-yl)naphthalene-2-sulfonamide formate, 6-Chloro-N-{(3S)-1-[(1S)-2-(2-{[(2-hydroxypropyl)amino]methyl}morpholin-4-yl)-1-methyl-2-oxoethyl]-2-oxopyrrolidin-3-yl}naphthalene-2-sulfonamide formate, 6-Chloro-N-[(3S)-1-((1S)-2-{2-[(dimethylamino)methyl]morpholin-4-yl}-1-methyl-2-oxoethyl)-2-oxopyrrolidin-3-yl]naphthalene-2-sulfonamide formate, 6-Chloro-N-((3S)-1-{(1S)-1-methyl-2-oxo-2-[2-(piperidin-1-ylmethyl)morpholin-4-yl]ethyl}-2-oxopyrrolidin-3-yl)naphthalene-2-sulfonamide formate, 6-Chloro-N-((3S)-1-{(1S)-2-[(2R,6S)-2,6-dimethylmorpholin-4-yl]-1-methyl-2-oxoethyl}-2-oxopyrrolidin-3-yl)naphthalene-2-sulfonamide, 6-Chloro-N-{(3R)-1-[(1S)-1-methyl-2-morpholin-4-yl-2-oxoethyl]-2-oxopyrrolidin-3-yl}naphthalene-2-sulfonamide, 5'-Chloro-N-{(3S)-1-[(1S)-1-methyl-2-morpholin-4-yl-2-oxoethyl]-2-oxopyrrolidin-3-yl}-2,2'-bithiophene-5-sulfonamide, (E)-2-(4-Chlorophenyl)-N-{(3S)-1-[(1S)-1-methyl-2-morpholin-4-yl-2-oxoethyl]-2-oxopyrrolidin-3-yl}ethenesulfonamide, N2-{[(E)-2-(4-Chlorophenyl)ethenyl]sulfonyl}-N2-{(3S)-1-[(1S)-1-methyl-2-morpholin-4-yl-2-oxoethyl]-2-oxopyrrolidin-3-yl}glycinamide, N2-[(5'-Chloro-2,2'-bithien-5-yl)sulfonyl]-N2-{(3S)-1-[(1S)-1-methyl-2-morpholin-4-yl-2-oxoethyl]-2-oxopyrrolidin-3-yl}glycinamide, 5'-Chloro-N-(cyanomethyl)-N-{(3S)-1-[(1S)-1-methyl-2-morpholin-4-yl-2-oxoethyl]-2-oxopyrrolidin-3-yl}-2,2'-bithiophene-5-sulfonamide, Methyl N-[(5'-chloro-2,2'-bithien-5-yl)sulfonyl]-N-{(3S)-1-[(1S)-1-methyl-2-morpholin-4-yl-2-oxoethyl]-2-oxopyrrolidin-3-yl}glycinate, 5'-Chloro-N-{(3S)-1-[(1S)-1-methyl-2-morpholin-4-yl-2-oxoethyl]-2-oxopyrrolidin-3-yl}-N-(2-oxobutyl)-2,2'-bithiophene-5-sulfonamide, N-[(5'-Chloro-2,2'-bithien-5-yl)sulfonyl]-N-{(3S)-1-[(1S)-1-methyl-2-morpholin-4-yl-2-oxoethyl]-2-oxopyrrolidin-3-yl}glycine, (E)-2-(4-Chlorophenyl)-N-(cyanomethyl)-N-{(3S)-1-[(1S)-1-methyl-2-morpholin-4-yl-2-oxoethyl]-2-oxopyrrolidin-3-yl}ethenesulfonamide, (E)-2-(4-Chlorophenyl)-N-{(3S)-1-[(1S)-1-methyl-2-morpholin-4-yl-2-oxoethyl]-2-oxopyrrolidin-3-yl}-N-(2-oxobutyl)ethenesulfonamide, Methyl N-{[(E)-2-(4-chlorophenyl)ethenyl]sulfonyl}-N-{(3S)-1-[(1S)-1-methyl-2-morpholin-4-yl-2-oxoethyl]-2-oxopyrrolidin-3-yl}glycinate, N-{[(E)-2-(4-Chlorophenyl)ethenyl]sulfonyl}-N-{(3S)-1-[(1S)-1-methyl-2-morpholin-4-yl-2-oxoethyl]-2-oxopyrrolidin-3-yl}glycine, 6-Chloro-N-(3-furylmethyl)-N-{(3S)-1-[(1S)-1-methyl-2-morpholin-4-yl-2-oxoethyl]-2-oxopyrrolidin-3-yl}naphthalene-2-sulfonamide, 6-Chloro-N-{(3S)-1-[(1S)-1-methyl-2-morpholin-4-yl-2-oxoethyl]-2-oxopyrrolidin-3-yl}-N-(pyridin-3-ylmethyl)naphthalene-2-sulfonamide formate, 6-Chloro-N-ethyl-N-{(3S)-1-[(1S)-1-methyl-2-morpholin-4-yl-2-oxoethyl]-2-oxopyrrolidin-3-yl}naphthalene-2-sulfonamide, 6-Chloro-N-{(3S)-1-[(1S)-1-methyl-2-morpholin-4-yl-2-oxoethyl]-2-oxopyrrolidin-3-yl}-N-(2-oxobutyl)naphthalene-2-sulfonamide, N-2-[(6-Chloro-2-naphthyl)sulfonyl]-N-2-{(3S)-1-[(1S)-1-methyl-2-morpholin-4-yl-2-oxoethyl]-2-oxopyrrolidin-3-yl}glycinamide, 6-Chloro-N-(2-furylmethyl)-N-{(3S)-1-[(1S)-1-methyl-2-morpholin-4-yl-2-oxoethyl]-2-oxopyrrolidin-3-yl}naphthalene-2-sulfonamide, 6-Chloro-N-{(3S)-1-[(1S)-1-methyl-2-morpholin-4-yl-2-oxoethyl]-2-oxopyrrolidin-3-yl}-N-(1,3-thiazol-2-ylmethyl)naphthalene-2-sulfonamide, N2-[(6-Chloro-2-naphthyl)sulfonyl]-N2-((3S)-1-{(1S)-2-[(2R,6S)-2,6-dimethylmorpholin-4-yl]-1-methyl-2-oxoethyl}-2-oxopyrrolidin-3-yl)glycinamide, 6-Chloro-N-{(3S)-1-[(1S)-1-methyl-2-morpholin-4-yl-2-oxoethyl]-2-oxopyrrolidin-3-yl}-N-[(2-methyl-1,3-thiazol-4-yl)methyl]naphthalene-2-sulfonamide, 6-Chloro-N-{(3S)-1-[(1S)-1-methyl-2-morpholin-4-yl-2-oxoethyl]-2-oxopyrrolidin-3-yl}-N-(pyridin-2-ylmethyl)naphthalene-2-sulfonamide formate, 6-Chloro-N-{(3S)-1-[(1S)-1-methyl-2-morpholin-4-yl-2-oxoethyl]-2-oxopyrrolidin-3-yl}-N-(pyridin-4-ylmethyl)naphthalene-2-sulfonamide formate, 6-Chloro-N-{(3S)-1-[(1R)-1-methyl-2-morpholin-4-yl-2-oxoethyl]-2-oxopyrrolidin-3-yl}naphthalene-2-sulfonamide, 6-Chloro-N-methyl-N-{(3S)-1-[(1R)-1-methyl-2-morpholin-4-yl-2-oxoethyl]-2-oxopyrrolidin-3-yl}naphthalene-2-sulfonamide, 6-Chloro-N-(cyanomethyl)-N-{(3S)-1-[(1S)-1-methyl-2-morpholin-4-yl-2-oxoethyl]-2-oxopyrrolidin-3-yl}naphthalene-2-sulfonamide, 6-Chloro-N-methyl-N-{(3S)-1-[(1S)-1-methyl-2-morpholin-4-yl-2-oxoethyl]-2-oxopyrrolidin-3-yl}naphthalene-2-sulfonamide, 6-Chloro-N-(3,3-dimethyl-2-oxobutyl)-N-{(3S)-1-[(1S)-1-methyl-2-morpholin-4-yl-2-oxoethyl]-2-oxopyrrolidin-3-yl}naphthalene-2-sulfonamide, N2-[(6-Chloro-2-naphthyl)sulfonyl]-N1-methyl-N2-{(3S)-1-[(1S)-1-methyl-2-morpholin-4-yl-2-oxoethyl]-2-oxopyrrolidin-3-yl}glycinamide, N-Allyl-6-chloro-N-{(3S)-1-[(1S)-1-methyl-2-morpholin-4-yl-2-oxoethyl]-2-oxopyrrolidin-3-yl}naphthalene-2-sulfonamide, Methyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate, Ethyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate, tert-Butyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate, N-[(6-Chloro-2-naphthyl)sulfonyl]-N-{(3S)-1-[(1S)-1-methyl-2-morpholin-4-yl-2-oxoethyl]-2-oxopyrrolidin-3-yl}glycine, 6-Chloro-N-{(3R)-1-[(1R)-1-methyl-2-morpholin-4-yl-2-oxoethyl]-2-oxopyrrolidin-3-yl}naphthalene-2-sulfonamide, (E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide, 5-Chloro-N-{(3S)-1-[(1S)-1-methyl-2-morpholin-4-yl-2-oxoethyl]-2-oxopyrrolidin-3-yl}-1-benzothiophene-2-sulfonamide, 6-Chloro-N-{(3S)-1-[(1S)-1-methyl-2-morpholin-4-yl-2-oxoethyl]-2-oxopyrrolidin-3-yl}-1-benzothiophene-2-sulfonamide, 5-Chloro-3-methyl-N-{(3S)-1-[(1S)-1-methyl-2-morpholin-4-yl-2-oxoethyl]-2-oxopyrrolidin-3-yl}-1-benzothiophene-2-sulfonamide, 5-Chloro-N-{(3S)-1-[(1S)-1-methyl-2-morpholin-4-yl-2-oxoethyl]-2-oxopyrrolidin-3-yl}thieno[3,2-b]pyridine-2-sulfonamide, 6-Chloro-N-{(3S)-1-[(1S)-1-methyl-2-morpholin-4-yl-2-oxoethyl]-2-oxopyrrolidin-3-yl}-N-(2-oxobutyl)-1-benzothiophene-2-sulfonamide, N2-[(6-Chloro-1-benzothien-2-yl)sulfonyl]-N2-{(3S)-1-[(1S)-1-methyl-2-morpholin-4-yl-2-oxoethyl]-2-oxopyrrolidin-3-yl}glycinamide, 5-Chloro-N-{(3S)-1-[(1S)-1-methyl-2-morpholin-4-yl-2-oxoethyl]-2-oxopyrrolidin-3-yl}-N-(2-oxobutyl)-1-benzothiophene-2-sulfonamide, N2-[(5-Chloro-1-benzothien-2-yl)sulfonyl]-N2-{(3S)-1-[(1S)-1-methyl-2-morpholin-4-yl-2-oxoethyl]-2-oxopyrrolidin-3-yl}glycinamide, 6-Chloro-N-{(3S)-1-[(1S)-1-methyl-2-morpholin-4-yl-2-oxoethyl]-2-oxopyrrolidin-3-yl}-N-phenylnaphthalene-2-sulfonamide, 6-Chloro-N-(4-fluorophenyl)-N-{(3S)-1-[(1S)-1-methyl-2-morpholin-4-yl-2-oxoethyl]-2-oxopyrrolidin-3-yl}naphthalene-2-sulfonamide, 6-Chloro-N-{(3S)-1-[(1S)-1-methyl-2-morpholin-4-yl-2-oxoethyl]-2-oxopyrrolidin-3-yl}-N-pyridin-4-ylnaphthalene-2-sulfonamide, 6-Chloro-N-{(3S)-1-[(1S)-1-methyl-2-morpholin-4-yl-2-oxoethyl]-2-oxopyrrolidin-3-yl}-N-pyridin-3-ylnaphthalene-2-sulfonamide, 6-Chloro-N-{(3S)-1-[(1S)-1-methyl-2-morpholin-4-yl-2-oxoethyl]-2-oxopyrrolidin-3-yl}-N-thien-3-ylnaphthalene-2-sulfonamide, N2-[(6-Chloro-2-naphthyl)sulfonyl]-N2-((3S)-1-{(1S)-2-[(2R,6S)-2,6-dimethylmorpholin-4-yl]-1-methyl-2-oxoethyl}-2-oxopyrrolidin-3-yl)glycinamide, (E)-2-(4-Chloro-3-hydroxyphenyl)-N-{(3S)-1-[(1S)-1-methyl-2-morpholin-4-yl-2-oxoethyl]-2-oxopyrrolidin-3-yl}ethenesulfonamide, 6-Chloro-N-{(3S)-1-[(1S)-1-methyl-2-morpholin-4-yl-2-oxoethyl]-2-oxopyrrolidin-3-yl}-N-(2-morpholin-4-ylethyl)naphthalene-2-sulfonamide formate, 6-Chloro-N-{(3S)-1-[(1S)-1-methyl-2-morpholin-4-yl-2-oxoethyl]-2-oxopyrrolidin-3-yl}-N-(2-pyrrolidin-1-ylethyl)naphthalene-2-sulfonamide formate, 6-Chloro-N-[2-(dimethylamino)ethyl]-N-{(3S)-1-[(1S)-1-methyl-2-morpholin-4-yl-2-oxoethyl]-2-oxopyrrolidin-3-yl}naphthalene-2-sulfonamide formate, N-[2-([(6-Chloro-2-naphthyl)sulfonyl]{(3S)-1-[(1S)-1-methyl-2-morpholin-4-yl-2-oxoethyl]-2-oxopyrrolidin-3-yl}amino)ethyl]acetamide, 5-Chloro-N-{(3S)-1-[(1S)-1-methyl-2-morpholin-4-yl-2-oxoethyl]-2-oxopyrrolidin-3-yl}-1H-indole-2-sulfonamide, 6-Chloro-N-{(3S)-1-[(1S)-1-methyl-2-(2-methylmorpholin-4-yl)-2-oxoethyl]-2-oxopyrrolidin-3-yl}naphthalene-2-sulfonamide, and (E)-2-(5-Chlorothien-2-yl)-N-methyl-N-{(3S)-1-[(1S)-1-methyl-2-morpholin-4-yl-2-oxoethyl]-2-oxopyrrolidin-3-yl}ethenesulfonamide.

Even more preferred compounds of the invention include:

(E)-2-(4-Chlorophenyl)-N-{(3S)-1-[(1S)-1-methyl-2-morpholin-4-yl-2-oxoethyl]-2-oxopyrrolidin-3-yl}ethenesulfonamide, 6-Chloro-N-{(3S)-1-[(1S)-1-methyl-2-morpholin-4-yl-2-oxoethyl]-2-oxopyrrolidin-3-yl}naphthalene-2-sulfonamide, 5'-Chloro-N-{(3S)-1-[(1S)-1-methyl-2-morpholin-4-yl-2-oxoethyl]-2-oxopyrrolidin-3-yl}-2,2'-bithiophene-5-sulfonamide, N2-{[(E)-2-(4-Chlorophenyl)ethenyl]sulfonyl}-N2-{(3S)-1-[(1S)-1-methyl-2-morpholin-4-yl-2-oxoethyl]-2-oxopyrrolidin-3-yl}glycinamide, N2-[(5'-Chloro-2,2'-bithien-5-yl)sulfonyl]-N2-{(3S)-1-[(1S)-1-methyl-2-morpholin-4-yl-2-oxoethyl]-2-oxopyrrolidin-3-yl}glycinamide, 5'-Chloro-N-(cyanomethyl)-N-{(3S)-1-[(1S)-1-methyl-2-morpholin-4-yl-2-oxoethyl]-2-oxopyrrolidin-3-yl}-2,2'-bithiophene-5-sulfonamide, Methyl N-[(5'-chloro-2,2'-bithien-5-yl)sulfonyl]-N-{(3S)-1-[(1S)-1-methyl-2-morpholin-4-yl-2-oxoethyl]-2-oxopyrrolidin-3-yl}glycinate, 5'-Chloro-N-{(3S)-1-[(1S)-1-methyl-2-morpholin-4-yl-2-oxoethyl]-2-oxopyrrolidin-3-yl}-N-(2-oxobutyl)-2,2'-bithiophene-5-sulfonamide, N-[(5'-Chloro-2,2'-bithien-5-yl)sulfonyl]-N-{(3S)-1-[(1S)-1-methyl-2-morpholin-4-yl-2-oxoethyl]-2-oxopyrrolidin-3-yl}glycine, (E)-2-(4-Chlorophenyl)-N-(cyanomethyl)-N-{(3S)-1-[(1S)-1-methyl-2-morpholin-4-yl-2-oxoethyl]-2-oxopyrrolidin-3-yl}ethenesulfonamide, (E)-2-(4-Chlorophenyl)-N-{(3S)-1-[(1S)-1-methyl-2-morpholin-4-yl-2-oxoethyl]-2-oxopyrrolidin-3-yl}-N-(2-oxobutyl)ethenesulfonamide, Methyl N-{[(E)-2-(4-chlorophenyl)ethenyl]sulfonyl}-N-{(3S)-1-[(1S)-1-methyl-2-morpholin-4-yl-2-oxoethyl]-2-oxopyrrolidin-3-yl}glycinate, 6-Chloro-N-(3-furylmethyl)-N-{(3S)-1-[(1S)-1-methyl-2-morpholin-4-yl-2-oxoethyl]-2-oxopyrrolidin-3-yl}naphthalene-2-sulfonamide, 6-Chloro-N-{(3S)-1-[(1S)-1-methyl-2-morpholin-4-yl-2-oxoethyl]-2-oxopyrrolidin-3-yl}-N-(pyridin-3-ylmethyl)naphthalene-2-sulfonamide formate, 6-Chloro-N-ethyl-N-{(3S)-1-[(1S)-1-methyl-2-morpholin-4-yl-2-oxoethyl]-2-oxopyrrolidin-3-yl}naphthalene-2-sulfonamide, 6-Chloro-N-{(3S)-1-[(1S)-1-methyl-2-morpholin-4-yl-2-oxoethyl]-2-oxopyrrolidin-3-yl}-N-(2-oxobutyl)naphthalene-2-sulfonamide, N-2-[(6-Chloro-2-naphthyl)sulfonyl]-N-2-{(3S)-1-[(1S)-1-methyl-2-morpholin-4-yl-2-oxoethyl]-2-oxopyrrolidin-3-yl}glycinamide, 6-Chloro-N-(2-furylmethyl)-N-{(3S)-1-[(1S)-1-methyl-2-morpholin-4-yl-2-oxoethyl]-2-oxopyrrolidin-3-yl}naphthalene-2-sulfonamide, 6-Chloro-N-{(3S)-1-[(1S)-1-methyl-2-morpholin-4-yl-2-oxoethyl]-2-oxopyrrolidin-3-yl}-N-(1,3-thiazol-2-ylmethyl)naphthalene-2-sulfonamide, N2-[(6-Chloro-2-naphthyl)sulfonyl]-N2-((3S)-1-{(1S)-2-[(2R,6S)-2,6-dimethylmorpholin-4-yl]-1-methyl-2-oxoethyl}-2-oxopyrrolidin-3-yl)glycinamide, 6-Chloro-N-{(3S)-1-[(1S)-1-methyl-2-morpholin-4-yl-2-oxoethyl]-2-oxopyrrolidin-3-yl}-N-[(2-methyl-1,3-thiazol-4-yl)methyl]naphthalene-2-sulfonamide, 6-Chloro-N-{(3S)-1-[(1S)-1-methyl-2-morpholin-4-yl-2-oxoethyl]-2-oxopyrrolidin-3-yl}-N-(pyridin-2-ylmethyl)naphthalene-2-sulfonamide formate, 6-Chloro-N-{(3S)-1-[(1S)-1-methyl-2-morpholin-4-yl-2-oxoethyl]-2-oxopyrrolidin-3-yl}-N-(pyridin-4-ylmethyl)naphthalene-2-sulfonamide formate, 6-Chloro-N-(cyanomethyl)-N-{(3S)-1-[(1S)-1-methyl-2-morpholin-4-yl-2-oxoethyl]-2-oxopyrrolidin-3-yl}naphthalene-2-sulfonamide, 6-Chloro-N-methyl-N-{(3S)-1-[(1S)-1-methyl-2-morpholin-4-yl-2-oxoethyl]-2-oxopyrrolidin-3-yl}naphthalene-2-sulfonamide, 6-Chloro-N-(3,3-dimethyl-2-oxobutyl)-N-{(3S)-1-[(1S)-1-methyl-2-morpholin-4-yl-2-oxoethyl]-2-oxopyrrolidin-3-yl}naphthalene-2-sulfonamide, N-Allyl-6-chloro-N-{(3S)-1-[(1S)-1-methyl-2-morpholin-4-yl-2-oxoethyl]-2-oxopyrrolidin-3-yl}naphthalene-2-sulfonamide, Methyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate, tert-Butyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate, N-[(6-Chloro-2-naphthyl)sulfonyl]-N-{(3S)-1-[(1S)-1-methyl-2-morpholin-4-yl-2-oxoethyl]-2-oxopyrrolidin-3-yl}glycine, (E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide, 6-Chloro-N-{(3S)-1-[(1S)-1-methyl-2-morpholin-4-yl-2-oxoethyl]-2-oxopyrrolidin-3-yl}-N-(2-oxobutyl)-1-benzothiophene-2-sulfonamide, N2-[(6-Chloro-1-benzothien-2-yl)sulfonyl]-N2-{(3S)-1-[(1S)-1-methyl-2-morpholin-4-yl-2-oxoethyl]-2-oxopyrrolidin-3-yl}glycinamide, N2-[(6-Chloro-2-naphthyl)sulfonyl]-N2-((3S)-1-{(1S)-2-[(2R,6S)-2,6-dimethylmorpholin-4-yl]-1-methyl-2-oxoethyl}-2-oxopyrrolidin-3-yl)glycinamide, 6-Chloro-N-{(3S)-1-[(1S)-1-methyl-2-morpholin-4-yl-2-oxoethyl]-2-oxopyrrolidin-3-yl}-N-(2-morpholin-4-ylethyl)naphthalene-2-sulfonamide formate, 6-Chloro-N-{(3S)-1-[(1S)-1-methyl-2-morpholin-4-yl-2-oxoethyl]-2-oxopyrrolidin-3-yl}-N-(2-pyrrolidin-1-ylethyl)naphthalene-2-sulfonamide formate, 6-Chloro-N-[2-(dimethylamino)ethyl]-N-{(3S)-1-[(1S)-1-methyl-2-morpholin-4-yl-2-oxoethyl]-2-oxopyrrolidin-3-yl}naphthalene-2-sulfonamide formate, and N-[2-([(6-Chloro-2-naphthyl)sulfonyl]{(3S)-1-[(1S)-1-methyl-2-morpholin-4-yl-2-oxoethyl]-2-oxopyrrolidin-3-yl}amino)ethyl]acetamide.

In another preferred aspect compounds of the invention also include:

6-Chloro-N-{(3S)-1-[(1S)-1-methyl-2-morpholin-4-yl-2-oxoethyl]-2-oxopyrrolidin-3-yl}naphthalene-2-sulfonamide, 5'-Chloro-N-{(3S)-1-[(1S)-1-methyl-2-morpholin-4-yl-2-oxoethyl]-2-oxopyrrolidin-3-yl}-2,2'-bithiophene-5-sulfonamide, (E)-2-(4-Chlorophenyl)-N-{(3S)-1-[(1S)-1-methyl-2-morpholin-4-yl-2-oxoethyl]-2-oxopyrrolidin-3-yl}ethenesulfonamide, 5'-Chloro-N-(cyanomethyl)-N-{(3S)-1-[(1S)-1-methyl-2-morpholin-4-yl-2-oxoethyl]-2-oxopyrrolidin-3-yl}-2,2'-bithiophene-5-sulfonamide, Methyl N-[(5'-chloro-2,2'-bithien-5-yl)sulfonyl]-N-{(3S)-1-[(1S)-1-methyl-2-morpholin-4-yl-2-oxoethyl]-2-oxopyrrolidin-3-yl}glycinate, 5'-Chloro-N-{(3S)-1-[(1S)-1-methyl-2-morpholin-4-yl-2-oxoethyl]-2-oxopyrrolidin-3-yl}-N-(2-oxobutyl)-2,2'-bithiophene-5-sulfonamide, 6-Chloro-N-(3-furylmethyl)-N-{(3S)-1-[(1S)-1-methyl-2-morpholin-4-yl-2-oxoethyl]-2-oxopyrrolidin-3-yl}naphthalene-2-sulfonamide, 6-Chloro-N-{(3S)-1-[(1S)-1-methyl-2-morpholin-4-yl-2-oxoethyl]-2-oxopyrrolidin-3-yl}-N-(pyridin-3-ylmethyl)naphthalene-2-sulfonamide formate, 6-Chloro-N-{(3S)-1-[(1S)-1-methyl-2-morpholin-4-yl-2-oxoethyl]-2-oxopyrrolidin-3-yl}-N-(2-oxobutyl)naphthalene-2-sulfonamide, N-2-[(6-Chloro-2-naphthyl)sulfonyl]-N-2-{(3S)-1-[(1S)-1-methyl-2-morpholin-4-yl-2-oxoethyl]-2-oxopyrrolidin-3-yl}glycinamide, 6-Chloro-N-(2-furylmethyl)-N-{(3S)-1-[(1S)-1-methyl-2-morpholin-4-yl-2-oxoethyl]-2-oxopyrrolidin-3-yl}naphthalene-2-sulfonamide, 6-Chloro-N-{(3S)-1-[(1S)-1-methyl-2-morpholin-4-yl-2-oxoethyl]-2-oxopyrrolidin-3-yl}-N-(1,3-thiazol-2-ylmethyl)naphthalene-2-sulfonamide, 6-Chloro-N-(cyanomethyl)-N-{(3S)-1-[(1S)-1-methyl-2-morpholin-4-yl-2-oxoethyl]-2-oxopyrrolidin-3-yl}naphthalene-2-sulfonamide, 6-Chloro-N-methyl-N-{(3S)-1-[(1S)-1-methyl-2-morpholin-4-yl-2-oxoethyl]-2-oxopyrrolidin-3-yl}naphthalene-2-sulfonamide, N-Allyl-6-chloro-N-{(3S)-1-[(1S)-1-methyl-2-morpholin-4-yl-2-oxoethyl]-2-oxopyrrolidin-3-yl}naphthalene-2-sulfonamide, Methyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate, and N-[(6-Chloro-2-naphthyl)sulfonyl]-N-{(3S)-1-[(1S)-1-methyl-2-morpholin-4-yl-2-oxoethyl]-2-oxopyrrolidin-3-yl}glycine.

The compounds of formula (I) or (Ia) are Factor Xa inhibitors and as such are useful in the treatment of clinical conditions susceptible to amelioration by administration of a Factor Xa inhibitor. Such conditions include acute vascular diseases such as coronary thrombosis (for example myocardial infarction and unstable angina), thromboembolism, acute vessel closure associated with thrombolytic therapy and percutaneous transluminal coronary angioplasty (PTCA), transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke; in oedema and PAF mediated inflammatory diseases such as adult respiratory shock syndrome, septic shock and reperfusion damage; the treatment of pulmonary fibrosis; the treatment of tumour metastasis; neurogenerative disease such as Parkinson's and Alzheimer's diseases; viral infection; Kasabach Merritt Syndrome; Haemolytic uremic syndrome; arthritis; osteoporosis; as anti-coagulants for extracorporeal blood in for example, dialysis, blood filtration, bypass, and blood product storage; and in the coating of invasive devices such as prostheses, artificial valves and catheters in reducing the risk of thrombus formation.

Accordingly, one aspect of present invention provides a compound of formula (I) or (Ia) or a physiologically acceptable salt or solvate thereof for use in medical therapy, particularly for use in the amelioration of a clinical condition in a mammal, including a human, for which a Factor Xa inhibitor is indicated.

In another aspect, the invention provides a method for the treatment and/or prophylaxis of a mammal, including a human, suffering from a condition susceptible to amelioration by a Factor Xa inhibitor which method comprises administering to the subject an effective amount of a compound of formula (I) or (Ia) or a pharmaceutically acceptable salt or solvate thereof.

In another aspect, the present invention provides the use of a compound of formula (I) or (Ia) or a pharmaceutically acceptable salt or solvate thereof, for the manufacture of a medicament for the treatment and/or prophylaxis of a condition susceptible to amelioration by a Factor Xa inhibitor.

Preferably, the condition susceptible to amelioration by a Factor Xa inhibitor is selected from coronary thrombosis (for example myocardial infarction and unstable angina), pulmonary embolism, deep vein thrombosis and the prevention of thromboembolic events associated with atrial fibrillation, e.g. stroke;

It will be appreciated that reference to treatment includes acute treatment or prophylaxis as well as the alleviation of established symptoms.

While it is possible that, for use in therapy, a compound of the present invention may be administered as the raw chemical, it is preferable to present the active ingredient as a pharmaceutical formulation.

In a further aspect, the invention provides a pharmaceutical composition comprising at least one compound of formula (I) or (Ia) or a pharmaceutically acceptable salt or solvate thereof in association with a pharmaceutically acceptable carrier and/or excipient. The carrier and/or excipient must be "acceptable" in the sense of being compatible with the other ingredients of the formulation and not deletrious to the receipient thereof.

Accordingly, the present invention further provides a pharmaceutical formulation comprising at least one compound of formula (I) or (Ia) or a pharmaceutically acceptable salt or solvate thereof, thereof in association with a pharmaceutically acceptable carrier and/or excipient. The carrier and/or excipient must be "acceptable" in the sense of being compatible with the other ingredients of the formulation and not deletrious to the receipient thereof.

In another aspect, the invention provides a pharmaceutical composition comprising, as active ingredient, at least one compound of formula (I) or (Ia) or a pharmaceutically acceptable salt or solvate thereof in association with a pharmaceutically acceptable carrier and/or excipient for use in therapy, and in particular in the treatment of human or animal subjects suffering from a condition susceptible to amelioration by a Factor Xa inhibitor.

There is further provided by the present invention a process of preparing a pharmaceutical composition, which process comprises mixing at least one compound of formula (I) or (Ia) or a pharmaceutically acceptable salt or solvate thereof, together with a pharmaceutically acceptable carrier and/or excipient.

The compounds for use according to the present invention may be formulated for oral, buccal, parenteral, topical, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions or they may be presented as a dry product for constitution with water or other suitable vehicles before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in a conventional manner.

The compounds according to the present invention may be formulated for parenteral administration by injection, e.g. by bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds according to the present invention may be formulated for topical administration by insufflation and inhalation. Examples of types of preparation for topical administration include sprays and aerosols for use in an inhaler or insufflator.

Powders for external application may be formed with the aid of any suitable powder base, for example, lactose, talc or starch. Spray compositions may be formulated as aqueous solutions or suspensions or as aerosols delivered from pressurised packs, such as metered dose inhalers, with the use of a suitable propellant.

The compounds according to the present invention may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds according to the present invention may be formulated with suitable polymeric or hydrophobic materials (for example as an emulsion in an acceptable oil) or ion exchange resins or as sparingly soluble derivatives, for example, as a sparingly soluble salt.

A proposed dose of the compounds according to the present invention for administration to a human (of approximately 70 kg body weight) is 0.1 mg to 1 g, preferably to 1 mg to 500 mg of the active ingredient per unit dose, expressed as the weight of free base. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The dosage will also depend on the route of administration. The precise dose and route of administration will ultimately be at the discretion of the attendant physician or veterinarian.

The compounds of formula (I) or (Ia) may also be used in combination with other therapeutic agents. The invention thus provides, in a further aspect, a combination comprising a compound of formula (I) or (Ia) or a pharmaceutically acceptable salt or solvate thereof together with a further therapeutic agent.

When a compound of formula (I) or (Ia) or a pharmaceutically acceptable salt or solvate thereof is used in combination with a second therapeutic agent active against the same disease state the dose of each compound may differ from that when the compound is used alone. The compounds of the present invention may be used in combination with other antithrombotic drugs such as thrombin inhibitors, thromboxane receptor antagonists, prostacyclin mimetics, phosphodiesterase inhibitors, fibrinogen antagonists, thrombolytic drugs such as tissue plaminogen activator and streptokinase, non-steroidal anti-inflammatory drugs such as aspirin, and the like.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the Factor Xa inhibitor or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

When a compound of formula (I) or (Ia) or a pharmaceutically acceptable salt or solvate thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The compounds of formula (I) or (Ia) and physiologically acceptable salts or solvates thereof may be prepared by the processes described hereinafter, said processes constituting a further aspect of the invention. In the following description, the groups are as defined above for compounds of formula (I) or (Ia) unless otherwise stated.

According to a further aspect of the present invention, there is provided a process (A) for preparing a compound of formula (I) or (Ia), which process comprises reacting a compound of formula (II) with a compound of formula (III).

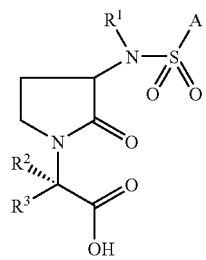

(II)

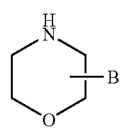

(III)

Suitably, the reaction may be carried out in the presence of a coupling agent, for example 1-[3-(dimethylamino) propyl]-3-ethyl carbodiimide hydrochloride, HOBt (1-hydroxybenzotriazole), a base, e.g. $Et_3N$ (triethylamine), and an organic solvent, e.g. DCM (dichloromethane), suitably at room temperature.

It will be appreciated by persons skilled in the art that compounds of formula (I) or (Ia) may be prepared by interconversion, utilising other compounds of formula (I) or (Ia) which are optionally protected by standard protecting groups, as precursors. For instance, compounds of formula (I) or (Ia) where B represents —$C_{1-3}$alkyl$NH_2$, may be converted into compounds of formula (I) or (Ia) possessing alternative substituents on the heterocyclic ring, e.g. —$C_{1-3}$alkyl$NR^bR^c$, by methods well known in the art (see for example March, J., Advanced Organic Chemistry, John Wiley & Sons).

Compounds of formula (II) may be prepared from compounds of formula (IV):

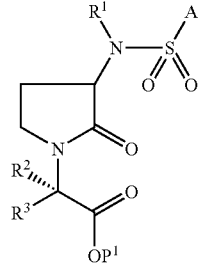

(IV)

wherein $P^1$ is a suitable carboxylic acid protecting group, e.g. t-Butyl, by removal of the protecting group under standard conditions. For example, when $P^1$ represents t-Butyl, removal of the protecting group may be effected under acidic conditions, using for example TFA (trifluoroacetic acid) in a solvent such as DCM.

A compound of formula (IV) may be prepared by reacting a compound of formula (V) with a compound of formula (VI) where $P^1$ is as described above:

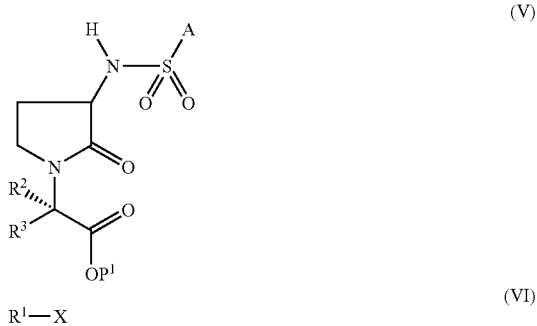

(V)

R$^1$—X  (VI)

Suitably, where X is a leaving group such as a halogen atom, e.g. bromine, the reaction is carried out in the presence of a base, e.g. LiHMDS (lithium hexamethyldisilylamide), potassium carbonate or sodium carbonate. Preferably, the reaction is effected in a suitable organic solvent, e.g. THF, DMF, at a temperature from −78° C. to +50° C., preferably −78° C. to +20° C.

Alternatively, where X is hydroxy, the coupling reaction is carried out using standard reagents such as DIAD (diisopropyl azodicarboxylate) and n-Bu$_3$P (tri n-Butyl phosphine) in a solvent such as tetrahydrofuran, suitably at room temperature.

A compound of formula (V) may be prepared by reacting a compound of formula (VII) with a compound of formula (VIII):

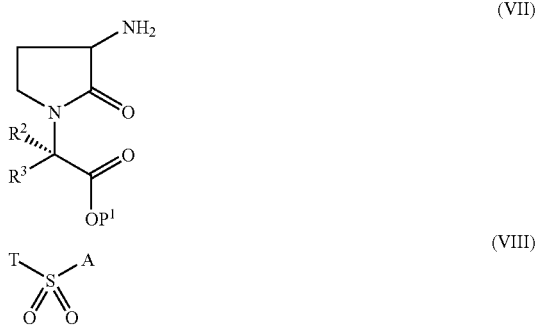

(VII)

(VIII)

wherein T is a reactive group, such as a halide, preferably chloride, and P$^1$ is as described above. The reaction is conveniently carried out in the presence of a base, e.g. pyridine, and in a suitable solvent, e.g. DCM, suitably at room temperature.

A compound of formula (VII) may be prepared from a compound of formula (IX)

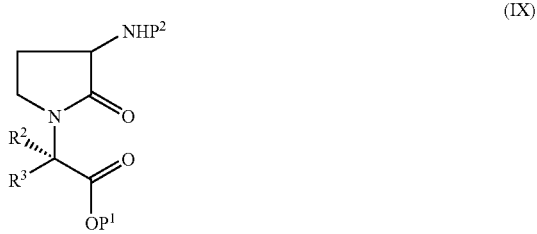

(IX)

where P$^1$ is as described above and P$^2$ represents a suitable amine protecting group, e.g. Cbz (benzyloxycarbonyl), by removal of the protecting group under standard conditions. For example, the protecting group may be removed by reaction with hydrogen in the presence of a metal catalyst, e.g. palladium/charcoal at atmospheric pressure. Suitably, the reaction is carried out in an alcoholic solvent, e.g. ethanol, suitably at room temperature.

A compound of formula (IX) may be prepared from a compound of formula (X)

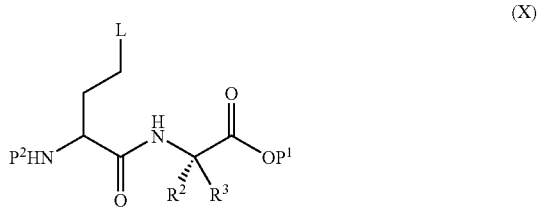

(X)

by cyclisation, wherein P$^1$ and P$^2$ are as described above and L represents a leaving group, e.g. SMeRX. The ring closure may be performed by treatment with Dowex 2×8 400 mesh OH$^-$ resin in a suitable solvent, e.g. MeCN (acetonitrile). Alternatively, the ring closure may be performed by treatment with potassium carbonate in a suitable solvent, e.g. MeCN. Generally R will represent alkyl or aralkyl and X will represent halide, especially iodide or sulphate.

Alternatively, a compound of formula (IX) may be prepared from a compound of formula (Xb):

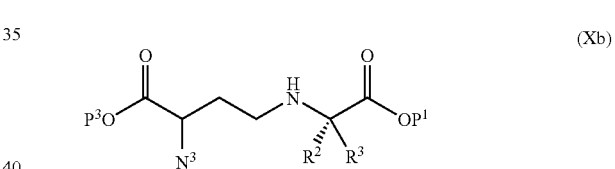

(Xb)

where P$^1$ and P$^3$ are protecting groups, by reaction with LiOH in a suitable solvent e.g. THF followed by reaction with DPPA (diphenylphosphoryl azide), a base e.g. Et$_3$N (triethylamine) in a suitable solvent e.g. DMF, suitably at room temperature to 70° C.

A compound of formula (Xb) may be prepared by reacting a compound of formula (Xb-1) with a compound of formula (Xb-2)

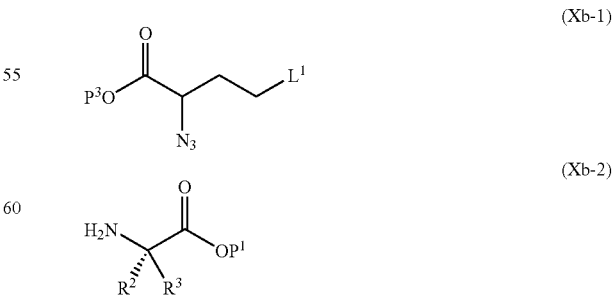

(Xb-1)

(Xb-2)

where L$^1$ is a leaving group e.g. bromine, in the presence of a base e.g. Et$_3$N in a suitable solvent e.g. MeCN.

A compound of formula (X) in which L represents SMeRX may be formed from a compound of formula (XI)

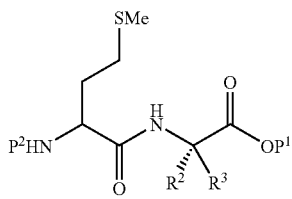

(XI)

by treatment with RX, where P$^1$ and P$^2$ are as described above and RX is a compound (e.g. MeI, benzyl iodide or Me$_2$SO$_4$) capable of converting sulphur in the SMe moiety to a sulphonium salt, in a suitable solvent, e.g. propanone or acetonitrile.

A compound of formula (XI) may be prepared by reacting a compound of formula (XII) with a compound of formula (XIII):

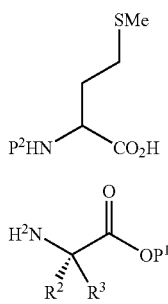

(XII)

(XIII)

Suitably, the reaction may be carried out in the presence of a coupling agent, for example 1-[3-(dimethylamino)propyl]-3-ethyl carbodiimide hydrochloride, HOBt, a base, e.g. Et$_3$N, and an organic solvent, e.g. DCM, suitably at room temperature.

There is provided a further process (B) for preparing compounds of formula (IV) from compounds of formula (VII). According to process (B), a compound of formula (IV) may be prepared by reductive amination of a compound of formula (VII) with R$^{1a}$CHO (where R$^{1a}$ is R$^1$ without a CH$_2$ linker directly attached to the N) using a suitable selective reducing agent to produce a compound of formula (XIV), followed by reaction with a compound of formula (VIII) in the presence of a base, e.g. pyridine, and in a solvent, e.g. DCM, suitably at room temperature.

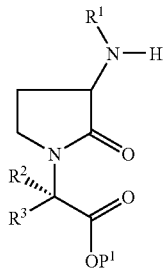

(XIV)

The reductive amination is conveniently carried out by treatment with sodium triacetoxyborohydride in the presence of an acid such as acetic acid, in a solvent such as DCM, suitably at room temperature.

Compounds of formulae (III), (VI), (VIII), (Xb-1), (Xb-2), (X), (XI), (XII) and (XIII) are known compounds and/or can be prepared by processes well known in the art.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product. For example, those skilled in the art will appreciate that, with the use of appropriate protecting groups, the coupling to any of groups —R$^1$, —SO$_2$A or formula (III) can be the final step in the preparation of a compound of formula (I) or (Ia). Hence, in another aspect of the invention, the final step in the preparation of a compound of formula (I) or (Ia) may comprise the coupling to group —R$^1$ by reacting a compound of formula (XV) with a compound of formula (VI):

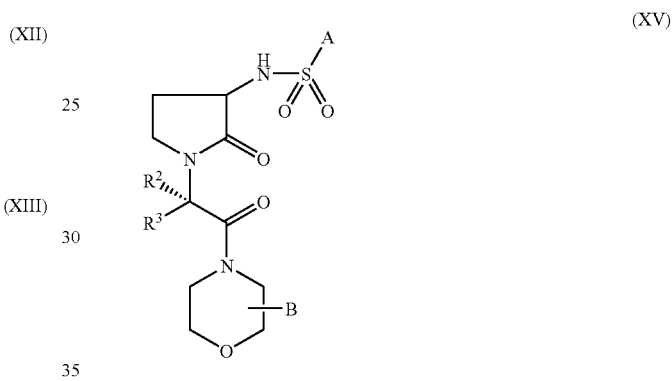

(XV)

Suitably, where X is a leaving group such as a halogen atom, e.g. bromine, the reaction is carried out in the presence of a base, e.g. LiHMDS (lithium hexamethyldisilylamide), potassium carbonate or sodium carbonate. Preferably, the reaction is effected in a suitable organic solvent, e.g. THF, DMF, at a temperature from −78° C. to +50° C., preferably −78° C. to +20° C.

In a further aspect of the present invention, the final step in the preparation of a compound of formula (I) or (Ia) may comprise the coupling to group —SO$_2$A by reacting a compound of formula (XVI) with a compound of formula (VIII):

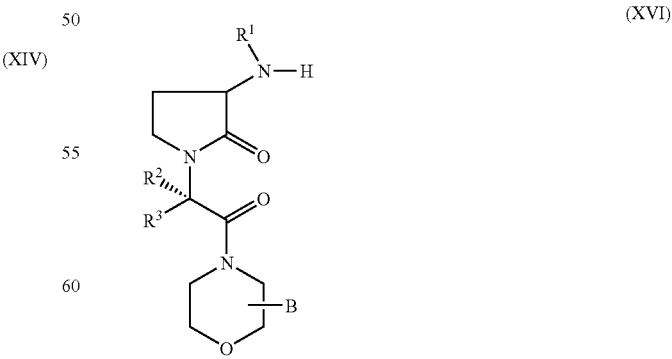

(XVI)

The reaction is conveniently carried out in the presence of a base, e.g. pyridine, and in a suitable solvent, e.g. DCM, suitably at room temperature.

In a further aspect of the present invention, a compound of formula (I) where $R^1$ is an aryl or heteroaryl group may be prepared from a compound of formula (XV) by reaction with a compound of formula (XVII):

 (XVII)

R¹—C¹ where $C^1$ is a suitable coupling group e.g. boronate [B(OH)$_2$]under metal catalysis, for example, with a copper salt such as copper(II) acetate, in the presence of an organic solvent e.g. DCM and a base, e.g. pyridine and optionally in the presence of molecular sieves.

In a further aspect of the present invention, a compound of formula (I) where A is —SO$_2$—CH=CH-aryl, SO$_2$—CH=CH-heteroaryl, SO$_2$—C(CH$_3$)=CH-aryl or SO$_2$—C(CH$_3$)=CH-heteroaryl may be prepared from a compound of formula (XVI) where $R^1$ is hydrogen, by reaction with a compound of formula (XVIII), or alternatively with a compound of formula (XIX):

 (XVIII)

T¹-SO₂—C(R)=CH₂

 (XIX)

T¹-SO₂—C(R)—CH₂-T² where $T^1$ and $T^2$ are independently reactive groups, such as a halide, preferably chloride, in the presence of a base e.g. N,N-diisopropylethylamine and a suitable solvent e.g. MeCN, suitably at room temperature, to provide a compound of formula (XV) where A is C(R)=CH$_2$, followed by reaction with a compound of formula (XX):

 (XX)

L-R^h

Where $R^h$ is aryl or heteroaryl and L is a leaving group, e.g. bromine, in the presence of a base e.g. N,N-diisopropylethylamine, and a suitable solvent e.g. dioxane and a suitable transition metal catalyst e.g. di(palladium)tris(dibenzylideneacetone) and a suitable ligand e.g. 2-(di-t-butylphosphino)biphenyl under an inert atmosphere e.g. nitrogen, at a temperature 20-100° C. preferably 40° C.

In a further aspect of the present invention, a compound of formula (I) where A is a biaryl group may be prepared from a compound of formula (XVI) where $R^1$ is hydrogen and the amino group is optionally protected, for example, as a solid supported derivative derived from reductive amination under standard conditions, by reaction with a compound of formula of formula (XXI):

 (XXI)

wherein T is a reactive group, such as a halide, preferably chloride, and $M^1$ is an aryl or heteroaryl group with a suitable coupling group e.g. halogen, preferably bromide or iodide, in the presence of a suitable solvent e.g. DMF and a suitable base, e.g. N,N-diisopropylethylamine, followed by reaction with a compound of fomula (XXII):

 (XXII)

M²-C² wherein $M^2$ is an aryl or heteroaryl group and $C^2$ is a suitable coupling group e.g. boronate [B(OH)$_2$], in the presence of a metal catalyst e.g. tetrakis(triphenylphosphine)palladium (0), a base e.g. sodium carbonate, a suitable solvent e.g. THF and optionally in the presence of a cosolvent e.g. H$_2$O, followed by removal of any protecting groups under standard conditions, e.g. under standard conditions.

Those skilled in the art will appreciate that in the preparation of the compound of formula (I) or (Ia) or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

Various intermediate compounds used in the above-mentioned process, including but not limited to certain compounds of formulae formulae (II), (IV), (V), (VII), (IX), (XIV), (XV) and (XVI) are novel and accordingly constitute a further aspect of the present invention.

The present invention will now be further illustrated by the accompanying examples which should not be construed as limiting the scope of the invention in any way.

EXAMPLES

Abbreviations
Boc t-Butyloxycarbonyl
Cbz Benzyloxycarbonyl
THF Tetrahydrofuran
DCM Dichloromethane
DMF N,N-Dimethylformamide
HOBT 1-Hydroxybenzotriazole
br broad
m multiplet
q quartet
s singlet
t triplet
d doublet Intermediate 1 tert-Butyl
N-[(benzyloxy)carbonyl]-L-methionyl-L-alaninate

Z-Protected L-methionine (10 g) was dissolved in DMF (200 ml) and 1-[3-(dimethylamino)propyl]-3-ethylcarbodiimide hydrochloride (8.13 g) was added followed by HOBT (5.72 g) and triethylamine (19.7 ml). The mixture was stirred for 1 h then L-alanine tert-butyl ester (7.7 g) was added and stirring continued for 18 h. The mixture was concentrated under reduced pressure and partitioned between diethyl ether and water. The separated organic phase was washed with hydrochloric acid (1M), saturated sodium bicarbonate solution and brine, dried (over magnesium sulphate) and concentrated under reduced pressure to give the title compound (11.9 g) as an orange oil which crystallised on standing.

Mass spectrum: Found: $MH^{30}$ 411

Intermediate 2 tert-Butyl N-[(benzyloxy)carbonyl]-D-methionyl-L-alaninate

Using Z-protected D-methionine, L-alanine tert-butyl ester, and the procedure described for Intermediate 1, the title compound was prepared.

Mass spectrum: Found: $MH^{30}$ 411

Intermediate 3 tert-Butyl N-[(benzyloxy)carbonyl]-D-methionyl-D-alaninate

Using Z-protected D-methionine, D-alanine tert-butyl ester and the procedure described for Intermediate 1, the title compound was prepared.

Mass spectrum: Found: $MH^{30}$ 411

Intermediate 4 tert-Butyl N-[(benzyloxy)carbonyl]-L-methionyl-D-alaninate

Using Z-protected L-methionine, D-alanine tert-butyl ester and the procedure described for Intermediate 1, the title compound was prepared.

Mass spectrum: Found: $MH^{30}$ 411

Intermediate 5 tert-Butyl (2S)-2-((3S)-3-{[(benzyloxy)carbonyl]amino}-2-oxopyrrolidin-1-yl)propanoate A solution of Intermediate 1 (11.9 g) in acetone (75 ml) was treated with methyl iodide (18 ml) and stirred at room temperature for 72 h. The reaction mixture was then concentrated under reduced pressure to give an orange solid that was dissolved in acetonitrile (200 ml). Dowex (OH⁻ form) resin (19.42 g) was added and the mixture stirred for 18 h at room temperature. The mixture was filtered and the resin washed with ethyl acetate. The filtrate was concentrated under reduced pressure to afford a yellow oil which was purified by Biotage™ chromatography (eluting with cyclohexane:ethyl acetate 3:2) to give the title compound (2.92 g) as a colourless oil.

Mass spectrum: Found: $MH^{30}$ 363

Intermediate 6 tert-Butyl (2S)-2-((3R)-3-{[(benzyloxy)carbonyl]amino}-2-oxopyrrolidin-1-yl)propanoate Using Intermediate 2 and the procedure described for Intermediate 5, the title compound was prepared.

Mass spectrum: Found: $MH^{30}$ 363

Intermediate 7 tert-Butyl (2R)-2-((3R)-3-{[(benzyloxy)carbonyl]amino}-2-oxopyrrolidin-1-yl)propanoate Using Intermediate 3 and the procedure described for Intermediate 5, the title compound was prepared.

Mass spectrum: Found: $MH^{30}$ 363

Intermediate 8 tert-Butyl (2R)-2-((3S)-3-{[(benzyloxy)carbonyl]amino}-2-oxopyrrolidin-1-yl)propanoate Using Intermediate 4 and the procedure described for Intermediate 5, the title compound was prepared.

Mass spectrum: Found: $MH^{30}$ 363

Intermediate 9 tert-Butyl (2S)-2-[(3S)-3-amino-2-oxopyrrolidin-1yl]propanoate

A mixture of tert-butyl (2S)-2-((3S)-3-{[(benzyloxy)carbonyl]amino}-2-oxopyrrolidin-1-yl)propanoate (2.82 g), 10% palladium on carbon (0.3 g) and ethanol (150 ml) was stirred under an atmosphere of hydrogen for 18 h. The reaction mixture was filtered through Harbolite™ and the filtrate was concentrated under reduced pressure to give the title compound (1.8 g) as a pale yellow oil.

$^1$H NMR (D$_4$MeOH): δ 4.56(1H, q), 3.57(1H, dd), 3.49-3.35(2H, 2×m), 2.48-2.39(1H, m), 1.88-1.77(1H, m), 1.47 (9H, s), 1.40 (3H, d) ppm.

Intermediate 10 tert-Butyl (2S)-2-[(3R)-3-amino-2-oxopyrrolidin-1yl]propanoate

Using Intermediate 6 and the procedure described for Intermediate 9, the title compound was prepared.

$^1$H NMR (D$_4$MeOH): δ 4.60(1H, q), 3.58(1H, dd), 3.46 (1H, dt), 3.41-3.33(1H, m), 2.48-2.40(1H, m), 1.82-1.70(1H, m), 1.45(9H, s), 1.40(3H, d) ppm.

Intermediate 11 tert-Butyl (2R)-2-[(3R)-3-amino-2-oxopyrrolidin-1-yl]propanoate

Using Intermediate 7 and the procedure described for Intermediate 9, the title compound was prepared.

$^1$H NMR (D$_4$MeOH): δ 4.58(1H, q), 3.75(1H, dd), 3.55-3.41(2H, 2×m), 2.50(1H, m), 1.90(1H, m), 1.49(9H, s), 1.42(3H, d) ppm.

Intermediate 12 tert-Butyl (2R)-2-[(3S)-3-amino-2-oxopyrrolidin-1-yl]propanoate

Using Intermediate 8 and the procedure described for Intermediate 9, the title compound was prepared.

$^1$H NMR (D$_4$MeOH): δ 4.68(1H, q), 3.78(1H, t), 3.56-3.40(2H, 2×m), 2.52(1H, m), 1.89(1H, m), 1.48(9H, s), 1.42(3H,d) ppm.

Intermediate 13

(2S)-2-((3S)-3-{[(Benzyloxy)carbonyl]amino}-2-oxopyrrolidin-1-yl) propanoic acid tert-Butyl(2S)-2-((3S)-3-{[(benzyloxy)carbonyl]amino}-2-oxopyrrolidin-1-yl)propanoate (0.5 g) was dissolved in DCM (7 ml), and trifluoroacetic acid (4.7 ml) was added. The mixture was stirred at room temperature for 4 h and then concentrated under reduced pressure to give the title compound (0.423 g) as a colourless oil, which after azeotroping with toluene, crystallised.

Mass spectrum: Found: $MH^{3O}$ 307

Intermediate 14 tert-Butyl (2S)-2-((3S)-3-{[(6-chloro-2-naphthyl)sulfonyl]amino}-2-oxopyrrolidin-1-yl)propanoate A solution of tert-butyl (2S)-2-[(3S)-3-amino-2-oxopyrrolidin-1-yl]propanoate (1.8 g) in DCM (75 ml) was treated with 6-chloronaphthylsulphonyl chloride[1] (2.28 g) and pyridine (0.705 ml) and stirred at room temperature for 72 h. The mixture was washed with water and concentrated under reduced pressure to yield an oil which was purified by Biotage™ chromatography (eluting with cyclohexane:ethyl acetate 3:1) to give the title compound (2.31 g), as a white solid.

Mass spectrum: Found: $MH^{3O}$ 453

Intermediate 15 tert-Butyl (2S)-2-((3R)-3-{[(6-chloro-2-naphthyl)sulfonyl]amino}-2-oxopyrrolidin-1-yl)propanoate Using Intermediate 10 and the procedure described for Intermediate 14, the title compound was prepared.

$^1$H NMR (CDCl$_3$): δ 8.45(1H, br.s), 7.96-7.83(4H, m), 7.56 (1H, dd), 5.41(1H, br.s), 4.66 (1H, q), 3.73(1H, dt), 3.42-3.34(2H, m), 2.62(1H, m), 2.01(1H, m), 1.38-1.32 (12H, s+d) ppm.

Intermediate 16 tert-Butyl (2R)-2-((3R)-3-{[(6-chloro-2-naphthyl)sulfonyl]amino}-2-oxopyrrolidin-1-yl)propanoate Using Intermediate 11 and the procedure described for Intermediate 14, the title compound was prepared.

Mass spectrum: Found: $MH^{3O}$ 453

Intermediate 17

(2S)-2-((3S)-3-{[(6-Chloro-2-naphthyl)sulfonyl]amino}-2-oxopyrrolidin-1-yl)propanoic acid tert-Butyl (2S)-2-((3S)-3-{[(6-chloro-2-naphthyl)sulfonyl]amino}-2-oxopyrrolidin-1-yl)propanoate (0.643 g) was dissolved in DCM (19 ml), and trifluoroacetic acid (19 ml) was added. The mixture was stirred at room temperature for 2.5 h and then concentrated under reduced pressure. Anhydrous DCM (4 ml) was added and the solution concentrated under reduced pressure. Repetitive addition of DCM and concentration under reduced pressure provided the title compound (0.56 g) as a white foam.

Mass spectrum: Found: $MH^{3O}$ 397

Intermediate 18

(2S)-2-((3R)-3-{[(6-Chloro-2-naphthyl)sulfonyl]amino}-2-oxopyrrolidin-1-yl)propanoic acid- Using Intermediate 15 and the procedure described for Intermediate 17, the title compound was prepared.

Mass spectrum: Found: $MH^{3O}$ 397

Intermediate 19

(2R)-2-((3R)-3-{[(6-Chloro-2-naphthyl)sulfonyl]amino}-2-oxopyrrolidin-1-yl)propanoic acid Using Intermediate 16 and the procedure described for Intermediate 17, the title compound was prepared.

Mass spectrum: Found: $MH^{3O}$ 397

Intermediate 20 tert-Butyl (2R)-2-(3-azido-2-oxopyrrolidin-1-yl) propanoate

To a solution of D-alanine tert-butylester (1.28 g) and N,N-diisopropylethylamine (1.22 ml) in acetonitrile (15 ml), was added a solution of ethyl 2-azido-4-bromobutanoate (1 g) and sodium iodide (0.02 g) in acetonitrile (5 ml). The mixture was heated at 60° C. for 60 h and then concentrated under reduced pressure to give a brown oil. This oil was partitioned between DCM and water. The separated organic layer was washed further with water and dried (over magnesium sulphate), and concentrated under reduced pressure. The residual brown oil was purified using Biotage™ chromatography (silica, eluting with cyclohexane:ethyl acetate 3:1) to give the title compound (0.204 g) as a mixture of two diastereoisomers.

T.l.c. (cyclohexane:ethyl acetate, 2:1) R$^f$ 0.20

Intermediates 16 and 21 tert-Butyl (2R)-2-((3R)-3-{[(6-chloro-2-naphthyl)sulfonyl]amino}-2-oxopyrrolidin-1-yl)propanoate (1)

tert-Butyl (2R)-2-((3S)-3-{[(6-chloro-2-naphthyl)sulfonyl]amino}-2-oxopyrrolidin-1-yl)propanoate (2)

A mixture of tert-butyl (2R)-2-(3-azido-2-oxopyrrolidin-1-yl)propanoate (0.204 g), 10% palladium on carbon (0.02 g) and ethanol (10 ml) was stirred under an atmosphere of hydrogen for 5 h. The reaction mixture was filtered through Harbolite™ and the filtrate was concentrated under reduced pressure to give a yellow oil. The oil (0.150 g) in DCM (10 ml) was treated with 6-chloronaphthylsulphonyl chloride[1] (0.188 g) and pyridine (0.058 ml) and stirred at room temperature for 72 h. The mixture was washed with water and concentrated under reduced pressure to yield an oil which was purified by Biotage™ chromatography (eluting with cyclohexane:ethyl acetate 2:1) to give the title compounds [(1)—0.067 g and (2)—0.060 g], both as white solids.

(1) Mass spectrum: Found: $MH^{3O}$ 453
(2) Mass spectrum: Found: $MH^{3O}$ 453

Intermediate 22 tert-Butyl (2S)-2-{(3S)-3-[[(6-chloro-2-naphthyl)sulfonyl](2-oxobutyl)amino]-2-oxopyrrolidin-1-yl}propanoate A solution of tert-butyl (2S)-2-((3S)-3-{[(6-chloro-2-naphthyl)sulfonyl]amino}-2-oxopyrrolidin-1-yl)propanoate (0.07 g) in THF (2 ml) was cooled to −78° C. under nitrogen, and treated with lithium bis(trimethylsilyl) amide (1.0M solution in THF; 0.186 ml), followed by 1-bromo-2-butanone (0.08 ml). The resultant solution was allowed to reach room temperature and stirred for a further 72 h. Methanol (1 ml) was added and the resultant solution concentrated under reduced pressure. The residue was purified using SPE (silica, eluting with cyclohexane:ethyl acetate 10:1, 5:1, 3:1, 2:1, 1:1, 1:2, 1:3, 1:5, ethyl acetate and methanol:ethyl acetate 1:9) to give the title compound (0.07 g) as a gum.

Mass spectrum: Found: $MH^{30}$ 523

Similarly prepared using other commercially available alkyl halides, was:

Intermediate 23 tert-Butyl (2S)-2-((3S)-3-{(2-amino-2-oxoethyl)[(6-chloro-2-naphthyl)sulfonyl]amino}-2-oxopyrrolidin-1-yl)propanoate Mass spectrum: Found: $MH^{30}$ 510

Intermediate 24 tert-Butyl (2R)-2-{(3S)-3-[[(6-chloro-2-naphthyl)sulfonyl](methyl)amino]-2-oxopyrrolidin-1-yl}propanoate The title compound was prepared using Intermediate 21 and methyl tosylate, and the synthetic procedure described for Intermediate 22.

Mass spectrum: Found: $MH^{30}$ 467

Intermediate 25

(2S)-2-{(3S)-3-[[(6-Chloro-2-naphthyl)sulfonyl](2-oxobutyl)amino]-2-oxopyrrolidin-1-yl}propanoic acid tert-Butyl (2S)-2-{(3S)-3-[[(6-chloro-2-naphthyl)sulfonyl](2-oxobutyl)amino]-2-oxopyrrolidin-1-yl}propanoate (0.07 g) was dissolved in DCM (2 ml), and trifluoroacetic acid (2 ml) was added. The mixture was stirred at room temperature for 1.5 h and then partitioned between water and DCM. The organic layer was separated, dried (over magnesium sulphate) and concentrated under reduced pressure to give the title compound (0.063 g) as an orange gum.

Mass spectrum: Found: $MH^{30}$ 467

Intermediate 26

(2S)-2-((3S)-3-{(2-Amino-2-oxoethyl)[(6-chloro-2-naphthyl)sulfonyl]amino}-2-oxopyrrolidin-1-yl)propanoic acid Using Intermediate 23 and similar chemistry to that described for Intermediate 25, the title compound was prepared.

Intermediate 27

(2R)-2-{(3S)-3-[[(6-Chloro-2-naphthyl)sulfonyl](methyl)amino]-2-oxopyrrolidin-1-yl}propanoic acid Using Intermediate 24 and similar chemistry to that described for Intermediate 25, the title compound was prepared.

Mass spectrum: Found: $MH^{30}$ 411

Intermediate 28

(2R)-2-((3S)-3-{[(6-Chloro-2-naphthyl)sulfonyl]amino}-2-oxopyrrolidin-1-yl)propanoic acid Using Intermediate 21 and the procedure described for Intermediate 13, the title compound was similarly prepared.

Mass spectrum: Found: $MH^{30}$ 397

Intermediate 29 tert-Butyl (2S)-2-{(3S)-3-[[(6-chloro-2-naphthyl)sulfonyl](2-furylmethyl)amino]-2-oxopyrrolidin-1-yl}propanoate A solution of tert-butyl (2S)-2-((3S)-3-{[(6-chloro-2-naphthyl)sulfonyl]amino}-2-oxopyrrolidin-1-yl)propanoate (0.07 g) in THF (0.5 ml) was treated with diisopropyl azodicarboxylate (0.06 ml), 3-furfuryl alcohol (0.030 g) and tributylphosphine (0.075 ml) and shaken at room temperature for 18 h. The mixture was concentrated under reduced pressure and the residue purified by Biotage™ chromatography (eluting with cyclohexane:ethyl acetate 3:1) to give the title compound (0.015 g) as a colourless gum.

Mass spectrum: Found: $MH^{30}$ 533

Using similar chemistry, but selecting the appropriate starting materials the following were prepared:

Intermediate 30 tert-Butyl (2S)-2-{(3S)-3-[[(6-chloro-2-naphthyl)sulfonyl](1,3-thiazol-2-yl methyl)amino]-2-oxopyrrolidin-1-yl}propanoate Mass spectrum: Found: $MH^+$ 550

Intermediate 31

(2S)-2-{(3S)-3-[[(6-Chloro-2-naphthyl)sulfonyl](1,3-thiazol-2-ylmethyl)amino]-2-oxopyrrolidin-1-yl}propanoic acid A solution of tert-butyl (2S)-2-{(3S)-3-[[(6-chloro-2-naphthyl)sulfonyl](1,3-thiazol-2-ylmethyl)amino]-2-oxopyrrolidin-1-yl}propanoate (0.03 g) in DCM (1 ml) was treated with trifluoroacetic acid (1 ml) and stirred at room temperature for 1 h. The solution was then concentrated under reduced pressure to give the title compound (0.019 g) as a colourless solid.

Mass spectrum: Found: $MH^+$ 494

Using similar chemistry, but selecting the appropriate starting materials the following were prepared:

Intermediate 32

(2S)-2-{(3S)-3-[[(6-Chloro-2-naphthyl)sulfonyl](2-furylmethyl)amino]-2-oxopyrrolidin-1-yl}propanoic acid mixture with (2S)-2-((3S)-3-{[(6-chloro-2-naphthyl)sulfonyl]amino}-2-oxopyrrolidin-1-yl)propanoic acid (56:44)

Mass spectrum: Found: $MH^{30}$ 478

Intermediate 33 tert-Butyl 5-chloro-2-[({(3S)-1-[(1S)-1-methyl-2-morpholin-4-yl-2-oxoethyl]-2-oxopyrrolidin-3-yl}amino)sulfonyl]-1H-indole-1-carboxylate 1-tert-Butoxycarbonyl-5-chloroindole (0.1 g) was dissolved in anhydrous THF (2 ml) under nitrogen and cooled to −78° C. n-Butyllithium (1.6M in hexanes, 0.273 ml) was added dropwise over 10 min. After stirring at −78° C. for 45 min, sulphur dioxide gas was bubbled through the reaction for 5 min. The reaction mixture was allowed to reach room temperature over 2 h and concentrated under reduced pressure to give an off-white solid. The solid was re-suspended in anhydrous DCM (2 ml) and treated with N-chlorosuccinimide (0.0584 g). The mixture was then stirred for 1 h at room temperature and any remaining white solid removed by filtration. Half of this filtrate was treated with pyridine (0.017 ml) and Intermediate 40 (0.022 g). The reaction mixture was stirred at 40° C. for 5 h and then 72 h at 30° C. in a sealed vessel. The reaction mixture was washed with water, the organic phase separated and dried (over magnesium sulphate), and evaporated under a stream of nitrogen to give a residue which was purified by mass directed preparative h.p.l.c. to give the title compound (0.011 g) as a colourless glass.

Mass spectrum: Found: $MH^{30}$ 555

Intermediate 34

N-{(3S)-1-[(1S)-1-Methyl-2-morpholin-4-yl-2-oxoethyl]-2-oxopyrrolidin-3-yl}ethenesulfonamide 2-Chloroethanesulfonyl chloride (0.284 ml) was added dropwise to a mixture of Intermediate 40 (0.436 g) and N,N-di-isopropylethylamine (0.938 ml) in dry acetonitrile (6 ml) at 0° C. over 2 min. The mixture was allowed to reach room temperature and stirred for 3 days, after which the reaction was quenched with water and concentrated under reduced pressure to give a brown residue. This residue was partitioned between ethyl acetate and water. The combined organic extracts were dried (over magnesium sulphate) and concentrated under reduced pressure to give a brown foam which was purified by SPE (silica, eluting with ethyl acetate:cyclohexane 1:1, ethyl acetate and then ethyl acetate:methanol 19:1) to give the title compound (0.227 g) as a clear film.

Mass Spectrum: Found: $MH^{30}$ 332

Intermediate 35 tert-Butyl (2S)-2-((3S)-3-{[(5'-chloro-2,2'-bithien-5-yl)sulfonyl]amino}-2-oxopyrrolidin-1-yl)propanoate A solution of tert-butyl (2S)-2-[(3S)-3-amino-2-oxopyrrolidin-1-yl]propanoate (0.337 g) in acetonitrile (20 ml) was treated with triethylamine (0.41 ml) and 5'-chloro-2,2'-bithiophene-5-sulfonyl chloride[2] (0.372 g) and stirred at room temperature for 17 h. The mixture was concentrated under reduced pressure and the residue purified using SPE (aminopropyl, eluting with methanol) to give the title compound (0.651 g) as a brown oil.

Mass spectrum: Found: $MH^{30}$ 491

Using similar chemistry and Intermediate 9, the following were prepared:

Intermediate 36 tert-Butyl (2S)-2-[(3S)-3-({[(E)-2-(4-chlorophenyl)ethenyl]sulfonyl}amino)-2-oxopyrrolidin-1-yl]propanoate Mass spectrum: Found: $MH^{30}$ 429

Intermediate 37 tert-Butyl (2S)-2-[(3S)-3-{(2-amino-2-oxoethyl)[(E)-2-(4-chlorophenyl)ethenyl]sulfonyl}amino)-2-oxopyrrolidin-1-yl]propanoate Using Intermediate 36, and the synthetic procedure described for Intermediate 22, the title compound was similarly prepared.

Mass spectrum: Found: $MH^{30}$ 487

Intermediate 38 tert-Butyl (2S)-2-((3S)-3-{(2-amino-2-oxoethyl){[(5'-chloro-2,2'-bithien-5-yl)sulfonyl]amino}-2-oxopyrrolidin-1-yl)propanoate Using Intermediate 35, and the synthetic procedure described for Intermediate 22, the title compound was similarly prepared.

Mass spectrum: Found: $MH^{30}$ 548

Intermediate 39

Benzyl (3S)-1-[(1S)-1-methyl-2-morpholin-4-yl-2-oxoethyl]-2-oxopyrrolidin-3-ylcarbamate (2S)-2-((3S)-3-{[(Benzyloxy)carbonyl]amino}-2-oxopyrrolidin-1-yl)propanoic acid (84.5 g) was dissolved in DMF (2 l) and O-(benzotriazol-1-yl)-N,N,N',N'-tetramethyluronium tetrafluoroborate (161 g) was added, followed by N,N-diisopropylethylamine (92 ml) and morpholine (46 ml). The mixture was stirred under nitrogen for 2.5 h, and saturated aqueous ammonium chloride was added. The mixture was stirred for 15 min then partitioned between water and ethyl acetate. The separated organic phase was washed with lithium chloride (10% by weight), followed by saturated sodium bicarbonate and brine. The organic layer was dried (over sodium sulphate) and concentrated under reduced pressure to give the title compound (65 g) as a yellow solid.

Mass spectrum: Found: $MH^{30}$ 376

Intermediate 40

(3S)-3-Amino-1-[(1S)-1-methyl-2-morpholin-4-yl-2-oxoethyl]pyrrolidin-2-one

A mixture of benzyl (3S)-1-[(1S)-1-methyl-2-morpholin-4-yl-2-oxoethyl]-2-oxopyrrolidin-3-ylcarbamate (20 g), 10% palladium on carbon (2 g) and ethanol (1.31) was stirred under an atmosphere of hydrogen for 16 h. The reaction mixture was filtered through Celite™ and the filtrate was concentrated under reduced pressure to give the title compound (12.3 g) as a pale white oil.

$^1$H NMR (D$_4$MeOH): δ5.05(1H, dd), 3.59(9H, m), 3.37 (2H, m), 2.42(1H, m), 1.75(1H, m), 1.30(3H, d) ppm.

Intermediate 41 tert-Butyl (2S)-2-((3S)-3-{[(2-methyl-1 3-thiazol-4-yl)methyl]amino}-2-oxopyrrolidin-1-yl)propanoate A solution of 2-methyl-1,3-thiazole-4-carbaldehyde (0.028 g) in DCM (2 ml) was treated with Intermediate 9 (0.05 g) followed by acetic acid (0.013 ml) and tetramethylammonium triacetoxyborohydride (0.116 g), and the resultant mixture stirred at room temperature for 66 h. The reaction mixture was partitioned between water and DCM. The organic layer was separated, dried (over magnesium sulphate) and concentrated under reduced pressure to give the title compound (0.07 g) as an oil.

Mass spectrum: Found: MH$^{30}$ 340

Using similar chemistry, but selecting the appropriate starting materials the following were prepared:

Intermediate 42 tert-Butyl (2S)-2-{(3S)-2-oxo-3-[(pyridin-4-ylmethyl)amino]pyrrolidin-1-yl}propanoate Mass spectrum: Found: MH$^{30}$ 320

Intermediate 43 tert-Butyl (2S)-2-{(3S)-2-oxo-3-[(pyridin-2-ylmethyl)amino]pyrrolidin-1-yl}propanoate Mass spectrum: Found: MH$^{30}$ 320

Intermediate 44 tert-Butyl (2S)-2-((3S)-3-{[(6-chloro-2-naphthyl)sulfonyl][(2-methyl-1,3-thiazol-4-yl)methyl]amino}-2-oxopyrrolidin-1-yl)propanoate Using Intermediate 41 and the synthetic procedure described for Intermediate 14, the title compound was similarly prepared.

Mass spectrum: Found: MH$^{30}$ 564

Intermediate 45 tert-Butyl (2S)-2-{(3S)-3-[[(6-chloro-2-naphthyl)sulfonyl](pyridin-4-ylmethyl)amino]-2-oxopyrrolidin-1-yl}propanoate Using Intermediate 42 and the synthetic procedure described for Intermediate 14, the title compound was similarly prepared.

Mass spectrum: Found: MH$^{30}$ 544

Intermediate 46 tert-Butyl (2S)-2-{(3S)-3-[[(6-chloro-2-naphthyl)sulfonyl](pyridin-2-ylmethyl)amino]-2-oxopyrrolidin-1-yl}propanoate Using Intermediate 43 and the synthetic procedure described for Intermediate 14, the title compound was similarly prepared.

Mass spectrum: Found: MH$^{30}$ 544

Intermediate 47

(2S)-2-((3S)-3-{[(6-Chloro-2-naphthyl)sulfonyl][(2-methyl-1,3-thiazol-4-yl)methyl]amino}-2-oxopyrrolidin-1-yl)propanoic acid Using Intermediate 44 and the synthetic procedure described for Intermediate 13, the title compound was similarly prepared.

Mass spectrum: Found: MH$^{30}$ 508

Intermediate 48

(2S)-2-{(3S)-3-[[(6-Chloro-2-naphthyl)sulfonyl](pyridin-4-ylmethyl)amino]-2-oxopyrrolidin-1-yl}propanoic acid hydrochloride Using Intermediate 45 and the synthetic procedure described for Intermediate 13, the title compound was similarly prepared.

Mass spectrum: Found: MH$^{30}$ 488

Intermediate 49

(2S)-2-{(3S)-3-[[(6-Chloro-2-naphthyl)sulfonyl](pyridin-2-ylmethyl)amino]-2-oxopyrrolidin-1-yl}propanoic acid hydrochloride Using Intermediate 46 and the synthetic procedure described for Intermediate 13, the title compound was similarly prepared.

Mass spectrum: Found: MH$^{30}$ 488

Intermediate 50

5-Chloro-1-benzofuran

To a solution of 5-chloro-1-benzofuran-2-carboxylic acid (0.2 g) in 1-methyl-2-pyrrolidinone (2 ml) was added copper granules (0.2 g). The reaction mixture was heated at 250° C. for 3.5 min in a microwave. The reaction vessel was cooled to room temperature and the mixture combined with four other similar mixtures and the combined mixtures partitioned between water and diethyl ether. The organic layer was washed with water and brine, dried (over magnesium sulphate) and concentrated under reduced pressure to give the title compound (0.65 g) as a yellow oil.

Gas-chromatography electron-ionisation spectrum: Found: M$^+$ 152, Rt 5.72 min

Intermediate 51

5-Chloro-1-benzofuran-2-sulfonyl chloride n-Butyl lithium (1.6M in hexanes, 0.045 ml) was added to a cooled (−78° C.) solution of Intermediate 50 (0.11 g) in anhydrous THF (5 ml) over 5 min. The reaction was stirred for a further 5 min, warmed to −45° C. and stirred for 40 min. The mixture was cooled to −70° C. and sulphur dioxide gas bubbled into the vessel over 7 min. The solution was allowed to warm to room temperature over 45 min, and then concentrated under reduced pressure to give a yellow gum. To a suspension of the gum in anhydrous DCM (4 ml) was added N-chlorosuccinimide (0.118 g) and the mixture stirred at room temperature for 75 min. The solution was filtered, and the filtrate concentrated under reduced pressure to give the title compound (0.093 g) as a yellow solid.

Mass Spectrum: Found: $MH^{30}$ 260

Intermediate 52

2-Chloro-4-ethenylphenol

To a slurry of methyltriphenylphosphonium bromide (0.23 g) in dry THF (5 ml) under nitrogen at −78° C., n-butyl lithium (1.6M in hexanes, 0.37 ml) was added dropwise over 2 min. The mixture was allowed to warm to 0° C., stirred for 20 min, cooled to −78° C. and a solution of 3-chloro-4-[[(1,1-dimethylethyl)dimethylsilyl]oxy]benzaldehyde* (0.134 g) in dry THF (5 ml) added. The reaction mixture was allowed to reach room temperature overnight and quenched with saturated aqueous ammonium chloride. The resultant mixture was extracted with diethyl ether and the combined organic extracts were concentrated under reduced pressure. The residue was purified using SPE (silica, eluting with cyclohexane, followed by 5% to 25% ethyl acetate:cyclohexane) to give the title compound (0.049 g) as an oil.

*Boukouvalas, J; Maltais, F; Lachance, N., Tetrahedron Lett. (1994), 35(43), 7897-900.

H.p.l.c. (1) Rt 3.26 min

Intermediate 53 tert-Butyl (2-chloro-4-vinylphenoxy)diphenylsilane

A mixture of Intermediate 52 (0.038 g), imidazole (0.042 g) and tert-butyldiphenylsilyl chloride (0.083 ml) was stirred in dry DMF (0.5 ml) at room temperature under nitrogen for 20 h. The mixture was quenched with water, extracted with diethyl ether, dried (over magnesium sulphate), filtered and concentrated under reduced pressure. The resultant oil was purified using SPE (silica, eluting with cyclohexane followed by 5% to 20% ethyl acetate:cyclohexane) to give the title compound (0.102 g) as an oil.

H.p.l.c. (1) Rt 4.71 min

Intermediate 54

3-{[tert-Butyl(dimethyl)silyl]oxy}-4-chlorobenzaldehyde

A mixture of 4-chloro-3-hydroxy-benzaldehyde* (0.354 g), 4-N,N-dimethylaminopyridine (0.028 g), tert-butyldimethylsilyl chloride (0.409 g) and triethylamine (0.473 ml) in DCM (15 ml) was stirred at room temperature under nitrogen for 19 h. The mixture was quenched with saturated aqueous sodium bicarbonate and extracted with diethyl ether. The combined organic extracts were concentrated under reduced pressure to give an oil which was purified using SPE (silica, eluting with cyclohexane followed by 10% to 30% ethyl acetate:cyclohexane) to give the title compound (0.42 g) as an oil.

*Kelley, J; Linn, J; Selway, J. W. T., J. Med. Chem. (1989), 32(8), 1757-63.

H.p.l.c. (1) Rt 4.11 min

Intermediate 55

(E)-2-(3-{[tert-Butyl(diphenyl)silyl]oxy}-4-chlorophenyl)-N-{(3S)-1-[(1S)-1-methyl-2-morpholin-4-yl-2-oxoethyl]-2-oxopyrrolidin-3-yl}ethenesulfonamide Sulphuryl chloride (0.103 ml) was added dropwise to DMF (0.116 ml) at 0° C. under nitrogen, over 5 min. The mixture was allowed to reach room temperature and stirred for 30 min. Intermediate 57 (0.293 g) in cyclohexane (0.2 ml) was added in one portion and the resultant mixture was heated at 90° C. for 6 h. The cooled mixture was poured onto crushed ice, extracted with diethyl ether, dried (over sodium sulphate) and concentrated under reduced pressure. This crude sulfonyl chloride was treated with Intermediate 40 (0.134 g), 4-dimethylaminopyridine (0.0068 g), N,N'-diisopropylethylamine (0.192 ml) in dry DCM (5 ml), and after stirring for 3 days at room temperature under nitrogen, the mixture was concentrated under reduced pressure. The resultant solution was washed with water and filtered through a hydrophobic frit. The filtrate was concentrated under reduced pressure to give an oil, which was purified by SPE (silica, eluting with cyclohexane:ethyl acetate 19:1 and then 10:1) followed by mass directed preparative h.p.l.c. to give the title compound (0.0078 g) as a colourless gum.

Mass spectrum: Found: $MH^{30}$ 696

Intermediate 56

2-Chloro-5-vinylphenol

The title compound was prepared using Intermediate 54 and the synthetic procedure described for Intermediate 52.

H.p.l.c. (1) Rt 3.22 min

Intermediate 57 tert-Butyl(2-chloro-5-vinylphenoxy)diphenylsilane

The title compound was prepared using Intermediate 56 and the synthetic procedure described for Intermediate 53.

H.p.l.c. (1) Rt 4.68 min

Intermediate 58

(3S)-3-{[(6-Chloro-1,3-benzothiazol-2-yl)thio]amino}-1-[(1S)-1-methyl-2-morpholin-4-yl-2-oxoethyl]pyrrolidin-2-one N-Chlorosuccinimide (0.37 g) was added to 4-chloro-2-mercaptobenzothiazole (0.5 g) in DCM (15 ml) under nitrogen, and stirred at room temperature for 3 h. A solution of Intermediate 40 (0.569 g) and triethylamine (1.04 ml) in anhydrous DCM (5 ml) were added and the resulting mixture stirred at room temperature under nitrogen for 2 h. The solution was filtered and the filtrate was diluted with DCM. The organic solution was washed with water and brine, dried (over magnesium sulphate) and concentrated under reduced pressure. The residue was purified by SPE (silica, eluting with cyclohexane:ethyl acetate 1:1 increasing polarity to ethyl acetate:methanol 19:1) to give the title compound (0.3 g) as a white solid.

Mass spectrum: Found: $MH^{30}$ 441

Intermediate 59

5-Chlorothieno[2,3-b]pyridine-2-sulfonyl chloride n-Butyl lithium (1.6M in hexanes, 0.37 ml) was added to a cooled (−78° C.) solution of 5-chlorothieno[2,3-b]pyridine* (0.100 g) in anhydrous THF (5 ml) over 15 min. The reaction was stirred for a further 5 min, warmed to −45° C. and stirred for 40 min. The mixture was cooled to −70° C. and sulphur dioxide gas was bubbled into the vessel over 10 min. The reaction was allowed to reach room temperature over 45 min, and then concentrated under reduced pressure. The residue was dissolved in anhydrous DCM (5 ml), treated with N-chlorosuccinimide (0.097 g) and stirred at room temperature for 75 min. The solution was filtered, and the filtrate concentrated under reduced pressure to give the title compound (0.198 g) as a yellow solid.
*Klemm. L. H. et. al., J. Heterocycl. Chem. (1968), 5(6), 773-8.

Mass Spectrum: Found: $MH^{30}$ 277 for dimethylamine quenched mass spectrum sample Intermediate 60

5-Chlorothieno[3,2-b]pyridine-2-sulfonyl chloride

5-Chlorothieno[3,2-b]pyridine* (0.2 g) was dissolved in anhydrous THF (10 ml) under nitrogen and cooled to −70° C. n-Butyllithium (1.6M in hexanes, 0.780 ml) was added dropwise over 10 min and the mixture stirred for a further 5 min. The mixture was warmed to −50° C. and stirred for 55 min. The reaction was cooled to −70° C., and sulphur dioxide gas was bubbled through the reaction for 10 min. The reaction was allowed to warm to room temperature and concentrated under reduced pressure to give a yellow residue which was re-suspended in anhydrous DCM (6 ml) and treated with N-chlorosuccinimide (0.189 g). The mixture was stirred for 2 h at room temperature and any remaining solid removed by filtration. The filtrate was concentrated under reduced pressure to give the title compound (0.153 g) as a white solid.
*Barker. J. N, et. al., J. Chem. Res. (1984), (3), 771-795.

Mass Spectrum: Found: $MH^{30}$ 277 for dimethylamine quenched mass spectrum sample Example 1

6-Chloro-N-{(3S)-1-[(1S)-1-methyl-2-morpholin-4-yl-2-oxoethyl]-2-oxopyrrolidin-3-yl}naphthalene-2-sulfonamide To a solution of (2S)-2-((3S)-3-{[(6-chloro-2-naphthyl)sulfonyl]amino}-2-oxopyrrolidin-1-yl)propanoic acid [Intermediate 17] (0.105 g) in DCM (10 ml) were added 1-[3-(dimethylamino)propyl]-3-ethylcarbodiimide hydrochloride (0.152 g), HOBT (0.107 g) and triethylamine (0.222 ml) and the mixture was stirred at room temperature for 30 min. Morpholine (0.07 ml) was added and the resultant mixture stirred at room temperature for 16 h. The mixture was partitioned between DCM and water. The aqueous layer was re-extracted with DCM and the combined, dried (over magnesium sulphate) organic extracts were concentrated under reduced pressure. The residue was purified using SPE (silica, eluting with cyclohexane:ethyl acetate 5:1, and ethyl acetate) to give the title compound (0.1 g) as a white solid.

Mass spectrum: Found: $MH^{30}$ 466 H.p.l.c. (1) Rt 3.13 min
$^1$H NMR (D$_4$MeOH): δ 8.54(1H, br.s), 8.08-7.96(4H, m), 7.63(1H, dd), 5.00(1H, q), 4.18(1H, dd), 3.69-3.46(9H, m), 3.31-3.29(1H, m), 2.27(1H, m), 1.77(1H, m), 1.26(3H, d) ppm.

Using similar chemistry, but selecting the appropriate staring materials the following were prepared:

Example 2

6-Chloro-N-{(3S)-1-[(1S)-2-(2,6-dimethylmorpholin-4-yl)-1-methyl-2-oxoethyl]-2-oxopyrrolidin-3-yl}naphthalene-2-sulfonamide Mass spectrum: Found: $MH^{30}$ 494 H.p.l.c. (1) Rt 3.16 min Example 3

6-Chloro-N-{(3S)-1-[(1S)-1-methyl-2-(3-methylmorpholin-4-yl)-2-oxoethyl]-2-oxopyrrolidin-3-yl}naphthalene-2-sulfonamide Mass spectrum: Found: $MH^{30}$ 480 H.p.l.c. (1) Rt 3.23 min Example 4

6-Chloro-N-((3S)-1-{(1S)-1-methyl-2-oxo-2-[3-(pyrrolidin-1-ylcarbonyl)morpholin-4-yl]ethyl}-2-oxopyrrolidin-3-yl)naphthalene-2-sulfonamide Mass spectrum: Found: $MH^{30}$ 563 H.p.l.c. (1) Rt 3.08 min Example 5

6-Chloro-N-[(3S)-1-((1S)-1-methyl-2-{2-[(methylsulfonyl)methyl]morpholin-4-yl}-2-oxoethyl)-2-oxopyrrolidin-3-yl]naphthalene-2-sulfonamide Mass spectrum: Found: $MH^{30}$ 558 H.p.l.c. (1) Rt 3.17 min Example 6

6-Chloro-N-((3S)-1-{(1S)-2-[2-(methoxymethyl)morpholin-4-yl]-1-methyl-2-oxoethyl}-2-oxopyrrolidin-3-yl)naphthalene-2-sulfonamide Mass spectrum: Found: $MH^{30}$ 510 H.p.l.c. (1) Rt 3.02 min Example 7 and Example 8

4-[(2S)-2-((3S)-3-{[(6-Chloro-2-naphthyl)sulfonyl]amino}-2-oxopyrrolidin-1-yl)propanoyl]-N-methylmorpholine-2-carboxamide [Isomer 1 and Isomer 2]

Isomer 1

Mass spectrum: Found: $MH^{30}$ 523 H.p.l.c. (1) Rt 2.93 min

Isomer 2

Mass spectrum: Found: $MH^{30}$ 523 H.p.l.c. (1) Rt 2.96 min

Example 9

6-Chloro-N-((3S)-1-{(1S)-1-methyl-2-oxo-2-[2-(pyrrolidin-1-ylcarbonyl)morpholin-4-yl]ethyl}-2-oxopyrrolidin-3-yl)naphthalene-2-sulfonamide Mass spectrum: Found: MH$^{3o}$ 563 H.p.l.c. (1) Rt 3.04 min

Example 10

4-[(2S)-2-((3S)-3-{[(6-Chloro-2-naphthyl)sulfonyl]amino}-2-oxopyrrolidin-1-yl)propanoyl]-N,N-dimethylmorpholine-2-carboxamide Mass spectrum: Found: MH$^{3o}$ 537 H.p.l.c. (1) Rt 2.96 min

Example 11 Example 12 and Example 13

4-[(2S)-2-((3S)-3-{[(6-Chloro-2-naphthyl)sulfonyl]amino}-2-oxopyrrolidin-1-yl)propanoyl]-N-(2-hydroxypropyl)morpholine-2-carboxamide [Isomer 1, Isomer 2 and Isomer 3]

Isomer 1
Mass spectrum: Found: MH$^{3o}$ 567 H.p.l.c. (1) Rt 2.92 min

Isomer 2
Mass spectrum: Found: MH$^{3o}$ 567 H.p.l.c. (1) Rt 2.91 min

Isomer 3
Mass spectrum: Found: MH$^{3o}$ 567 H.p.l.c. (1) Rt 2.92 min

Example 14

4-[(2S)-2-((3S)-3-{[(6-Chloro-2-naphthyl)sulfonyl]amino}-2-oxopyrrolidin-1-yl)propanoyl]-N,N-diisopropylmorpholine-2-carboxamide Mass spectrum: Found: MH$^{3o}$ 593 H.p.l.c. (1) Rt 3.4 min

Example 15

6-Chloro-N-((3S)-1-{(1S)-1-methyl-2-oxo-2-[2-(piperidin-1-ylcarbonyl)morpholin-4-yl]ethyl}-2-oxopyrrolidin-3-yl)naphthalene-2-sulfonamide Mass spectrum: Found: MH$^{3o}$ 577 H.p.l.c. (1) Rt 3.21 min

Example 16

6-Chloro-N-[(3S)-1-((1S)-1-methyl-2-{2-[(methylamino)methyl]morpholin-4-yl}-2-oxoethyl)-2-oxopyrrolidin-3-yl]naphthalene-2-sulfonamide formate Mass spectrum: Found: MH$^{3o}$ 509 H.p.l.c. (1) Rt 2.58 min

Example 17

6-Chloro-N-((3S)-1-{(1S)-1-methyl-2-oxo-2-[2-(pyrrolidin-1-ylmethyl)morpholin-4-yl]ethyl}-2-oxopyrrolidin-3-yl)naphthalene-2-sulfonamide formate Mass spectrum: Found: MH$^{3o}$ 549 H.p.l.c. (1) Rt 2.58 min

Example 18

6-Chloro-N-{(3S)-1-[(1S)-2-(2-{[(2-hydroxypropyl)amino]methyl}morpholin-4-yl)-1-methyl-2-oxoethyl]-2-oxopyrrolidin-3-yl}naphthalene-2-sulfonamide formate Mass spectrum: Found: MH$^{3o}$ 553 H.p.l.c. (1) Rt 2.55 min

Example 19 and Example 20

6-Chloro-N-[(3S)-1-((1S)-2-{2-[(dimethylamino)methyl]morpholin-4-yl}-1-methyl-2-oxoethyl)-2-oxopyrrolidin-3-yl]naphthalene-2-sulfonamide formate [Isomer 1 and Isomer 2]

Isomer 1
Mass spectrum: Found: MH$^{3o}$ 523 H.p.l.c. (1) Rt 2.54 min

Isomer 2
Mass spectrum: Found: MH$^{3o}$ 523 H.p.l.c. (1) Rt 2.55 min

Example 21

6-Chloro-N-[(3S)-1-((1S)-2-{2-[(diisopropylamino)methyl]morpholin-4-yl}-1-methyl-2-oxoethyl)-2-oxopyrrolidin-3-yl]naphthalene-2-sulfonamide formate Mass spectrum: Found: MH$^{3o}$ 579 H.p.l.c. (1) Rt 2.67 min

Example 22

6-Chloro-N-((3S)-1-{(1S)-1-methyl-2-oxo-2-[2-(piperidin-1-ylmethyl)morpholin-4-yl]ethyl}-2-oxopyrrolidin-3-yl)naphthalene-2-sulfonamide formate Mass spectrum: Found: MH$^{3o}$ 563 H.p.l.c. (1) Rt 2.62 min

Example 23

6-Chloro-N-((3S)-1-{(1S)-2-[(2R,6S)-2,6-dimethylmorpholin-4-yl]-1-methyl-2-oxoethyl}-2-oxopyrrolidin-3-yl)naphthalene-2-sulfonamide Mass spectrum: Found: MH$^{3o}$ 494 H.p.l.c. (1) Rt 3.15 min

Example 24

6-Chloro-N-{(3R)-1-[(1S)-1-methyl-2-morpholin-4-yl-2-oxoethyl]-2-oxopyrrolidin-3-yl}naphthalene-2-sulfonamide Mass spectrum: Found: MH$^{3o}$ 466 H.p.l.c. (1) Rt 2.96 min

Example 25

5'-Chloro-N-{(3S)-1-[(1S)-1-methyl-2-morpholin-4-yl-2-oxoethyl]-2-oxopyrrolidin-3-yl}-2,2'-bithiophene-5-sulfonamide tert-Butyl (2S)-2-((3S)-3-{[(5'-chloro-2,2'-bithien-5-yl)sulfonyl]amino}-2-oxopyrrolidin-1-yl)propanoate [Intermediate 35] (0.217 g) was dissolved in DCM (2 ml) and treated with trifluoroacetic acid (2 ml) and stirred at room temperature for 2 h. The mixture was then concentrated under reduced pressure to give an oil which was subsequently dissolved in DCM (5 ml) and treated with 1-[3-(dimethylamino)propyl]-3-ethylcarbodiimide hydrochloride (0.256 g), HOBT (0.184 g) and triethylamine (0.375 ml). After the solution had been stirred at room temperature for 30 min, morpholine (0.117 ml) was added and the resultant mixture stirred for a further 20 h. The mixture was concentrated under reduced pressure and the residue partitioned between DCM and water. The organic component was washed with water and brine, and concentrated under reduced pressure. The residue was purified using SPE (silica, eluting with cyclohexane; cyclohexane:ethyl acetate 4:1, 1:1, 1:4; ethyl acetate; methanol:ethyl acetate 1:10; methanol) to give the title compound (0.078 g) as a white solid.

Mass spectrum: Found: $MH^{30}$ 504 H.p.l.c. (1) Rt 3.17 min
$^1$H NMR ($D_4$MeOH): δ 7.61(1H, d), 7.23(1H, d), 7.22(1H, d), 7.03(1H, d), 5.04(1H, q), 4.21(1H, dd), 3.69-3.46(9H, m), 3.39-3.35(1H, m), 2.39(1H, m), 1.86(1H, m), 1.30(3H, d) ppm.

Example 26

(E)-2-(4-Chlorophenyl)-N-{(3S)-1-[(1S)-1-methyl-2-morpholin-4-yl-2-oxoethyl]-2-oxopyrrolidin-3-yl}ethenesulfonamide Using Intermediate 36 and the synthetic procedure described for Example 25, the title compound was prepared.

Mass spectrum: Found: $MH^{30}$ 442 H.p.l.c. (1) Rt 2.86 min
$^1$H NMR (CDCl$_3$): δ 7.46(1H, d), 7.44(2H, d), 7.38(2H, d), 6.89(1H, d), 5.35(1H, br.d), 5.05(1H, q), 4.00(1H, m), 3.69-3.48(9H, m), 3.35(1H, m), 2.62(1H, m), 2.06(1H, m), 1.33(3H, d) ppm.

Example 27

N2-{[(E)-2-(4-Chlorophenyl)ethenyl]sulfonyl}-N2-{(3S)-1-[(1S)-1-methyl-2-morpholin-4-yl-2-oxoethyl]-2-oxopyrrolidin-3-yl}glycinamide Using Intermediate 37 and the synthetic procedure described for Example 25, the title compound was prepared.
Mass spectrum: Found: $MH^{30}$ 499 H.p.l.c. (1) Rt 2.81 min Example 28

N2-[(5'-Chloro-2,2'-bithien-5-yl)sulfonyl]-N2-{(3S)-1-[(1S)-1-methyl-2-morpholin-4-yl-2-oxoethyl]-2-oxopyrrolidin-3-yl}glycinamide Using Intermediate 38 and the synthetic procedure described for Example 25, the title compound was prepared.
Mass spectrum: Found: $MH^{30}$ 561 H.p.l.c. (1) Rt 2.96 min Example 29

5'-Chloro-N-(cyanomethyl)-N-{(3S)-1-[(1S)-1-methyl-2-morpholin-4-yl-2-oxoethyl]-2-oxopyrrolidin-3-yl}-2,2'-bithiophene-5-sulfonamide Using Example 25 and the synthetic procedure described for Example 50, the title compound was prepared.
Mass spectrum: Found: $MH^{30}$ 543 H.p.l.c. (1) Rt 3.34 min Using similar chemistry, but selecting the appropriate staring materials the following were prepared:

Example 30

Methyl N-[(5'-chloro-2,2'-bithien-5-yl)sulfonyl]-N-{(3S)-1-[(1S)-1-methyl-2-morpholin-4-yl-2-oxoethyl]-2-oxopyrrolidin-3-yl}glycinate Mass spectrum: Found: $MH^{30}$ 576 H.p.l.c. (1) Rt 3.34 min Example 31

5'-Chloro-N-{(3S)-1-[(1S)-1-methyl-2-morpholin-4-yl-2-oxoethyl]-2-oxopyrrolidin-3-yl}-N-(2-oxobutyl)-2,2'-bithiophene-5-sulfonamide Mass spectrum: Found: $MH^{30}$ 574 H.p.l.c. (1) Rt 3.4 min Example 32

N-[(5'-Chloro-2,2'-bithien-5-yl)sulfonyl]-N-{(3S)-1-[(1S)-1-methyl-2-morpholin-4-yl-2-oxoethyl]-2-oxopyrrolidin-3-yl}glycine Using standard alkaline hydrolysis conditions, the title compound was prepared from Example 30.
Mass spectrum: Found: $MH^{30}$ 562 H.p.l.c. (1) Rt 3.21 min Example 33

(E)-2-(4-Chlorophenyl)-N-(cyanomethyl)-N-{(3S)-1-[(1S)-1-methyl-2-morpholin-4-yl-2-oxoethyl]-2-oxopyrrolidin-3-yl}ethenesulfonamide Using Example 26 and bromoacetonitrile, and the synthetic procedure described for Example 50, the title compound was prepared.
Mass spectrum: Found: $MH^{30}$ 481 H.p.l.c. (1) Rt 3.05 min
Using similar chemistry, but selecting the appropriate starting materials the following were prepared:

Example 34

(E)-2-(4-Chlorophenyl)-N-{(3S)-1-[(1S)-1-methyl-2-morpholin-4-yl-2-oxoethyl]-2-oxopyrrolidin-3-yl}-N-(2-oxobutyl)ethenesulfonamide Mass spectrum: Found: $MH^{30}$ 512 H.p.l.c. (1) Rt 3.13 min Example 35

Methyl N-{[(E)-2-(4-chlorophenyl)ethenyl]sulfonyl}-N-{(3S)-1-[(1S)-1-methyl-2-morpholin-4-yl-2-oxoethyl]-2-oxopyrrolidin-3-yl}glycinate Mass spectrum: Found: $MH^{30}$ 514 H.p.l.c. (1) Rt 3.05 min Example 36

N-{[(E)-2-(4-Chlorophenyl)ethenyl]sulfonyl}-N-{(3S)-1-[(1S)-1-methyl-2-morpholin-4-yl-2-oxoethyl]-2-oxopyrrolidin-3-yl}glycine Using standard alkaline hydrolysis conditions, the title compound was prepared from Example 35.
Mass spectrum: Found: $MH^{30}$ 500 H.p.l.c. (1) Rt 2.9 min

Example 37

6-Chloro-N-(3-furylmethyl)-N-{(3S)-1-[(1S)-1-methyl-2-morpholin-4-yl-2-oxoethyl]-2-oxopyrrolidin-3-yl}naphthalene-2-sulfonamide A solution of 6-chloro-N-{(3S)-1-[(1S)-1-methyl-2-morpholin-4-yl-2-oxoethyl]-2-oxopyrrolidin-3-yl}naphthalene-2-sulfonamide [Example 1] (0.015 g) in THF (0.5 ml) was treated with diisopropyl azodicarboxylate (0.01 ml), 3-furanmethanol (0.004 ml) and tri-n-butylphosphine (0.008 ml) and shaken at room temperature for 60 h. The mixture was concentrated under reduced pressure and the residue purified by mass directed preparative h.p.l.c. to give the title compound (0.015 g) as a colourless gum.

Mass spectrum: Found: $MH^{30}$ 546 H.p.l.c. (1) Rt 3.33 min

Using similar chemistry, but selecting the appropriate starting materials the following were prepared:

Example 38

6-Chloro-N-{(3S)-1-[(1S)-1-methyl-2-morpholin-4-yl-2-oxoethyl]-2-oxopyrrolidin-3-yl}-N-(pyridin-3-ylmethyl)naphthalene-2-sulfonamide formate The title compound was isolated from a crude reaction mixture using mass directed preparative h.p.l.c.

Mass spectrum: Found: $MH^{30}$ 557 H.p.l.c. (1) Rt 2.9 min

Example 39

6-Chloro-N-ethyl-N-{(3S)-1-[(1S)-1-methyl-2-morpholin-4-yl-2-oxoethyl]-2-oxopyrrolidin-3-yl}naphthalene-2-sulfonamide Mass spectrum: Found: $MH^{30}$ 494 H.p.l.c. (1) Rt 3.32 min

Example 40

6-Chloro-N-{(3S)-1-[(1S)-1-methyl-2-morpholin-4-yl-2-oxoethyl]-2-oxopyrrolidin-3-yl}-N-(2-oxobutyl)naphthalene-2-sulfonamide To a solution of (2S)-2-{(3S)-3-[[(6-chloro-2-naphthyl)sulfonyl](2-oxobutyl)amino]-2-oxopyrrolidin-1-yl}propanoic acid [Intermediate 25] (0.035 g) in DCM (2 ml) were added 1-[3-(dimethylamino)propyl]-3-ethylcarbodiimide hydrochloride (0.044 g), HOBT (0.031 g) and triethylamine (0.064 ml) and the mixture was stirred at room temperature for 30 min. Morpholine (0.02 ml) was added and the resultant mixture stirred at room temperature for 16 h. The mixture was partitioned between DCM and water. The aqueous layer was re-extracted with DCM and the combined, dried (over magnesium sulphate) organic extracts were concentrated under reduced pressure. The residue was purified using mass directed preparative h.p.l.c. to give the title compound (0.008 g) as a white solid.

Mass spectrum: Found: $MH^{30}$ 536 H.p.l.c. (1) Rt 3.20 min

Using similar chemistry, but selecting the appropriate starting materials the following were prepared:

Example 41

N-2-[(6-Chloro-2-naphthyl)sulfonyl]-N-2-{(3S)-1-[(1S)-1-methyl-2-morpholin-4-yl-2-oxoethyl]-2-oxopyrrolidin-3-yl}glycinamide The title compound was prepared from Intermediate 26.
Mass spectrum: Found: $MH^{30}$ 523 H.p.l.c. (1) Rt 2.87 min

Example 42

6-Chloro-N-(2-furylmethyl)-N-{(3S)-1-[(1S)-1-methyl-2-morpholin-4-yl-2-oxoethyl]-2-oxopyrrolidin-3-yl}naphthalene-2-sulfonamide The title compound was prepared from Intermediate 32.
Mass spectrum: Found: $MH^{30}$ 546 H.p.l.c. (1) Rt 3.33 min

Example 43

6-Chloro-N-{(3S)-1-[(1S)-1-methyl-2-morpholin-4-yl-2-oxoethyl]-2-oxopyrrolidin-3-yl}-N-(1,3-thiazol-2-ylmethyl)naphthalene-2-sulfonamide The title compound was prepared from Intermediate 31.
Mass spectrum: Found: $MH^{30}$ 563 H.p.l.c. (1) Rt 3.18 min

Example 44

N2-[(6-Chloro-2-naphthyl)sulfonyl]-N2-((3S)-1-{(1S)-2-[(2R,6S)-2,6-dimethylmorpholin-4-yl]-1-methyl-2-oxoethyl}-2-oxopyrrolidin-3-yl)glycinamide The title compound was prepared from Intermediate 26.
Mass spectrum: Found: $MH^{30}$ 551 H.p.l.c. (3) Rt 13.4 min

Example 45

6-Chloro-N-{(3S)-1-[(1S)-1-methyl-2-morpholin-4-yl-2-oxoethyl]-2-oxopyrrolidin-3-yl}-N-[(2-methyl-1,3-thiazol-4-yl)methyl]naphthalene-2-sulfonamide The title compound was prepared from Intermediate 47.
Mass spectrum: Found: $MH^{30}$ 577 H.p.l.c. (1) Rt 3.24 min

Example 46

6-Chloro-N-{(3S)-1-[(1S)-1-methyl-2-morpholin-4-yl-2-oxoethyl]-2-oxopyrrolidin-3-yl}-N-(pyridin-2-ylmethyl)naphthalene-2-sulfonamide formate The title compound was prepared from Intermediate 49.
Mass spectrum: Found: $MH^{30}$ 563 H.p.l.c. (1) Rt 3.62 min

Example 47

6-Chloro-N-{(3S)-1-[(1S)-1-methyl-2-morpholin-4-yl-2-oxoethyl]-2-oxopyrrolidin-3-yl}-N-(pyridin-4-ylmethyl)naphthalene-2-sulfonamide formate The title compound was prepared from Intermediate 48.
Mass spectrum: Found: $MH^{30}$ 557 H.p.l.c. (1) Rt 2.83 min

Example 48

6-Chloro-N-{(3S)-1-[(1R)-1-methyl-2-morpholin-4-yl-2-oxoethyl]-2-oxopyrrolidin-3-yl}naphthalene-2-sulfonamide To a solution of (2R)-2-((3S)-3-{[(6-chloro-2-naphthyl)sulfonyl]amino}-2-oxopyrrolidin-1-yl)propanoic acid [Intermediate 28] (0.037 g) in DCM (1.0 ml) were added 1-[3-(dimethylamino)propyl]-3-ethylcarbodiimide hydrochloride (0.036 g), HOBT (0.025 g) and triethylamine (0.026 ml) and the mixture was stirred at room temperature for 5 min. Morpholine (0.012 ml) was added and the resultant mixture stirred at room temperature for 15.5 h. The mixture was partitioned between DCM and saturated sodium bicarbonate solution and then passed through a hydrophobic frit. The organic extract was concentrated under reduced pressure and the residue was partially purified using preparative thin layer chromatography (20 cm×20 cm 1 mm thick Whatman PKF$_{256}$ SiO$_2$ plate, eluting with hexane:ethyl acetate 1:5) to give an impure sample of the title compound. This sample was repurified using preparative thin layer chromatography (20 cm×20 cm 1 mm thick Whatman PKF$_{256}$ SiO$_2$ plate, eluting with hexane:ethyl acetate 1:8) to give the title compound (0.036 g) as a white solid.

Mass spectrum: Found: MH$^{30}$ 466 H.p.l.c. (1) Rt 2.95 min

Example 49

6-Chloro-N-methyl-N-{(3S)-1-[(1R)-1-methyl-2-morpholin-4-yl-2-oxoethyl]-2-oxopyrrolidin-3-yl}naphthalene-2-sulfonamide The title compound was prepared using Intermediate 27 and the synthetic procedure described for Example 1.

Mass spectrum: Found: MH$^{30}$ 479 H.p.l.c. (1) Rt 3.18 min

Example 50

6-Chloro-N-(cyanomethyl)-N-{(3S)-1-[(1S)-1-methyl-2-morpholin-4-yl-2-oxoethyl]-2-oxopyrrolidin-3-yl}naphthalene-2-sulfonamide A solution of 6-chloro-N-{(3S)-1-[(1S)-1-methyl-2-morpholin-4-yl-2-oxoethyl]-2-oxopyrrolidin-3-yl}naphthalene-2-sulfonamide [Example 1] (0.01 g) in THF (2 ml) was cooled to −78° C. under nitrogen, and treated with lithium bis(trimethylsilyl) amide (1.0M solution in THF; 0.026 ml), followed by bromoacetonitrile (0.013 g). The resultant solution was allowed to reach room temperature and stirred for a further 16 h. The mixture was then cooled to −78° C. and further lithium bis(trimethylsilyl) amide (0.026 l) added. After reaching room temperature, the reaction mixture was stirred for a further 18 h and then quenched by the addition of methanol (1 ml). The resultant solution was concentrated under reduced pressure and the residue purified by mass directed preparative h.p.l.c. to give the title compound (0.003 g) as a white solid.

Mass spectrum: Found: MH$^{30}$ 505 H.p.l.c. (1) Rt 3.16 min

Similarly prepared using commercially available alkyl halides, were:

Example 51

6-Chloro-N-methyl-N-{(3S)-1-[(1S)-1-methyl-2-morpholin-4-yl-2-oxoethyl]-2-oxopyrrolidin-3-yl}naphthalene-2-sulfonamide Mass spectrum: Found: MH$^{30}$ 480 H.p.l.c. (1) Rt 3.11 min Example 52

6-Chloro-N-(3,3-dimethyl-2-oxobutyl)-N-{(3S)-1-[(1S)-1-methyl-2-morpholin-4-yl-2-oxoethyl]-2-oxopyrrolidin-3-yl}naphthalene-2-sulfonamide Mass spectrum: Found: MH$^{30}$ 564 H.p.l.c. (1) Rt 3.39 min Example 53

N2-[(6-Chloro-2-naphthyl)sulfonyl]-N 1-methyl-N2-{(3S)-1-[(1S)-1-methyl-2-morpholin-4-yl-2-oxoethyl]-2-oxopyrrolidin-3-yl}glycinamide Mass spectrum: Found: MH$^{30}$ 537 H.p.l.c. (1) Rt 2.98 min Example 54

N-Allyl-6-chloro-N-{(3S)-1-[(1S)-1-methyl-2-morpholin-4-yl-2-oxoethyl]-2-oxopyrrolidin-3-yl}naphthalene-2-sulfonamide Mass spectrum: Found: MH$^{30}$ 506 H.p.l.c. (1) Rt 3.26 min Example 55

Methyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate Mass spectrum: Found: MH$^{30}$ 538 H.p.l.c. (1) Rt 3.12 min Example 56

Ethyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate Mass spectrum: Found: MH$^{30}$ 552 H.p.l.c. (1) Rt 3.36 min Example 57 tert-Butyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate Mass spectrum: Found: MH$^{30}$ 580 H.p.l.c. (1) Rt 3.45 min Example 58

N-[(6-Chloro-2-naphthyl)sulfonyl]-N-{(3S)-1-[(1S)-1-methyl-2-morpholin-4-yl-2-oxoethyl]-2-oxopyrrolidin-3-yl}glycine To a solution of methyl N-[(6-chloro-2-naphthyl)sulfonyl]-N-{(3S)-1-[(1S)-1-methyl-2-morpholin-4-yl-2-oxoethyl]-2-oxopyrrolidin-3-yl}glycinate [Example 55] (0.010 g) in THF (2 ml) was added lithium hydroxide (0.003 g) in water (2 ml), and the resultant solution stirred for 16 h. The mixture was acidified to pH5 using hydrochloric acid (2N), and then concentrated under reduced pressure. The residue was purified using mass directed preparative h.p.l.c. to give the title compound (0.006 g) as a white solid.

Mass spectrum: Found: MH$^{30}$ 524 H.p.l.c. (1) Rt 3.00 min

Example 59

6-Chloro-N-{(3R)-1-[(1R)-1-methyl-2-morpholin-4-yl-2-oxoethyl]-2-oxopyrrolidin-3-yl}naphthalene-2-sulfonamide Using Intermediate 19 and the procedure described for Example 1, the title compound was prepared.
Mass spectrum: Found: MH$^{30}$ 466 H.p.l.c. (1) Rt 2.95 min

Example 60

5-Chloro-N-{(3S)-1-[(1S)-1-methyl-2-morpholin-4-yl-2-oxoethyl]-2-oxopyrrolidin-3-yl}-1-benzofuran-2-sulfonamide To a solution of (3S)-3-amino-1-[(1S)-1-methyl-2-morpholin-4-yl-2-oxoethyl]pyrrolidin-2-one [Intermediate 40] (0.077 g) in anhydrous acetonitrile (2 ml) were added 5-chloro-1-benzofuran-2-sulfonyl chloride [Intermediate 51] (0.043 g) in acetonitrile (2 ml) and pyridine (0.057 ml), and the mixture was stirred at room temperature for 72 h. Saturated ammonium chloride solution (2 ml) was added and the resultant mixture stirred at room temperature for 20 min. The mixture was concentrated under reduced pressure and the residue partitioned between chloroform and hydrochloric acid (2M). The organic layer was washed with saturated sodium bicarbonate and brine. The organic layer was isolated, dried (over magnesium sulphate) and concentrated under reduced pressure to give the title compound (0.043 g) as a white solid.
Mass spectrum: Found: MH$^{30}$ 456 H.p.l.c. (1) Rt 2.78 min

Example 61

(E)-2-(5-Chlorothien-2-yl)-N-{(3S)-1-[(1S)-1-methyl-2-morpholin-4-yl-2-oxoethyl]-2-oxopyrrolidin-3-yl}ethenesulfonamide Route 1
To a solution of (3S)-3-amino-1-[(1S)-1-methyl-2-morpholin-4-yl-2-oxoethyl]pyrrolidin-2-one [Intermediate 40] (14.9 g) in anhydrous acetonitrile (750 ml) were added (E)-2-(5-chlorothien-2-yl)ethenesulfonyl chloride (16.5 g) in acetonitrile (250 ml) and pyridine (11 ml), and the mixture was stirred at room temperature for 72 h. Saturated ammonium chloride solution was added and the resultant mixture stirred at room temperature for 30 min. The mixture was concentrated under reduced pressure and the residue partitioned between chloroform and a 1:1 mixture of hydrochloric acid (2M) and water. The organic layer was washed with a 1:1 mixture of saturated sodium bicarbonate and water, and brine. The organic layer was isolated, dried (over magnesium sulphate) and concentrated under reduced pressure to give the title compound (19.3 g) as a white solid.
Mass spectrum: Found: MH$^{30}$ 448 H.p.l.c. (1) Rt 2.99 min
$^1$H NMR (CDCl$_3$): δ 7.48(1H, d), 7.08(1H, d), 6.90(1H, d), 6.55(1H, d), 5.12(1H, br.d), 5.06(1H, q), 3.96(1H, m), 3.70-3.48(9H, m), 3.35(1H, m), 2.62(1H, m), 2.05(1H, m), 1.34(3H, d) ppm.

Route 2
To a mixture of Intermediate 34 (0.028 g), tris(dibenzylideneacetone)dipalladium (0) (0.0028 g) and 2-(di-t-butylphosphino)biphenyl (0.0037 g) under nitrogen, was added dry dioxan (0.25 ml) and the mixture was stirred for 5 min at room temperature. N,N-Di-isopropylethylamine (0.02 ml) followed by 2-bromo-5-chlorothiophene (0.016 ml) in dry dioxan (0.25 ml) were then added and the resultant solution was stirred at room temperature for 19 h and then heated at 80° C. for 1 h. The reaction was lowered to 60° C. and maintained at this temperature for 20 h. Evaporation of the cooled reaction mixture under a stream of nitrogen gave a residue that was purified by SPE (silica; using an OPTIX. Gradient elution [flow rate 10 ml/min; fraction size 10 ml; UV detector set at λ$_{max}$ 254 nm; 0 to 50% ethyl acetate-cyclohexane over 5 min, followed by 50% to 100% ethyl acetate-cyclohexane for 11 min and then 100% ethyl acetate for 4 min]) gave the title compound (0.0187 g) as a clear oil.

Using similar chemistry to that described for Example 61 Route 1, but selecting the appropriate starting materials the following were prepared:

Example 62

5-Chloro-N-{(3S)-1-[(1S)-1-methyl-2-morpholin-4-yl-2-oxoethyl]-2-oxopyrrolidin-3-yl}-1-benzothiophene-2-sulfonamide Mass spectrum: Found: MH$^{30}$ 472 H.p.l.c. (1) Rt 2.9 min
$^1$H NMR (CDCl$_3$): δ 7.87(1H, d), 7.86(1H, m), 7.78(1H, dm), 7.46(1H, dd), 5.58(1H, br.d), 5.02(1H, q), 3.91(1H, m), 3.69-3.44(9H, m), 3.34(1H, m), 2.65(1H, m), 2.10(1H, m), 1.31(3H, d) ppm.

Example 63

6-Chloro-N-{(3S)-1-[(1S)-1-methyl-2-morpholin-4-yl-2-oxoethyl]-2-oxopyrrolidin-3-yl}-1-benzothiophene-2-sulfonamide Mass spectrum: Found: MH$^{30}$ 472 H.p.l.c. (1) Rt 2.96 min
$^1$H NMR (CDCl$_3$): δ 7.89(1H, s), 7.85(1H, br.m), 7.81(1H, d), 7.44(1H, dd), 5.46(1H, br.d), 5.01(1H, q), 3.90(1H, m), 3.73-3.48(9H, m), 3.34(1H, m), 2.67(1H, m), 2.10(1H, m), 1.31(3H, d) ppm.

Example 64

5-Chloro-3-methyl-N-{(3S)-1-[(1S)-1-methyl-2-morpholin-4-yl-2-oxoethyl]-2-oxopyrrolidin-3-yl}-1-benzothiophene-2-sulfonamide Mass spectrum: Found: MH$^{30}$ 486 H.p.l.c. (1) Rt 3.11 min

Example 65

3-Cyano-N-{(3S)-1-[(1S)-1-methyl-2-morpholin-4-yl-2-oxoethyl]-2-oxopyrrolidin-3-yl}benzenesulfonamide Mass spectrum: Found: MH$^{30}$ 407 H.p.l.c. (1) Rt 2.4 min

Example 66

4-Cyano-N-{(3S)-1-[(1S)-1-methyl-2-morpholin-4-yl-2-oxoethyl]-2-oxopyrrolidin-3-yl}benzenesulfonamide Mass spectrum: Found: MH$^{30}$ 407 H.p.l.c. (1) Rt 2.4 min

Example 67

5-(5-Chloro-1,3,4-thiadiazol-2-yl)-N-{(3S)-1-[(1S)-1-methyl-2-morpholin-4-yl-2-oxoethyl]-2-oxopyrrolidin-3-yl}thiophene-2-sulfonamide Mass spectrum: Found: MH$^{30}$ 506 H.p.l.c. (1) Rt 2.82 min

Example 68

5-Chloro-N-{(3S)-1-[(1S)-1-methyl-2-morpholin-4-yl-2-oxoethyl]-2-oxopyrrolidin-3-yl}thieno[2,3-b]pyridine-2-sulfonamide Mass spectrum: Found: MH$^{30}$ 473 H.p.l.c. (1) Rt 2.64 min

Example 69

5-Chloro-N-{(3S)-1-[(1S)-1-methyl-2-morpholin-4-yl-2-oxoethyl]-2-oxopyrrolidin-3-yl}thieno[3,2-b]pyridine-2-sulfonamide Mass spectrum: Found: MH$^{30}$ 473 H.p.l.c. (1) Rt 2.53 min

Example 70

6-Chloro-N-{(3S)-1-[(1S)-1-methyl-2-morpholin-4-yl-2-oxoethyl]-2-oxopyrrolidin-3-yl}-N-(2-oxobutyl)-1-benzothiophene-2-sulfonamide Using Example 63 and 1-bromo-2-butanone, and the synthetic procedure described for Example 50, the title compound was prepared.

Mass spectrum: Found: MH$^{30}$ 542 H.p.l.c. (1) Rt 3.28 min

Using similar chemistry, but selecting the appropriate starting materials following was prepared:

Example 71

N2-[(6-Chloro-1-benzothien-2-yl)sulfonyl]-N2-{(3S)-1-[(1S)-1-methyl-2-morpholin-4-yl-2-oxoethyl]-2-oxopyrrolidin-3-yl}glycinamide Mass spectrum: Found: MH$^{30}$ 529 H.p.l.c. (1) Rt 2.91 min

Example 72

5-Chloro-N-{(3S)-1-[(1S)-1-methyl-2-morpholin-4-yl-2-oxoethyl]-2-oxopyrrolidin-3-yl}-N-(2-oxobutyl)-1-benzothiophene-2-sulfonamide Using Example 62 and 1-bromo-2-butanone, and the synthetic procedure described for Example 50, the title compound was prepared.

Mass spectrum: Found: MH$^{30}$ 542 H.p.l.c. (1) Rt 3.27 min

Using similar chemistry, but selecting the appropriate starting materials the following was prepared:

Example 73

N2-[(5-Chloro-1-benzothien-2-yl)sulfonyl]-N2-{(3S)-1-[(1S)-1-methyl-2-morpholin-4-yl-2-oxoethyl]-2-oxopyrrolidin-3-yl}glycinamide Mass spectrum: Found: MH$^{30}$ 529 H.p.l.c. (1) Rt 2.85 min

Example 74

6-Chloro-N-{(3S)-1-[(1S)-1-methyl-2-morpholin-4-yl-2-oxoethyl]-2-oxopyrrolidin-3-yl}-N-phenylnaphthalene-2-sulfonamide A mixture of Example 1 (0.0206 g), phenylboronic acid (0.0162mg), copper (II) acetate (0.016 g), triethylamine 0.123 ml) and powered 4 Å molecular sieves (dried, 0.1 g) in dry DCM (0.5 ml) was stirred at room temperature for 6 days. The reaction mixture was filtered using SPE (silica, eluting with 30% methanol in ethyl acetate). The organic fraction was concentrated under reduced pressure to give a brown residue that was purified by mass directed preparative h.p.l.c. to give the title compound (0.0062 g) as a gum.

Mass spectrum: Found: MH$^{30}$ 542 H.p.l.c. (1) Rt 3.38 min

Using similar chemistry, but selecting the appropriate starting materials the following were prepared:

Example 75

6-Chloro-N-(4-fluorophenyl)-N-{(3S)-1-[(1S)-1-methyl-2-morpholin-4-yl-2-oxoethyl]-2-oxopyrrolidin-3-yl}naphthalene-2-sulfonamide Mass spectrum: Found: MH$^{30}$ 560 H.p.l.c. (1) Rt 3.43 min

Example 76

6-Chloro-N-{(3S)-1-[(1S)-1-methyl-2-morpholin-4-yl-2-oxoethyl]-2-oxopyrrolidin-3-yl}-N-pyridin-4-ylnaphthalene-2-sulfonamide Mass spectrum: Found: MH$^{30}$ 543 H.p.l.c. (1) Rt 3.06 min

Example 77

6-Chloro-N-{(3S)-1-[(1S)-1-methyl-2-morpholin-4-yl-2-oxoethyl]-2-oxopyrrolidin-3-yl}-N-pyridin-3-ylnaphthalene-2-sulfonamide Mass spectrum: Found: MH$^{30}$ 543 H.p.l.c. (1) Rt 3.10 min

Example 78

6-Chloro-N-{(3S)-1-[(1S)-1-methyl-2-morpholin-4-yl-2-oxoethyl]-2-oxopyrrolidin-3-yl}-N-thien-3-ylnaphthalene-2-sulfonamide Mass spectrum: Found: MH$^{30}$ 548 H.p.l.c. (1) Rt 3.38 min

Example 79

N2-[(6-Chloro-2-naphthyl)sulfonyl]-N2-((3S)-1-{(1S)-2-[(2R,6S)-2,6-dimethylmorpholin-4-yl]-1-methyl-2-oxoethyl}-2-oxopyrrolidin-3-yl)glycinamide Using Intermediate 26 and the procedure described for Example 1, the title compound was prepared.

Mass spectrum: Found: MH$^{30}$ 551 H.p.l.c. (1) Rt 3.02 min

Example 80

(E)-2-(3-Chloro-4-hydroxyphenyl)-N-{(3S)-1-[(1S)-1-methyl-2-morpholin-4-yl-2-oxoethyl]-2-oxopyrrolidin-3-yl}ethenesulfonamide Sulphuryl chloride (0.036 ml) was added dropwise to DMF (0.04 ml) at 0° C. and the mixture was stirred at room temperature for 2 h. Intermediate 53 (0.102 g) in cyclohexane (0.2 ml) was added in one portion and the resultant mixture was heated at 90° C. for 6 h. The cooled reaction mixture was poured onto ice and extracted with DCM. The combined organic extracts were dried (over magnesium sulphate) and concentrated under reduced pressure to give a brown oil which was treated with sulphuryl chloride (0.035 ml) and triphenyl phosphine (0.103 g) in dry DCM (ca. 0.5 ml). After stirring for 3 h at room temperature, the mixture was filtered through a SPE silica cartridge preconditioned with cyclohexane. Elution with ethyl acetate gave, after concentration under reduced pressure, an orange-brown solid which was stirred with Intermediate 40 (0.04 g), 4-dimethylaminopyridine (0.021 g), N,N-di-isopropylethylamine (0.059 ml) in dry DCM (1 ml). After stirring for 3 days at room temperature under nitrogen, the mixture was concentrated under reduced pressure. The residue was purified initially using SPE (silica) followed by mass directed preparative h.p.l.c. to give the title compound (0.0035 g) as a white solid.

Mass spectrum: Found: $MH^{30}$ 458 H.p.l.c. (1) Rt 2.58 min

Example 81

(E)-2-(4-Chloro-3-hydroxyphenyl)-N-{(3S)-1-[(1S)-1-methyl-2-morpholin-4-yl-2-oxoethyl]-2-oxopyrrolidin-3-yl}ethenesulfonamide To a solution of Intermediate 55 (0.0078 g) in THF (0.3 ml) at −78° C. under nitrogen, tetra n-butylammonium fluoride (1M in THF, 0.014 ml) was added. The mixture was allowed to warm to room temperature over 3 days and then concentrated under reduced pressure.

The residue was purified using mass directed preparative h.p.l.c. to give the title compound (0.0043 g) as a clear film.

Mass spectrum: Found: $MH^{30}$ 458 H.p.l.c. (1) Rt 2.67 min

Example 82

6-Chloro-N-{(3S)-1-[(1S)-1-methyl-2-morpholin-4-yl-2-oxoethyl]-2-oxopyrrolidin-3-yl}-N-(2-morpholin-4-ylethyl)naphthalene-2-sulfonamide formate Example 1 (0.05 g) was dissolved in DMF (1 ml) and treated with chloroethylmorpholine hydrochloride (0.062 g) and potassium carbonate (0.093 g), and stirred at 40° C. for 2 h. The mixture was then heated at 80° C. for 8 h, cooled and treated with ethyl acetate and water. The organic extract was dried (over magnesium sulphate) and concentrated under reduced pressure. The residue was purified using mass directed preparative h.p.l.c. to give the title compound (0.018 g) as a white solid.

Mass spectrum: Found: $MH^{30}$ 579 H.p.l.c. (1) Rt 2.56 min

Using similar chemistry, but selecting the appropriate starting materials the following were prepared:

Example 83

6-Chloro-N-{(3S)-1-[(1S)-1-methyl-2-morpholin-4-yl-2-oxoethyl]-2-oxopyrrolidin-3-yl}-N-(2-pyrrolidin-1-ylethyl)naphthalene-2-sulfonamide formate Mass spectrum: Found: $MH^{30}$ 563 H.p.l.c. (1) Rt 2.58 min

Example 84

6-Chloro-N-[2-(dimethylamino)ethyl]-N-{(3S)-1-[(1S)-1-methyl-2-morpholin-4-yl-2-oxoethyl]-2-oxopyrrolidin-3-yl}naphthalene-2-sulfonamide formate Mass spectrum: Found: $MH^{30}$ 537 H.p.l.c. (1) Rt 2.53 min

Example 85

N-[2-([(6-Chloro-2-naphthyl)sulfonyl]{(3S)-1-[(1S)-1-methyl-2-morpholin-4-yl-2-oxoethyl]-2-oxopyrrolidin-3-yl}amino)ethyl]acetamide Mass spectrum: Found: $MH^{30}$ 551 H.p.l.c. (1) Rt 2.91 min

Example 86

5-Chloro-N-{(3S)-1-[(1S)-1-methyl-2-morpholin-4-yl-2-oxoethyl]-2-oxopyrrolidin-3-yl}-1H-indole-2-sulfonamide Intermediate 33 (0.011 g) was dissolved in 1:1 TFA/DCM (0.5 ml) and allowed to stand at room temperature for 1 h. The mixture was concentrated under reduced pressure and the residue partitioned between saturated aqueous sodium bicarbonate and DCM. The separated organic phase was dried (over magnesium sulphate) and concentrated under a stream of nitrogen to give the title compound (0.0082 g) as white solid.

Mass spectrum: Found: $MH^{30}$ 455 H.p.l.c. (1) Rt 2.97 min

Example 87

6-Chloro-N-{(3S)-1-[(1S)-1-methyl-2-morpholin-4-yl-2-oxoethyl]-2-oxopyrrolidin-3-yl}-1,3-benzothiazole-2-sulfonamide Intermediate 58 (0.1 g) was stirred at room temperature in anhydrous acetone (3 ml) and 5% aqueous potassium permanganate (1.35 ml) for 3 h, after which additional acetone (3 ml) and 5% aqueous potassium permanganate (1.35 ml) were added. The reaction mixture was stirred for a further 18 h and filtered through Celite™. The filtrate was concentrated under reduced pressure and the residue purified by mass directed preparative h.p.l.c to give the title compound (0.0062 g) as a white solid.

Mass spectrum: Found: $MH^{30}$ 473 H.p.l.c. (1) Rt 2.98 min

Example 88

6-Chloro-N-{(3S)-1-[(1S)-1-methyl-2-(2-methyl-morpholin-4-yl)-2-oxoethyl]-2-oxopyrrolidin-3-yl}naphthalene-2-sulfonamide To polymer N-cyclohexylcarbodiimide-N'-propyloxymethyl polystyrene (0.038 g) in an Alltech™ tube was added a solution of (2S)-2-((3S)-3-{[(6-chloro-2-naphthyl)sulfonyl]amino}-2-oxopyrrolidin-1-yl)propanoic acid (0.007 g) in DCM (0.9 ml) followed by 2-methylmorpholine (0.004 g) in DMF (0.1 ml) and N,N-diisopropylethylamine (0.006 ml). The mixture was shaken at room temperature for 4 days. The tube was drained, the filtrate collected and the resin washed with DCM. The combined DCM solutions were concentrated under reduced pressure and the residue purified by mass directed preparative h.p.l.c. to give the title compound (0.0038 g) as an off-white solid.

Mass spectrum: Found: MH$^{30}$ 480 H.p.l.c. (1) Rt 3.17 min

Example 89

(E)-2-(5-Chlorothien-2-yl)-N-methyl-N-{(3S)-1-[(1S)-1-methyl-2-morpholin-4-yl-2-oxoethyl]-2-oxopyrrolidin-3-yl}ethenesulfonamide Sodium hydride (60% dispersion in oil, 0.011 g) was added to trimethysulphonium iodide (0.059 g) in dimethylsulphoxide (2 ml) between 5-10° C., and the resultant mixture was stirred at room temperature for 30 min. Example 61 (0.1 g) in dry THF (2 ml) was added between 5-10° C., and the solution stirred at room temperature for 2.25 h, at 50° C. for 70 h, cooled to room temperature and poured onto ice/water. The aqueous mixture was extracted with ethyl acetate and the combined, dried (over magnesium sulphate) organic extracts were concentrated under reduced pressure. The residue was purified using mass directed preparative h.p.l.c. to give the title compound (0.038 g) as a colourless oil.

Mass spectrum: Found: MH$^{30}$ 462 H.p.l.c. (1) Rt 2.82 min

Example 90

6-Chloro-N-{(3S)-1-[(1S)-1-methyl-2-(4-morpholinyl)-2-oxoethyl]-2-oxopyrrolidinyl}thieno[3,2-b]pyridine-2-sulfonamide The title compound was similarly prepared using Intermediate 40 and 6-chlorothieno[3,2-b]pyridine-2-sulfonyl chloride*, and the synthetic procedure decribed for Example 386 (Route 1).

Prepared according to the procedure described in U.S. Pat. No. 6,281,227.

Mass spectrum: Found: MH$^{30}$ 473 H.p.l.c. (I) Rt 2.61 min

REFERENCES

1. Klimkowski, Valentine Joseph; Kyle, Jeffrey Alan; Masters, John Joseph; Wiley, Michael Robert. PCT Int. Appl. (2000), WO 0039092.
2. Choi-Sledeski, Yong Mi; Pauls, Heinz W.; Barton, Jeffrey N.; Ewing, William R.; Green, Daniel M.; Becker, Michael R.; Gong, Yong; Levell, Julian. PCT Int. Appl. (1999), WO 9962904.

In Vitro Assay for Inhibition of Factor Xa

Compounds of the present invention were tested for their Factor Xa inhibitory activity as determined in vitro by their ability to inhibit human Factor Xa in a chromogenic assay, using N-α-benzyloxycarbonyl-D-Arg-Gly-Arg-p-nitroanilide as the chromogenic substrate. Compounds were diluted from a 10 mM stock solution in dimethylsulfoxide at appropriate concentrations. Assay was performed at room temperature using buffer consisting of: 50 mM Tris-HCl, 150 mM NaCl, 5 mM CaCl2, pH 7.4. containing human Factor Xa (final conc. Of 0.0015 U.ml−1). Compound and enzyme were preincubated for 15 min prior to addition of the substrate (final conc. of 200 μM). The reaction was stopped after 30 min with the addition of soybean trypsin inhibitor or H-D-PHE-PRO-ARG-Chloromethylketone. BioTek EL340 or Tecan SpectraFluor Plus plate readers were used to monitor the absorbance at 405 nM. To obtain IC50 values the data were analysed using ActivityBase® and XLfit®.

All of the synthetic Example compounds tested (Examples 1-52, 54-89) exhibited IC$_{50}$ values of less than 60 μM. Preferably compounds have an IC$_{50}$ value of less than 2 μM, more preferably compounds have an IC$_{50}$ value of less than 0.1 μM.

Measurement of Prothrombin Time (PT)—Test 1

Blood was collected into a sodium citrate solution (ratio 9:1) to give a final concentration of 0.38% citrate. Plasma was generated by centrifugation of citrated blood samples at 1200×g for 20 min at 4° C.

The PT test was performed at 37° C. in plastic cuvettes containing a magnetic ball bearing. 50 μL of citrated plasma and either 25 μL of 2.8% DMSO for control or 25μL of test compound (dissolved in DMSO and diluted in water and 2.8% DMSO to give 0.4% DMSO final in assay) at a concentration of 7-times the final desired concentration was pippetted into each cuvette. This mixture was incubated for 1 min at 37° C. before adding 100 μL of thromboplastin mixture (comprising lyophilised rabbit thromboplastin and calcium chloride which was reconstituted in distilled water as per manufacturer's [Sigma] instructions). On addition of the thromboplastin mixture, the timer was automatically started and continued until the plasma clotted. The time to clotting was recorded (normal range for human plasma is 10-13 seconds).

Method for Measurement of Prothrombin Time (PT)—Test 2

Blood is collected into a sodium citrate solution (ratio 9:1) to give a final concentration of 0.38% citrate. Plasma is generated by centrifugation of citrated blood samples at 1200×g for 20 min at 4° C.

The PT test is performed at 37° C. in plastic cassettes and using a MCA210 Microsample Coagulation Analyzer (Bio/Data Corporation). For assay, 25 ul of plasma containing test compound at concentrations ranging from 0.1 to 100 uM (made from a 1 mM stock solution in 10% DMSO and plasma) and 25 ul of Thromboplastin C Plus (Dade Berhing) are automatically injected into the cassette. Upon addition of the Thromboplastin C Plus, the instrument determines and records the time to clot (normal range for human plasma is 10-13 seconds).

General Purification and Analytical Methods

Analytical HPLC was conducted on a Supelcosil LCABZ+PLUS column (3 μm, 3.3 cm×4.6 mm ID) eluting with 0.1% HCO$_2$H and 0.01 M ammonium acetate in water (solvent A), and 95% acetonitrile and 0.05% HCO$_2$H in water (solvent B), using the following elution gradient 0-0.7 minutes 0% B, 0.7-4.2 minutes 0→100% B, 4.2-5.3 minutes 100% B, 5.3-5.5 minutes 100→0% B at a flow rate of 3 ml/minutes (System 1). The mass spectra (MS) were recorded on a Fisons VG Platform mass spectrometer using electrospray positive ionisation [(ES+ve to give MH+ and M(NH4)+ molecular ions] or electrospray negative ionisation [(ES−ve to give (M−H)− molecular ion] modes.

LC/MS System (3)

Method 2 was conducted on a Waters Xtera RP18 column (3 μm, 15 cm×2.1 mm ID) eluting with solvent A (0.1% HCO2H and water) and solvent B (100% acetonitrile, 0.1% HCO2H and reserpine 2.5 μgml-1) at 20° C. The following elution gradient was ran: 0-2.0 minutes 0% B; 2.0-18.0 minutes 0-100% B; 18.0-20.0 minutes 100% B; 20.0-22.0 minutes 100-0% B; 22.0-30.0 minutes 0% B, at a flow rate of 0.4 ml/minutes. The mass spectra (MS) were recorded on a Micromass QTOF 2 spectrometer using electrospray positive ionisation [ES+ve to give MH+].

Note: The number given in brackets in the Examples and Intermediates above, e.g. H.p.l.c. (1), specifies the LC/MS method used.

$^1$H nmr spectra were recorded using a Bruker DPX 400 MHz spectrometer using tetramethylsilane as the external standard.

Biotage™ chromatography refers to purification carried out using equipment sold by Dyax Corporation (either the Flash 40i or Flash 150i) and cartridges pre-packed with KPSil.

Mass directed autoprep refers to methods where the material was purified by high performance liquid chromatography on a HPLCABZ+5 μm column (5 cm×10 mm i.d.) with 0.1% HCO2H in water and 95% MeCN, 5% water (0.5% HCO2H) utilising the following gradient elution conditions: 0-1.0 minutes 5% B, 1.0-8.0 minutes 5→30% B, 8.0-8.9 minutes 30% B, 8.9-9.0 minutes 30→95% B, 9.0-9.9 minutes 95% B, 9.9-10 minutes 95→0% B at a flow rate of 8 ml minutes$^{-1}$ (System 2). The Gilson 202-fraction collector was triggered by a VG Platform Mass Spectrometer on detecting the mass of interest. Hydrpophobic frits refers to filtration tubes sold by Whatman.

SPE (solid phase extraction) refers to the use of cartridges sold by International Sorbent Technology Ltd.

TLC (thin layer chromatography) refers to the use of TLC plates sold by Merck coated with silica gel 60 $F_{254}$.

The invention claimed is:

1. A method for preparing a compound of formula (I):

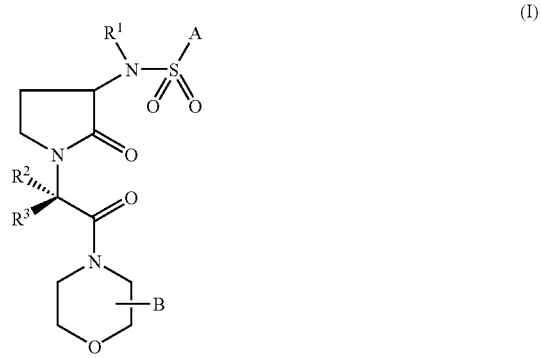

(I)

wherein:

R$^1$ represents hydrogen, —C$_{1-6}$alkyl, —C$_{3-6}$alkenyl, —C$_{2-3}$alkylNR$^b$R$^c$, —C$_{2-3}$alkylNHCOR$^b$, phenyl being optionally substituted by halogen, or R$^1$ represents a group X—W, wherein X represents —C$_{1-3}$alkylene- and W represents —CN, —CO$_2$H, —CONR$^b$R$^c$, —COC$_{1-6}$alkyl, —CO$_2$C$_{1-6}$alkyl, or phenyl, the phenyl being optionally substituted by one or more substitutents selected from: —C$_{1-3}$alkyl, —C$_{1-3}$alkoxy, —C$_{1-3}$alkylOH, halogen, —CN, —CF$_3$, —NH$_2$, —CO$_2$H and —OH;

R$^2$ and R$^3$ independently represent hydrogen, —C$_{1-3}$alkyl or —CF$_3$ with the proviso that one of R$^2$ and R$^3$ is —C$_{1-3}$alkyl or —CF$_3$ and the other is hydrogen;

R$^b$ and R$^c$ independently represent hydrogen or —C$_{1-3}$alkyl;

A represents:

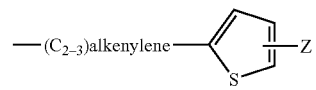

Z represents one or two optional substituents independently selected from halogen and OH, B represents one or more optional substituents on ring carbon atoms selected from:

(i) one or more substituents selected from —CF$_3$, —F, —CO$_2$H, —C$_{1-6}$alkyl, —C$_{1-6}$alkylOH, —(C$_{1-3}$alkyl)NR$^b$R$^c$, —(C$_{0-3}$alkyl)CONR$^b$R$^c$ and —(C$_{0-3}$alkyl)CO$_2$C$_{1-3}$alkyl, —CONHC$_{2-3}$alkylOH, —CH$_2$NHC$_{2-3}$alkylOH, —CH$_2$OC$_{1-3}$alkyl and —CH$_2$SO$_2$C$_{1-3}$alkyl;

(ii) a group —Y—R$^e$,

Y represents —C$_{1-3}$alkylene-, —CO—, —C$_{1-3}$alkylNH—, —C$_{1-3}$alkylNHCO—, —C$_{1-3}$alkylNHSO$_2$—, —CH$_2$NHSO$_2$CH$_2$— or a direct link, R$^e$ represents phenyl, a 5- or 6-membered cycloalkyl or a 5- or 6-membered heterocycle consisting of at least one heteroatom selected from O or S, each of which is optionally substituted by one or more substituents selected from: —C$_{1-3}$alkyl, —C$_{1-3}$alkoxy, —C$_{1-3}$alkylOH, halogen, —CN, —CF$_3$, —NH$_2$, —CO$_2$H and —OH; or (iii) a second ring R$^f$ which is fused to the heterocyclic ring, wherein R$^f$ represents phenyl, a 5- or 6-membered cycloalkyl group or a 5- or 6-membered aromatic heterocyclic group consisting of at least one heteroatom selected from O, N or S, and the fused bicyclic group is optionally substituted by one or more substituents selected from: —C$_{1-3}$alkyl, —C$_{1-3}$alkoxy, —C$_{1-3}$alkylOH, halogen, —CN, —CF$_3$, —NH$_2$, —CO$_2$H and —OH;

wherein said method comprises the step of reacting a compound of formula (II) with a compound of formula (III):

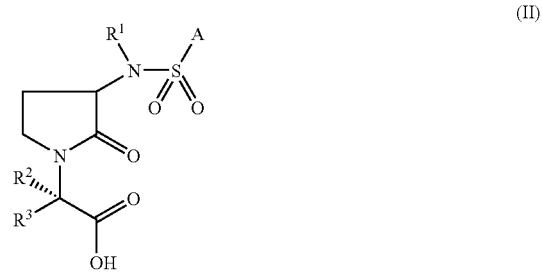

(II)

-continued

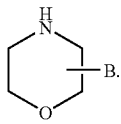

(III)

2. A method for preparing a compound of formula (I):

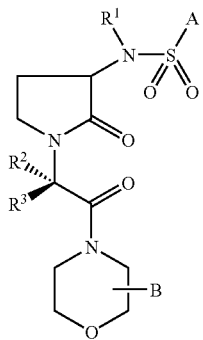

(I)

wherein:

$R^1$ represents hydrogen, —$C_{1-6}$alkyl, —$C_{3-6}$alkenyl, —$C_{2-3}$alkylNR$^b$R$^c$, —$C_{2-3}$alkylNHCOR$^b$, phenyl being optionally substituted by halogen, or $R^1$ represents a group X—W, wherein X represents —$C_{1-3}$ alkylene- and W represents —CN, —$CO_2H$, —CONR$^b$R$^c$, —CO$C_{1-6}$alkyl, —$CO_2C_{1-6}$alkyl, or phenyl, the phenyl being optionally substituted by one or more substitutents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;

$R^2$ and $R^3$ independently represent hydrogen, —$C_{1-3}$alkyl or —$CF_3$ with the proviso that one of $R^2$ and $R^3$ is —$C_{1-3}$alkyl or —$CF_3$ and the other is hydrogen;

$R^b$ and $R^c$ independently represent hydrogen or —$C_{1-3}$ alkyl;

A represents:

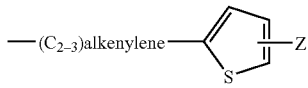

Z represents one or two optional substituents independently selected from halogen and OH, B represents one or more optional substituents on ring carbon atoms selected from:

(i) one or more substituents selected from —$CF_3$, —F, —$CO_2H$, —$C_{1-6}$alkyl, —$C_{1-6}$alkylOH, —($C_{1-3}$alkyl)NR$^b$R$^c$, —($C_{0-3}$alkyl)CONR$^b$R$^c$ and —($C_{0-3}$alkyl)$CO_2C_{1-3}$alkyl, —CONH$C_{2-3}$alkylOH, —$CH_2$NH$C_{2-3}$alkylOH, —$CH_2$O$C_{1-3}$alkyl and —$CH_2SO_2C_{1-3}$alkyl;

(ii) a group —Y—R$^e$,

Y represents —$C_{1-3}$alkylene-, —CO—, —$C_{1-3}$alkylNH—, —$C_{1-3}$alkylNHCO—, —$C_{1-3}$alkylNHSO$_2$—, —$CH_2NHSO_2CH_2$— or a direct link, R$^e$ represents phenyl, a 5- or 6-membered cycloalkyl or a 5- or 6-membered heterocycle consisting of at least one heteroatom selected from O or S, each of which is optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH; or (iii) a second ring $R^f$ which is fused to the heterocyclic ring, wherein $R^f$ represents phenyl, a 5- or 6-membered cycloalkyl group or a 5- or 6-membered aromatic heterocyclic group consisting of at least one heteroatom selected from O, N or S, and the fused bicyclic group is optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;

wherein said method comprises the step of reacting a compound of formula (IV) with a compound of formula (VI):

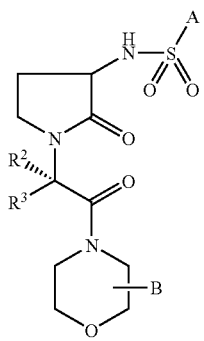

(XV)

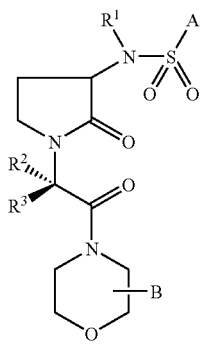

(VI)

$R^1$— Halogen.

3. A method for preparing a compound of formula (I):

(I)

wherein:

$R^1$ represents hydrogen, —$C_{1-6}$alkyl, —$C_{3-6}$alkenyl, —$C_{2-3}$alkylNR$^b$R$^c$, —$C_{2-3}$alkylNHCOR$^b$, phenyl being optionally substituted by halogen, or $R^1$ represents a group X—W, wherein X represents —$C_{1-3}$ alkylene- and W represents —CN, —$CO_2H$, —CONR$^b$R$^c$, —CO$C_{1-6}$alkyl, —$CO_2C_{1-6}$alkyl, or phenyl, the phenyl being optionally substituted by one or more substitutents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;

$R^2$ and $R^3$ independently represent hydrogen, —$C_{1-3}$alkyl or —$CF_3$ with the proviso that one of $R^2$ and $R^3$ is —$C_{1-3}$alkyl or —$CF_3$ and the other is hydrogen;

$R^b$ and $R^c$ independently represent hydrogen or —$C_{1-3}$alkyl;

A represents:

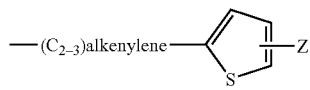

Z represents one or two optional substituents independently selected from halogen and OH, B represents one or more optional substituents on ring carbon atoms selected from:

(i) one or more substituents selected from —$CF_3$, —F, —$CO_2H$, —$C_{1-6}$alkyl, —$C_{1-6}$alkylOH, —$(C_{1-3}$alkyl)$NR^bR^c$, —$(C_{0-3}$alkyl)$CONR^bR^c$ and —$(C_{0-3}$alkyl)$CO_2C_{1-3}$alkyl, —$CONHC_{2-3}$alkylOH, —$CH_2NHC_{2-3}$alkylOH, —$CH_2OC_{1-3}$alkyl and —$CH_2SO_2C_{1-3}$alkyl;

(ii) a group —Y—$R^e$,

Y represents —$C_{1-3}$alkylene-, —CO—, —$C_{1-3}$alkylNH—, —$C_{1-3}$alkylNHCO—, —$C_{1-3}$alkylNHSO_2—, —$CH_2NHSO_2CH_2$— or a direct link, $R^e$ represents phenyl, a 5- or 6-membered cycloalkyl or a 5- or 6-membered heterocycle consisting of at least one heteroatom selected from O or S, each of which is optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH; or (iii) a second ring $R^f$ which is fused to the heterocyclic ring, wherein $R^f$ represents phenyl, a 5- or 6-membered cycloalkyl group or a 5- or 6-membered aromatic heterocyclic group consisting of at least one heteroatom selected from O, N or S, and the fused bicyclic group is optionally substituted by one or more substituents selected from: —$C_{1-3}$alkyl, —$C_{1-3}$alkoxy, —$C_{1-3}$alkylOH, halogen, —CN, —$CF_3$, —$NH_2$, —$CO_2H$ and —OH;

wherein said method comprises the step of reacting a compound of formula (XVI) with a compound of formula (VIII):

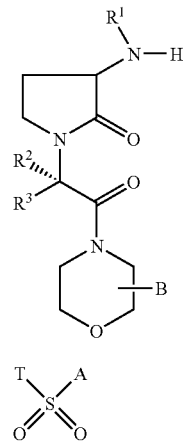

(XVI)

(VIII)

wherein T represents halide.

* * * * *